(12) United States Patent
Pfleger et al.

(10) Patent No.: US 12,116,609 B2
(45) Date of Patent: Oct. 15, 2024

(54) BIOCONVERSION OF LEVULINIC ACID IN GENETICALLY ENGINEERED HOSTS

(71) Applicant: Wisconsin Alumni Research Foundation, Madison, WI (US)

(72) Inventors: Brian Frederick Pfleger, Madison, WI (US); Jacqueline Marie Rand, Madison, WI (US); Christopher Robert Mehrer, Madison, WI (US); Matthew Ryan Incha, Berkeley, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 845 days.

(21) Appl. No.: 17/159,850

(22) Filed: Jan. 27, 2021

(65) Prior Publication Data
US 2021/0155961 A1  May 27, 2021

Related U.S. Application Data

(62) Division of application No. 16/135,123, filed on Sep. 19, 2018, now Pat. No. 10,934,563.

(60) Provisional application No. 62/560,247, filed on Sep. 19, 2017.

(51) Int. Cl.
| | | |
|---|---|---|
| C12P 7/04 | (2006.01) |
| C12N 9/10 | (2006.01) |
| C12N 9/18 | (2006.01) |
| C12N 15/52 | (2006.01) |
| C12N 15/62 | (2006.01) |
| C12N 15/63 | (2006.01) |
| C12N 15/64 | (2006.01) |
| C12N 15/66 | (2006.01) |
| C12N 15/69 | (2006.01) |
| C12P 7/16 | (2006.01) |
| C12P 7/26 | (2006.01) |

(52) U.S. Cl.
CPC .............. *C12P 7/16* (2013.01); *C12N 9/1029* (2013.01); *C12N 9/18* (2013.01); *C12N 15/52* (2013.01); *C12N 15/62* (2013.01); *C12N 15/63* (2013.01); *C12N 15/64* (2013.01); *C12N 15/66* (2013.01); *C12N 15/69* (2013.01); *C12P 7/26* (2013.01); *C12Y 203/01009* (2013.01); *C12Y 208/03* (2013.01); *C12Y 301/01* (2013.01)

(58) Field of Classification Search
CPC ........... C12P 7/16; C12N 9/1029; C12N 9/18
See application file for complete search history.

(56) References Cited

FOREIGN PATENT DOCUMENTS

KR        102177736 B1 * 11/2020

OTHER PUBLICATIONS

English Translation of KR 102177736. Retrieved on Feb. 5, 2024.*
Fransceus. J Ind Microbiol Biotechnol. May 2017;44(4-5):687-695.*

(Continued)

*Primary Examiner* — Yong D Pak
(74) *Attorney, Agent, or Firm* — Joseph T. Leone; DeWitt LLP

(57) ABSTRACT

Described is a recombinant expression vector that enables a cell transformed to contain and express the vector to use levulinic acid as a carbon source, thereby converting levulnic acid into 2-butanne. Also described are genetically modified cells transformed to contain and express the vector and methods of using the cells to produce 2-butanone from a medium containing levulinic acid.

3 Claims, 16 Drawing Sheets

Specification includes a Sequence Listing.

(SEQ. ID. NO: 48)

(56) References Cited

OTHER PUBLICATIONS

Sanavia. Computational and Structural Biotechnology Journal, vol. 18, 2020, pp. 1968-1979.*
Rand. A metabolic pathway for catabolizing levulinic acid in bacteria. Nat Microbiol. Dec. 2017;2(12):1624-1634. doi: 10.1038/s41564-017-0028-z. Epub Sep. 25, 2017.*
Alonso, D. M. et al., Gamma-valerolactone, a sustainable platform molecule derived from lignocellulosic biomass. *Green Chem.* 15, 584 (2013).
Altschul et al., "Basic local alignment search tool," *Journal of Molecular Biology.* 215(3):403-410 (1990).
Ausubel, et al., Short Protocols in Molecular Biology, 5th ed., Wiley & Sons, (2002).
Barrios, H. et al., Compilation and analysis of sigma(54)-dependent promoter sequences. *Nucleic Acids Res.* 27, 4305-4313 (1999).
Berezina, N. et al., Improvement of the poly(3-hydroxybutyrate-co-3-hydroxyvalerate) (PHBV) production by dual feeding with levulinic acid and sodium propionate in *Cupriavidus necator. N. Biotechnol.* 33, 231-236 (2016).
Carlier, A. et al.,. The assimilation of gamma-butyrolactone in Agrobacterium tumefaciens C58 interferes with the accumulation of the N-acyl-homoserine lactone signal. *Mol. Plant. Microbe. Interact.* 17, 951-7 (2004).
Chatterjee, A. eet al., PsrA, the Pseudomonas sigma regulator, controls regulators of epiphytic fitness, quorum-sensing signals, and plant interactions in *Pseudomonas syringae* pv. tomato strain DC3000. *Appl. Environ. Microbiol.* 73, 3684-3694 (2007).
Chow, J. Y. et al. Directed evolution of a thermostable quorum-quenching lactonase from the amidohydrolase superfamily. *J. Biol. Chem.* 285, 40911-20 (2010).
Chung, S. H. et al., Effect of Levulinic Acid on the Production of Poly(3-hydroxybutyrate-co-3-hydroxyvalerate) by *Ralstonia eutropha* KHB-8862. *Society* 39, 79-82 (2001).
Cock, P. J. A. et al. Biopython: freely available Python tools for computational molecular biology and bioinformatics. *Bioinformatics* 25, 1422-3 (2009).
Dijkman, W. P. et al., Discovery and characterization of a 5-hydroxymethylfurfural oxidase from *Methylovorus* sp. strain MP688. *Appl. Environ. Microbiol.* 80, 1082-1090 (2014).
Edgar, RC "MUSCLE: a multiple sequence alignment method with reduced time and space complexity," *BMC Bioinformatics,* 5:113 (2004).
Espah Borujeni, A., et al., Translation rate is controlled by coupled trade-offs between site accessibility, selective RNA unfolding and sliding at upstream standby sites. *Nucleic Acids Res.* 42, 2646-2659 (2014).
Fox, J. D. et al., Maltodextrin-binding proteins from diverse bacteria and archaea are potent solubility enhancers. *FEBS Lett.* 537, 53-57 (2003).
Gibson et al., Enzymatic assembly of DNA molecules up to several hundred kilobases, *Nat. Methods* 6, 343-5 (2009).
Graf, N. et al., Development of a method for markerless gene deletion in Pseudomonas putida. *Appl. Environ. Microbiol.* 77, 5549-52 (2011).
Green, M.R. and Sambrook, J., *Molecular Cloning: A Laboratory Manual (Fourth Edition),* Cold Spring Harbor Laboratory Press, 2012, ISBN-10: 1936113422.
Habe, H. et al. Bacterial production of short-chain organic acids and trehalose from levulinic acid: A potential cellulose-derived building block as a feedstock for microbial production. *Bioresour. Technol.* 177, 381-386 (2015).
Harris, S. R. et al. Metabolism of levulinate in perfused rat livers and live rats: Conversion to the drug of abuse 4-hydroxypentanoate. *J. Biol. Chem.* 286, 5895-5904 (2011).
Hiblot, J. et al., Structural and enzymatic characterization of the lactonase SisLac from Sulfolobus islandicus. *PLoS One* 7, e47028 (2012).
Jang, J. H. et al., Effect of levulinic acid on cell growth and poly-beta-hydroxyalkanoate production by *Alcaligenes* sp SH-69. *J. Chem. Inf. Model.* 18, 219-224 (1996).
Jaremko, M. et al., The initial metabolic conversion of levulinic acid in *Cupriavidus necator. J. Biotechnol.* 155, 293-298 (2011).
Jenkins, L. S. et al., Genetic and molecular characterization of the genes involved in short-chain fatty acid degradation in *Escherichia coli:* the ato system. *J Bacteriol* 169, 42-52 (1987).
Jiang, W. et al., RNA-guided editing of bacterial genomes using CRISPR-Cas systems. *Nat Biotechnol* 31, 233-239 (2013).
Jiang, Y. et al. Multigene editing in the *Escherichia coli* genome via the CRISPR-Cas9 system. *Appl. Environ. Microbiol.* 81, 2506-2514 (2015).
Katoh, M. et al., "MAFFT: a novel method for rapid multiple sequence alignment based on fast Fourier transform," *Nucleic Acids Res.* 30:3059-3066 (2002).
Kittle et al., Insertion Sequence IS10 Anti-sense Pairing Initiates by an Interaction Between the 5' End of the Target RNA and a Loop in the Anti-sense RNA, *J Mol. Biol.* 210 (3):561-72 (1989).
Kohler, C. et al., Extracytoplasmic function (ECF) sigma factor σF is involved in Caulobacter crescentus response to heavy metal stress. *BMC Microbiol.* 12, 210 (2012).
Korz et al. "Simple fed-batch technique for high cell density cultivation of *Escherichia coli.,*" *J. Biotechnol.* 39, 59-65 (1995).
Li, Y. et al. Metabolic engineering of *Escherichia coli* using CRISPR-Cas9 meditated genome editing. *Metab. Eng.* 31, 13-21 (2015).
Luterbacher, J. S. et al. Nonenzymatic Sugar Production from Biomass Using Biomass-Derived gamma-Valerolactone. *Science* (80-. ). 343, 277-281 (2014).
Luterbacher, J. S. et al. Lignin monomer production integrated into the γ-valerolactone sugar platform. *Energy Environ. Sci.* 8, 2657-2663 (2015).
Man, W. J.. et al., The Binding of Propionyl-Coa and Carboxymethyl-Coa to *Escherichia coli* Citrate Synthase. *Biochim. Biophys. Acta* 1250, 69-75 (1995).
Martin, C. H. et al., High-titer production of monomeric hydroxyvalerates from levulinic acid in *Pseudomonas putida. J. Biotechnol.* 139, 61-67 (2009).
Martin, C. H. et al., Integrated bioprocessing for the pH-dependent production of 4-valerolactone from levulinate in pseudomonas putida KT2440. *Appl. Environ. Microbiol.* 76, 417-424 (2010).
Martínez-García, E. et al., pBAM1: an all-synthetic genetic tool for analysis and construction of complex bacterial phenotypes. *BMC Microbiol.* 11, 38 (2011).
Min, K. et al. Conversion of levulinic acid to 2-butanone by acetoacetate decarboxylase from Clostridium acetobutylicum. *Appl. Microbiol. Biotechnol.* 97, 5627-5634 (2013).
Mutalik et al., Rationally designed families of orthoganl RNA regulators of translation, *Nature Chem. Biol.* 447-454 (2012).
Neidhardt, F. C. et al., Culture medium for enterobacteria. *J. Bacteriol.* 119, 736-747 (1974).
Ng, F. S. W. et al., Characterization of a phosphotriesterase-like lactonase from Sulfolobus solfataricus and its immobilization for disruption of quorum sensing. *Appl. Environ. Microbiol.* 77, 1181-1186 (2011).
Notredame C. et al., "T-Coffee: A novel method for fast and accurate multiple sequence alignment," *J Mol Biol* 302(1):205-217 (Sep. 8, 2000).
Onakunle, O., et al., The formation and substrate specificity of bacterial lactonases capable of enantioselective resolution of racemic lactones. *Enzyme Microb. Technol.* 21, 245-251 (1997).
Pearson, J. P. et al., A second N-acylhomoserine lactone signal produced by Pseudomonas aeruginosa. *Proc. Natl. Acad. Sci. U. S. A.* 92, 1490-1494 (1995).
Pedelacq JD et al., Engineering and characterization of a superfolder green fluorescent protein, *Nat Biotechnol.* 24(1):79-88 (2006).
Pinto, F. L. et al., Analysis of current and alternative phenol based RNA extraction methodologies for cyanobacteria. *BMC Mol. Biol.* 10, 79 (2009).
Politz, M. C. Transcription Activator-Like Effectors as Tools for Prokaryotic Synthetic Biology. (University Of Wisconsin-Madison, 2016).

(56) References Cited

OTHER PUBLICATIONS

Qi, L. S. et al. Repurposing CRISPR as an RNA-guided platform for sequence-specific control of gene expression. *Cell* 152, 1173-1183 (2013).

Quan, J. et al., Circular polymerase extension cloning for high-throughput cloning of complex and combinatorial DNA libraries, *J. Nat. Protoc.* 6, 242-251; (2011).

Riesenberg et al., "High cell density cultivation of *Escherichia coli* at controlled specific growth rate," *J. Biotechnol.* 20, 17-27 (1991).

Salis, H. M. M. et al., Automated design of synthetic ribosome binding sites to control protein expression. *Nat. Biotechnol.* 27, 946-50 (2009).

Schäfer, A. et al. Small mobilizable multi-purpose cloning vectors derived from the *Escherichia coli* plasmids pK18 and pK19: selection of defined deletions in the chromosome of Corynebacterium glutamicum. *Gene* 145, 69-73 (1994).

Schramm, G. et al., A simple and reliable 5'-RACE approach. *Nucleic Acids Res* 28, E96 (2000).

Serrano-Ruiz, J. C. et al., Catalytic Conversion of Renewable Biomass Resources to Fuels and Chemicals. *Annu. Rev. Chem. Biomol. Eng.* 1, 79-100 (2010).

Shetty et al., Engineering BioBrick vectors from BioBrick parts, *J. Biol. Eng.* 2, 5 (2008).

Striebel, F. et al. Bacterial ubiquitin-like modifier Pup is deamidated and conjugated to substrates by distinct but homologous enzymes. *Nat. Struct. Mol. Biol.* 16, 647-651 (2009).

Uroz, S. et al., Quorum sensing and quorum quenching: The Yin and Yang of bacterial communication. *ChemBioChem* 10, 205-216 (2009).

Valentin, H. E. et al., Identification of 5-hydroxyhexanoic acid, 4-hydroxyheptanoic acid and 4-hydroxyoctanoic acid as new constituents of bacterial polyhydroxyalkanoic acids. *Appl. Microbiol. Biotechnol.* 46, 261-267 (1996).

Wargo, M. J. et al., Identification of genes required for Pseudomonas aeruginosa carnitine catabolism. *Microbiology* 155, 2411-2419 (2009).

Wetmore, K. M. M. et al. Rapid Quantification of Mutant Fitness in Diverse Bacteria by Sequencing Randomly Bar-Coded Transposons. *MBio* 6, 1-15 (2015).

Yamamoto, S. et al., . FliT acts as an anti-FlhD2C2 factor in the transcriptional control of the flagellar regulon in *Salmonella enterica* serovar typhimurium. *J. Bacteriol.* 188, 6703-8 (2006).

Yeon, Y. J. et al., Enzymatic reduction of levulinic acid by engineering the substrate specificity of 3-hydroxybutyrate dehydrogenase. *Bioresour. Technol.* 134, 377-380 (2013).

Yoneda, H. et al., Biological production of 2-butanone in *Escherichia coli*. *ChemSusChem* 7, 92-95 (2014).

Zhang, G. F. et al. Catabolism of 4-hydroxyacids and 4-hydroxynonenal via 4-hydroxy-4-phosphoacyl-CoAs. *J. Biol. Chem.* 284, 33521-33534 (2009).

\* cited by examiner

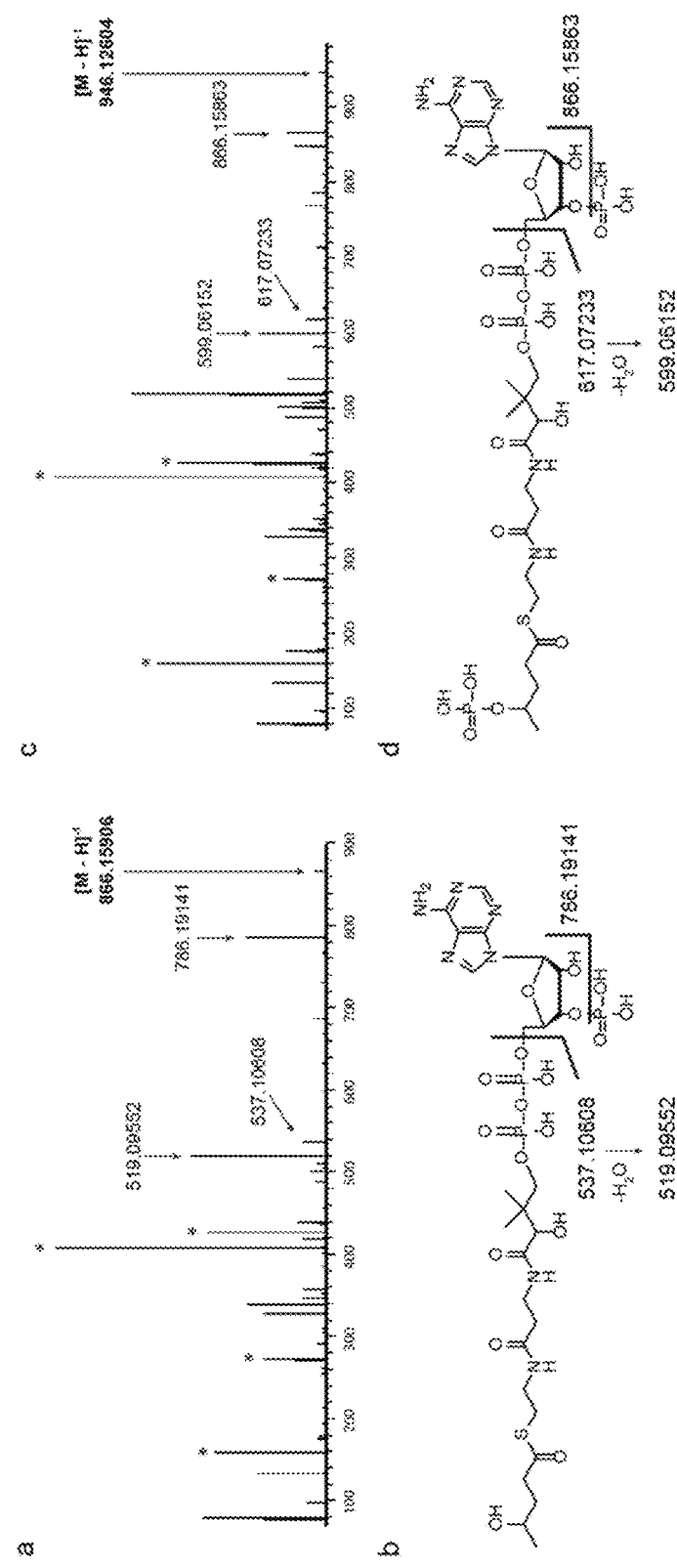

(a) Growth on LA (b) Growth on LA + Acetate (c) ΔatoB (d) Δacs ΔackApta

SEQUENCE LISTING

```
<160> NUMBER OF SEQ ID NOS: 48

<210> SEQ ID NO 1
<211> LENGTH: 1059
<212> TYPE: DNA
<213> ORGANISM: Pseudomonas putida
<220> FEATURE:
<221> NAME/KEY: CDS
<222> LOCATION: (1)..(1059)

<400> SEQUENCE: 1 atg agc agt tca cca acg att tcc ccg gcc agc gat acg ttc gcg gcc      48
Met Ser Ser Ser Pro Thr Ile Ser Pro Ala Ser Asp Thr Phe Ala Ala
1               5                   10                  15 atg act gac gat cac cgc ctg gcc gag ttc atc cgc gag cag gcc tcg      96
Met Thr Asp Asp His Arg Leu Ala Glu Phe Ile Arg Glu Gln Ala Ser
            20                  25                  30 gca acg cgg gtg gtc atc cag gcg cgc aag cgc ctg agc ggc ggc gct     144
Ala Thr Arg Val Val Ile Gln Ala Arg Lys Arg Leu Ser Gly Gly Ala
        35                  40                  45 atc cag gaa aac tgg ctg ctg gac ctg ctg atc gaa ggc ggc ccg tgg     192
Ile Gln Glu Asn Trp Leu Leu Asp Leu Leu Ile Glu Gly Gly Pro Trp
    50                  55                  60 gcc ggt gtc cgg cgt tgg gta ctg cgc agc gat gcg ctt tca gcg cta     240
Ala Gly Val Arg Arg Trp Val Leu Arg Ser Asp Ala Leu Ser Ala Leu
65                  70                  75                  80 ccc gcc agc ctt gac cgt gaa cag gag ttc gcc gtg ctg cag gtg gtt     288
Pro Ala Ser Leu Asp Arg Glu Gln Glu Phe Ala Val Leu Gln Val Val
                85                  90                  95 tac cag gcc ggc gtg aaa gtg cca cgc ccg ctc tgg ctg tgc cgc gat     336
Tyr Gln Ala Gly Val Lys Val Pro Arg Pro Leu Trp Leu Cys Arg Asp
            100                 105                 110 gtg cgc gtg cat ggg cgg gtg ttc ttc ctg atg gag tat gtg ccg ggt     384
Val Arg Val His Gly Arg Val Phe Phe Leu Met Glu Tyr Val Pro Gly
        115                 120                 125 agc gct gcc ggc cgc gcg ctc agc acc ggc gcc ggt cct cag ggc cgg     432
Ser Ala Ala Gly Arg Ala Leu Ser Thr Gly Ala Gly Pro Gln Gly Arg
    130                 135                 140
```

```
gcg caa ctg gcg acg cag ctt ggc gcc aac ctg gcg cgt ctg cat cag      480
Ala Gln Leu Ala Thr Gln Leu Gly Ala Asn Leu Ala Arg Leu His Gln
145                 150                 155                 160 gtc cgc ccg ccg tgc gcc acg ctg tgc ttc ctg tcc gtt ccg gac agc      528
Val Arg Pro Pro Cys Ala Thr Leu Cys Phe Leu Ser Val Pro Asp Ser
                165                 170                 175 tcg ccg gcc ctg gcg acc atc gac gcc tac cgc cgc tac ctc gac acc      576
Ser Pro Ala Leu Ala Thr Ile Asp Ala Tyr Arg Arg Tyr Leu Asp Thr
            180                 185                 190 ctc gcc gat gcc tat ccg gtg ctg gaa tgg ggc ctg cgc tgg tgc gag      624
Leu Ala Asp Ala Tyr Pro Val Leu Glu Trp Gly Leu Arg Trp Cys Glu
        195                 200                 205 ctg cat gcg ccg cgc agc agc acc ctg tgc ctg ttg cac cgt gac tac      672
Leu His Ala Pro Arg Ser Ser Thr Leu Cys Leu Leu His Arg Asp Tyr
    210                 215                 220 cgc acc ggc aac tac ctg gcc agc gaa gaa ggg ctg gag gcc gtg ctc      720
Arg Thr Gly Asn Tyr Leu Ala Ser Glu Glu Gly Leu Glu Ala Val Leu
225                 230                 235                 240 gac tgg gag ttc acc ggc tgg gga gat cct tgc gag gac ctc ggc tgg      768
Asp Trp Glu Phe Thr Gly Trp Gly Asp Pro Cys Glu Asp Leu Gly Trp
                245                 250                 255 ttc acc gcc cgt tgc tgg cgt ttt acc cgt cca gac ctc gaa gcc ggc      816
Phe Thr Ala Arg Cys Trp Arg Phe Thr Arg Pro Asp Leu Glu Ala Gly
            260                 265                 270 ggc att ggc cag ctg gag gat ttt ctg cgt ggt tat cac gag gtg tct      864
Gly Ile Gly Gln Leu Glu Asp Phe Leu Arg Gly Tyr His Glu Val Ser
        275                 280                 285 tcg ctg tgc atc gag cgc agt cgg ctc cac tac tgg caa gtc atg gcc      912
Ser Leu Cys Ile Glu Arg Ser Arg Leu His Tyr Trp Gln Val Met Ala
    290                 295                 300 acc ctg cgc tgg gcg gtg att gcc ttg cag caa ggg cag cgc cat ctg      960
Thr Leu Arg Trp Ala Val Ile Ala Leu Gln Gln Gly Gln Arg His Leu
305                 310                 315                 320 tcc ggt gaa gaa ccg tcg ctc gag cta gca ctg aca gcc cgg ctg ttg     1008
Ser Gly Glu Glu Pro Ser Leu Glu Leu Ala Leu Thr Ala Arg Leu Leu
                325                 330                 335 ccg gag ctc gaa ctc gac atc ctg cac atg acc gga gcc gaa gcg cca     1056
Pro Glu Leu Glu Leu Asp Ile Leu His Met Thr Gly Ala Glu Ala Pro
            340                 345                 350 tga                                                                 1059

<210> SEQ ID NO 2
<211> LENGTH: 352
<212> TYPE: PRT
<213> ORGANISM: Pseudomonas putida

<400> SEQUENCE: 2

Met Ser Ser Ser Pro Thr Ile Ser Pro Ala Ser Asp Thr Phe Ala Ala
1               5                   10                  15

Met Thr Asp Asp His Arg Leu Ala Glu Phe Ile Arg Glu Gln Ala Ser
            20                  25                  30

Ala Thr Arg Val Val Ile Gln Ala Arg Lys Arg Leu Ser Gly Gly Ala
        35                  40                  45

Ile Gln Glu Asn Trp Leu Leu Asp Leu Leu Ile Glu Gly Gly Pro Trp
    50                  55                  60

Ala Gly Val Arg Arg Trp Val Leu Arg Ser Asp Ala Leu Ser Ala Leu
65                  70                  75                  80

Pro Ala Ser Leu Asp Arg Glu Gln Glu Phe Ala Val Leu Gln Val Val
```

```
                        85                  90                  95
Tyr Gln Ala Gly Val Lys Val Pro Arg Pro Leu Trp Leu Cys Arg Asp
            100                 105                 110

Val Arg Val His Gly Arg Val Phe Phe Leu Met Glu Tyr Val Pro Gly
            115                 120                 125

Ser Ala Ala Gly Arg Ala Leu Ser Thr Gly Ala Gly Pro Gln Gly Arg
            130                 135                 140

Ala Gln Leu Ala Thr Gln Leu Gly Ala Asn Leu Ala Arg Leu His Gln
145                 150                 155                 160

Val Arg Pro Pro Cys Ala Thr Leu Cys Phe Leu Ser Val Pro Asp Ser
                165                 170                 175

Ser Pro Ala Leu Ala Thr Ile Asp Ala Tyr Arg Arg Tyr Leu Asp Thr
            180                 185                 190

Leu Ala Asp Ala Tyr Pro Val Leu Glu Trp Gly Leu Arg Trp Cys Glu
            195                 200                 205

Leu His Ala Pro Arg Ser Ser Thr Leu Cys Leu Leu His Arg Asp Tyr
            210                 215                 220

Arg Thr Gly Asn Tyr Leu Ala Ser Glu Glu Gly Leu Glu Ala Val Leu
225                 230                 235                 240

Asp Trp Glu Phe Thr Gly Trp Gly Asp Pro Cys Glu Asp Leu Gly Trp
                245                 250                 255

Phe Thr Ala Arg Cys Trp Arg Phe Thr Arg Pro Asp Leu Glu Ala Gly
            260                 265                 270

Gly Ile Gly Gln Leu Glu Asp Phe Leu Arg Gly Tyr His Glu Val Ser
            275                 280                 285

Ser Leu Cys Ile Glu Arg Ser Arg Leu His Tyr Trp Gln Val Met Ala
290                 295                 300

Thr Leu Arg Trp Ala Val Ile Ala Leu Gln Gln Gly Gln Arg His Leu
305                 310                 315                 320

Ser Gly Glu Glu Pro Ser Leu Glu Leu Ala Leu Thr Ala Arg Leu Leu
                325                 330                 335

Pro Glu Leu Glu Leu Asp Ile Leu His Met Thr Gly Ala Glu Ala Pro
            340                 345                 350
```

<210> SEQ ID NO 3
<211> LENGTH: 357
<212> TYPE: DNA
<213> ORGANISM: Pseudomonas putida
<220> FEATURE:
<221> NAME/KEY: CDS
<222> LOCATION: (1)..(357)

<400> SEQUENCE: 3

```
atg acc caa ccc aac gcc cac gaa ttg ctc gag atc gcc cgc gcg acg    48
Met Thr Gln Pro Asn Ala His Glu Leu Leu Glu Ile Ala Arg Ala Thr
1               5                   10                  15 ctt ctg gag cag ctg ctg cca gcg ctg ccc ggc gag ttg cgt tac ccg    96
Leu Leu Glu Gln Leu Leu Pro Ala Leu Pro Gly Glu Leu Arg Tyr Pro
                20                  25                  30 gcc ctg atg atc gcc aac gcc atg gcc att gcg gcc cgc gaa aac cgc   144
Ala Leu Met Ile Ala Asn Ala Met Ala Ile Ala Ala Arg Glu Asn Arg
            35                  40                  45 ttg ggc gct cag gcc gag gat cag gag cag gcg cgt ctg gcc gcc ttg   192
Leu Gly Ala Gln Ala Glu Asp Gln Glu Gln Ala Arg Leu Ala Ala Leu
        50                  55                  60 gtc gat gac gcg ccg tcg aca ttg ccc gac ctg cgc cgc caa ctg gct   240
Val Asp Asp Ala Pro Ser Thr Leu Pro Asp Leu Arg Arg Gln Leu Ala
```

```
                 65                  70                  75                  80 cgc gcc att cgc cag ggc agc cat gac gcc ccg caa acc cgg cgc acc        288
Arg Ala Ile Arg Gln Gly Ser His Asp Ala Pro Gln Thr Arg Arg Thr
                 85                  90                  95 ctg gtc gag aca tta cgc cag atc acc gtt gcc cga ttg gcg atc agc        336
Leu Val Glu Thr Leu Arg Gln Ile Thr Val Ala Arg Leu Ala Ile Ser
                100                 105                 110 aac ccc aag gcc ttg ccc tga                                            357
Asn Pro Lys Ala Leu Pro
        115

<210> SEQ ID NO 4
<211> LENGTH: 118
<212> TYPE: PRT
<213> ORGANISM: Pseudomonas putida

<400> SEQUENCE: 4

Met Thr Gln Pro Asn Ala His Glu Leu Leu Glu Ile Ala Arg Ala Thr
1               5                   10                  15

Leu Leu Glu Gln Leu Leu Pro Ala Leu Pro Gly Glu Leu Arg Tyr Pro
                20                  25                  30

Ala Leu Met Ile Ala Asn Ala Met Ala Ile Ala Ala Arg Glu Asn Arg
            35                  40                  45

Leu Gly Ala Gln Ala Glu Asp Gln Gln Ala Arg Leu Ala Ala Leu
        50                  55                  60

Val Asp Asp Ala Pro Ser Thr Leu Pro Asp Leu Arg Arg Gln Leu Ala
65                  70                  75                  80

Arg Ala Ile Arg Gln Gly Ser His Asp Ala Pro Gln Thr Arg Arg Thr
                85                  90                  95

Leu Val Glu Thr Leu Arg Gln Ile Thr Val Ala Arg Leu Ala Ile Ser
                100                 105                 110

Asn Pro Lys Ala Leu Pro
        115

<210> SEQ ID NO 5
<211> LENGTH: 1173
<212> TYPE: DNA
<213> ORGANISM: Pseudomonas putida
<220> FEATURE:
<221> NAME/KEY: CDS
<222> LOCATION: (1)..(1173)

<400> SEQUENCE: 5 atg aac ttc act ctc ccg gac gaa ctg ctc gcc ttg cag gcc aag act        48
Met Asn Phe Thr Leu Pro Asp Glu Leu Leu Ala Leu Gln Ala Lys Thr
1               5                   10                  15 cga gac ttc att gcc gaa cag gtc atc cca ttc gag aac gac ccc cgc        96
Arg Asp Phe Ile Ala Glu Gln Val Ile Pro Phe Glu Asn Asp Pro Arg
                20                  25                  30 cag aac agc cac ggc ccc agc gac gca ctg cgc cag gac ctg gtg ctc       144
Gln Asn Ser His Gly Pro Ser Asp Ala Leu Arg Gln Asp Leu Val Leu
            35                  40                  45 tgc gcc cgc gcc gct ggc ttg ctg acg cct cac gcc agc cgc gaa atg       192
Cys Ala Arg Ala Ala Gly Leu Leu Thr Pro His Ala Ser Arg Glu Met
        50                  55                  60 ggc ggt ctg gaa ctg agc cat gtg gcc aag gcg atc gtc ttc gaa gaa       240
Gly Gly Leu Glu Leu Ser His Val Ala Lys Ala Ile Val Phe Glu Glu
65                  70                  75                  80 gcc ggc tac tcg ccg ctg ggc ccg gta gcg ctg aat atc cat gcg ccg       288
Ala Gly Tyr Ser Pro Leu Gly Pro Val Ala Leu Asn Ile His Ala Pro
```

```
                        85                  90                  95
gac gaa ggc aat atc cac ctg atg gac gtg gtc gcc acc gaa gcg cag      336
Asp Glu Gly Asn Ile His Leu Met Asp Val Val Ala Thr Glu Ala Gln
                100                 105                 110 aag gac cgc tgg ttg cgc ccg ctg gtc cag ggc cat gcc cgt tcg tgc      384
Lys Asp Arg Trp Leu Arg Pro Leu Val Gln Gly His Ala Arg Ser Cys
            115                 120                 125 ttc gcc atg acg gag cct gct ccg ggc tcc ggt tcg gat ccg tcg atg      432
Phe Ala Met Thr Glu Pro Ala Pro Gly Ser Gly Ser Asp Pro Ser Met
130                 135                 140 ctg cgc acc act gcc acc cgc gat ggc gac gac tac ctg atc aat ggt      480
Leu Arg Thr Thr Ala Thr Arg Asp Gly Asp Asp Tyr Leu Ile Asn Gly
145                 150                 155                 160 cgc aag tgg ctg atc acc ggg gcc gaa ggc gcg gac ttc ggc atc atc      528
Arg Lys Trp Leu Ile Thr Gly Ala Glu Gly Ala Asp Phe Gly Ile Ile
                165                 170                 175 atg gcg cgc atg gag gac ggc acc gcg acc atg ttc ctg acc gac atg      576
Met Ala Arg Met Glu Asp Gly Thr Ala Thr Met Phe Leu Thr Asp Met
            180                 185                 190 aag cgc gac ggc atc atc cat gaa cgt cag ctg gac tcg ctg gac agc      624
Lys Arg Asp Gly Ile Ile His Glu Arg Gln Leu Asp Ser Leu Asp Ser
        195                 200                 205 tgt ttt acc ggc ggt cac ggg cag ctg cgt ttc gac aac ctg cgt att      672
Cys Phe Thr Gly Gly His Gly Gln Leu Arg Phe Asp Asn Leu Arg Ile
210                 215                 220 ccg gcg agc gat gtc ctc ggc gag atc ggc aag ggc ttc cgg tat gcc      720
Pro Ala Ser Asp Val Leu Gly Glu Ile Gly Lys Gly Phe Arg Tyr Ala
225                 230                 235                 240 cag gtg cgc ctg gcg cct gca cgc ttg act cat tgc atg cgc tgg ctc      768
Gln Val Arg Leu Ala Pro Ala Arg Leu Thr His Cys Met Arg Trp Leu
                245                 250                 255 ggt gcc gcg cgc cgc gcc cac gac atc gcc tgc gac tat gcg cgc acc      816
Gly Ala Ala Arg Arg Ala His Asp Ile Ala Cys Asp Tyr Ala Arg Thr
            260                 265                 270 cgg gac gcc ttt ggc aag ccg ctg ggc gag cac cag ggc gtg ggt ttc      864
Arg Asp Ala Phe Gly Lys Pro Leu Gly Glu His Gln Gly Val Gly Phe
        275                 280                 285 atg ctg gcc gac aac atg atg gac ctg cac gtg gtg cgt ctg gcg gtc      912
Met Leu Ala Asp Asn Met Met Asp Leu His Val Val Arg Leu Ala Val
290                 295                 300 tgg cac tgc gcc tgg gtg ctc gac cag ggc cgg cgc gcc aat gtc gat      960
Trp His Cys Ala Trp Val Leu Asp Gln Gly Arg Arg Ala Asn Val Asp
305                 310                 315                 320 tcg agc atg gcc aag gtg atc agc gcc gag gcg ctg tgg cgg gtg gtc     1008
Ser Ser Met Ala Lys Val Ile Ser Ala Glu Ala Leu Trp Arg Val Val
                325                 330                 335 gat cgt tgc gtc cag gta ttg ggt gga cgc ggg gtg acc ggg gac acc     1056
Asp Arg Cys Val Gln Val Leu Gly Gly Arg Gly Val Thr Gly Asp Thr
            340                 345                 350 gtg gtg gag cgg atc ttc cgc gac att cgc ccg ttc cgc atc tat gac     1104
Val Val Glu Arg Ile Phe Arg Asp Ile Arg Pro Phe Arg Ile Tyr Asp
        355                 360                 365 ggc ccg agc gaa gtg cac cgc atg agc ctg gcg aag aag ctg ctc gac     1152
Gly Pro Ser Glu Val His Arg Met Ser Leu Ala Lys Lys Leu Leu Asp
370                 375                 380 cag cgc ctg gag gcc cac tga                                         1173
Gln Arg Leu Glu Ala His
385                 390
```

<210> SEQ ID NO 6
<211> LENGTH: 390
<212> TYPE: PRT
<213> ORGANISM: Pseudomonas putida

<400> SEQUENCE: 6

```
Met Asn Phe Thr Leu Pro Asp Glu Leu Ala Leu Gln Ala Lys Thr
1               5                   10                  15

Arg Asp Phe Ile Ala Glu Gln Val Ile Pro Phe Glu Asn Asp Pro Arg
            20                  25                  30

Gln Asn Ser His Gly Pro Ser Asp Ala Leu Arg Gln Asp Leu Val Leu
        35                  40                  45

Cys Ala Arg Ala Ala Gly Leu Leu Thr Pro His Ala Ser Arg Glu Met
50                  55                  60

Gly Gly Leu Glu Leu Ser His Val Ala Lys Ala Ile Val Phe Glu Glu
65                  70                  75                  80

Ala Gly Tyr Ser Pro Leu Gly Pro Val Ala Leu Asn Ile His Ala Pro
                85                  90                  95

Asp Glu Gly Asn Ile His Leu Met Asp Val Val Ala Thr Glu Ala Gln
            100                 105                 110

Lys Asp Arg Trp Leu Arg Pro Leu Val Gln Gly His Ala Arg Ser Cys
        115                 120                 125

Phe Ala Met Thr Glu Pro Ala Pro Gly Ser Gly Ser Asp Pro Ser Met
130                 135                 140

Leu Arg Thr Thr Ala Thr Arg Asp Gly Asp Asp Tyr Leu Ile Asn Gly
145                 150                 155                 160

Arg Lys Trp Leu Ile Thr Gly Ala Glu Gly Ala Asp Phe Gly Ile Ile
                165                 170                 175

Met Ala Arg Met Glu Asp Gly Thr Ala Thr Met Phe Leu Thr Asp Met
            180                 185                 190

Lys Arg Asp Gly Ile Ile His Glu Arg Gln Leu Asp Ser Leu Asp Ser
        195                 200                 205

Cys Phe Thr Gly Gly His Gly Gln Leu Arg Phe Asp Asn Leu Arg Ile
210                 215                 220

Pro Ala Ser Asp Val Leu Gly Glu Ile Gly Lys Gly Phe Arg Tyr Ala
225                 230                 235                 240

Gln Val Arg Leu Ala Pro Ala Arg Leu Thr His Cys Met Arg Trp Leu
                245                 250                 255

Gly Ala Ala Arg Arg Ala His Asp Ile Ala Cys Asp Tyr Ala Arg Thr
            260                 265                 270

Arg Asp Ala Phe Gly Lys Pro Leu Gly Glu His Gln Gly Val Gly Phe
        275                 280                 285

Met Leu Ala Asp Asn Met Met Asp Leu His Val Val Arg Leu Ala Val
290                 295                 300

Trp His Cys Ala Trp Val Leu Asp Gln Gly Arg Arg Ala Asn Val Asp
305                 310                 315                 320

Ser Ser Met Ala Lys Val Ile Ser Ala Glu Ala Leu Trp Arg Val Val
                325                 330                 335

Asp Arg Cys Val Gln Val Leu Gly Gly Arg Gly Val Thr Gly Asp Thr
            340                 345                 350

Val Val Glu Arg Ile Phe Arg Asp Ile Arg Pro Phe Arg Ile Tyr Asp
        355                 360                 365

Gly Pro Ser Glu Val His Arg Met Ser Leu Ala Lys Lys Leu Leu Asp
370                 375                 380
```

Gln Arg Leu Glu Ala His
385                390

<210> SEQ ID NO 7
<211> LENGTH: 768
<212> TYPE: DNA
<213> ORGANISM: Pseudomonas putida
<220> FEATURE:
<221> NAME/KEY: CDS
<222> LOCATION: (1)..(768)

<400> SEQUENCE: 7

| | | | | | | | | | | | | | | | | |
|---|---|---|---|---|---|---|---|---|---|---|---|---|---|---|---|---|
| atg | cag | ccg | aac | ctt | gcc | cga | ctg | ttc | gcc | ctc | gac | ggg | cgt | cgc | gcc | 48 |
| Met | Gln | Pro | Asn | Leu | Ala | Arg | Leu | Phe | Ala | Leu | Asp | Gly | Arg | Arg | Ala | |
| 1 | | | | 5 | | | | | 10 | | | | | 15 | | |
| ctg | gtg | acc | ggg | gcc | tcc | agc | ggc | ctg | ggc | cgt | cac | ttc | gcc | atg | acc | 96 |
| Leu | Val | Thr | Gly | Ala | Ser | Ser | Gly | Leu | Gly | Arg | His | Phe | Ala | Met | Thr | |
| | | | 20 | | | | | 25 | | | | | 30 | | | |
| ctg | gcc | gcc | gca | ggc | gcc | gag | gtg | gtg | gtg | acc | gcc | aga | cgc | cag | gcg | 144 |
| Leu | Ala | Ala | Ala | Gly | Ala | Glu | Val | Val | Val | Thr | Ala | Arg | Arg | Gln | Ala | |
| | | | | 35 | | | | | 40 | | | | | 45 | | |
| ccg | ctg | cag | gcg | ttg | gtg | gag | gcc | atc | gag | gtg | gcc | gga | ggg | cgg | gcg | 192 |
| Pro | Leu | Gln | Ala | Leu | Val | Glu | Ala | Ile | Glu | Val | Ala | Gly | Gly | Arg | Ala | |
| | | 50 | | | | | 55 | | | | | 60 | | | | |
| cag | gcc | ttt | gcc | ctc | gat | gtg | acg | agc | cgt | gag | gac | atc | tgc | cgg | gtg | 240 |
| Gln | Ala | Phe | Ala | Leu | Asp | Val | Thr | Ser | Arg | Glu | Asp | Ile | Cys | Arg | Val | |
| 65 | | | | | 70 | | | | | 75 | | | | | 80 | |
| ctc | gat | gcc | gcc | ggc | ccg | ctg | gat | gtt | ctg | gtc | aac | aat | gcg | ggg | gtg | 288 |
| Leu | Asp | Ala | Ala | Gly | Pro | Leu | Asp | Val | Leu | Val | Asn | Asn | Ala | Gly | Val | |
| | | | | 85 | | | | | 90 | | | | | 95 | | |
| agc | gac | agc | cag | cct | ttg | cta | gcc | tgc | gat | gat | caa | acc | tgg | gac | cac | 336 |
| Ser | Asp | Ser | Gln | Pro | Leu | Leu | Ala | Cys | Asp | Asp | Gln | Thr | Trp | Asp | His | |
| | | | 100 | | | | | 105 | | | | | 110 | | | |
| gtg | ctc | gac | acc | aac | ctc | aag | ggc | gcc | tgg | gcc | gtg | gcc | cag | gaa | agc | 384 |
| Val | Leu | Asp | Thr | Asn | Leu | Lys | Gly | Ala | Trp | Ala | Val | Ala | Gln | Glu | Ser | |
| | | | | 115 | | | | | 120 | | | | | 125 | | |
| gcc | cgg | cgc | atg | gtg | gtg | gcg | ggg | aag | ggg | ggc | agc | ctg | atc | aat | gtc | 432 |
| Ala | Arg | Arg | Met | Val | Val | Ala | Gly | Lys | Gly | Gly | Ser | Leu | Ile | Asn | Val | |
| | | 130 | | | | | 135 | | | | | 140 | | | | |
| acc | tcg | atc | ctc | gcc | agc | cgt | gtg | gcc | ggc | gcc | gtc | ggc | cct | tac | ctg | 480 |
| Thr | Ser | Ile | Leu | Ala | Ser | Arg | Val | Ala | Gly | Ala | Val | Gly | Pro | Tyr | Leu | |
| 145 | | | | | 150 | | | | | 155 | | | | | 160 | |
| gcg | gcc | aag | gcc | ggc | ctg | gcc | cac | ctg | acc | cgc | gcc | atg | gcg | ctg | gag | 528 |
| Ala | Ala | Lys | Ala | Gly | Leu | Ala | His | Leu | Thr | Arg | Ala | Met | Ala | Leu | Glu | |
| | | | | 165 | | | | | 170 | | | | | 175 | | |
| ttg | gcg | cgc | cat | ggt | atc | cgg | gtg | aac | gcc | ctg | gcg | ccc | ggc | tac | gtg | 576 |
| Leu | Ala | Arg | His | Gly | Ile | Arg | Val | Asn | Ala | Leu | Ala | Pro | Gly | Tyr | Val | |
| | | | 180 | | | | | 185 | | | | | 190 | | | |
| atg | act | gat | ttg | aac | gag | gcc | ttc | ctg | gcc | agc | gag | gcc | ggt | gac | aag | 624 |
| Met | Thr | Asp | Leu | Asn | Glu | Ala | Phe | Leu | Ala | Ser | Glu | Ala | Gly | Asp | Lys | |
| | | | | 195 | | | | | 200 | | | | | 205 | | |
| ttg | cgc | tcg | cgg | atc | ccc | agc | cgc | cgc | ttc | agc | gtg | ccg | tcg | gac | ctg | 672 |
| Leu | Arg | Ser | Arg | Ile | Pro | Ser | Arg | Arg | Phe | Ser | Val | Pro | Ser | Asp | Leu | |
| | | 210 | | | | | 215 | | | | | 220 | | | | |
| gac | ggc | gcc | ttg | ctg | ctc | ctc | gcc | agc | gat | gcc | ggg | cgg | gcg | atg | agc | 720 |
| Asp | Gly | Ala | Leu | Leu | Leu | Leu | Ala | Ser | Asp | Ala | Gly | Arg | Ala | Met | Ser | |
| 225 | | | | | 230 | | | | | 235 | | | | | 240 | |
| ggc | gct | gag | atc | gtg | gtc | gat | ggc | ggc | cac | ctg | tgc | agc | agc | ctg | taa | 768 |
| Gly | Ala | Glu | Ile | Val | Val | Asp | Gly | Gly | His | Leu | Cys | Ser | Ser | Leu | | |
| | | | | 245 | | | | | 250 | | | | | 255 | | |

<210> SEQ ID NO 8
<211> LENGTH: 255
<212> TYPE: PRT
<213> ORGANISM: Pseudomonas putida

<400> SEQUENCE: 8

```
Met Gln Pro Asn Leu Ala Arg Leu Phe Ala Leu Asp Gly Arg Arg Ala
1               5                   10                  15

Leu Val Thr Gly Ala Ser Ser Gly Leu Gly Arg His Phe Ala Met Thr
            20                  25                  30

Leu Ala Ala Ala Gly Ala Glu Val Val Thr Ala Arg Arg Gln Ala
        35                  40                  45

Pro Leu Gln Ala Leu Val Glu Ala Ile Glu Val Ala Gly Gly Arg Ala
    50                  55                  60

Gln Ala Phe Ala Leu Asp Val Thr Ser Arg Glu Asp Ile Cys Arg Val
65                  70                  75                  80

Leu Asp Ala Ala Gly Pro Leu Asp Val Leu Asn Asn Ala Gly Val
                85                  90                  95

Ser Asp Ser Gln Pro Leu Leu Ala Cys Asp Asp Gln Thr Trp Asp His
                100                 105                 110

Val Leu Asp Thr Asn Leu Lys Gly Ala Trp Ala Val Ala Gln Glu Ser
            115                 120                 125

Ala Arg Arg Met Val Val Ala Gly Lys Gly Gly Ser Leu Ile Asn Val
        130                 135                 140

Thr Ser Ile Leu Ala Ser Arg Val Ala Gly Ala Val Gly Pro Tyr Leu
145                 150                 155                 160

Ala Ala Lys Ala Gly Leu Ala His Leu Thr Arg Ala Met Ala Leu Glu
                165                 170                 175

Leu Ala Arg His Gly Ile Arg Val Asn Ala Leu Ala Pro Gly Tyr Val
            180                 185                 190

Met Thr Asp Leu Asn Glu Ala Phe Leu Ala Ser Glu Ala Gly Asp Lys
        195                 200                 205

Leu Arg Ser Arg Ile Pro Ser Arg Arg Phe Ser Val Pro Ser Asp Leu
    210                 215                 220

Asp Gly Ala Leu Leu Leu Ala Ser Asp Ala Gly Arg Ala Met Ser
225                 230                 235                 240

Gly Ala Glu Ile Val Val Asp Gly Gly His Leu Cys Ser Ser Leu
                245                 250                 255
```

<210> SEQ ID NO 9
<211> LENGTH: 1647
<212> TYPE: DNA
<213> ORGANISM: Pseudomonas putida
<220> FEATURE:
<221> NAME/KEY: CDS
<222> LOCATION: (1)..(1647)

<400> SEQUENCE: 9

```
atg atg gtt cca acc ctc gaa cac gag ctt gct ccc aac gaa gcc aac     48
Met Met Val Pro Thr Leu Glu His Glu Leu Ala Pro Asn Glu Ala Asn
1               5                   10                  15 cat gtc ccg ctg tcg ccg ctg tcg ttc ctc aag cgt gcc gcg cag gtg     96
His Val Pro Leu Ser Pro Leu Ser Phe Leu Lys Arg Ala Ala Gln Val
            20                  25                  30 tac ccg cag cgc gat gcg gtg atc tat ggc gca agg cgc tac agc tac    144
Tyr Pro Gln Arg Asp Ala Val Ile Tyr Gly Ala Arg Arg Tyr Ser Tyr
        35                  40                  45 cgt cag ttg cac gag cgc agc cgc gcc ctg gcc agt gcc ttg gag cgg    192
```

```
Arg Gln Leu His Glu Arg Ser Arg Ala Leu Ala Ser Ala Leu Glu Arg
    50                  55                  60 gtc ggt gtt cag ccg ggc gag cgg gtg gcg ata ttg gcg ccg aac atc      240
Val Gly Val Gln Pro Gly Glu Arg Val Ala Ile Leu Ala Pro Asn Ile
 65                  70                  75                  80 ccg gaa atg ctc gag gcc cac tat ggc gtg ccc ggt gcc ggg gcg gtg      288
Pro Glu Met Leu Glu Ala His Tyr Gly Val Pro Gly Ala Gly Ala Val
                     85                  90                  95 ctg gtg tgc atc aac atc cgc ctg gag ggg cgc agc att gcc ttc atc      336
Leu Val Cys Ile Asn Ile Arg Leu Glu Gly Arg Ser Ile Ala Phe Ile
                100                 105                 110 ctg cgt cac tgc gcg gcc aag gta ttg atc tgc gat cgt gag ttc ggt      384
Leu Arg His Cys Ala Ala Lys Val Leu Ile Cys Asp Arg Glu Phe Gly
            115                 120                 125 gcc gtg gcc aat cag gcg ctg gcc atg ctc gat gcg ccg ccc ttg ctg      432
Ala Val Ala Asn Gln Ala Leu Ala Met Leu Asp Ala Pro Pro Leu Leu
        130                 135                 140 gtg ggc atc gac gat gat cag gcc gag cgc gcc gat ttg gcc cac gac      480
Val Gly Ile Asp Asp Asp Gln Ala Glu Arg Ala Asp Leu Ala His Asp
145                 150                 155                 160 ctg gac tac gaa gcg ttc ttg gcc cag ggc gac ccc gcg cgg ccg ttg      528
Leu Asp Tyr Glu Ala Phe Leu Ala Gln Gly Asp Pro Ala Arg Pro Leu
                165                 170                 175 agt gcg cca cag aac gaa tgg cag tcg atc gcc atc aac tac acc tcc      576
Ser Ala Pro Gln Asn Glu Trp Gln Ser Ile Ala Ile Asn Tyr Thr Ser
                180                 185                 190 ggc acc acg ggg gac ccc aag ggc gtg gtg ctg cat cac cgc ggc gcc      624
Gly Thr Thr Gly Asp Pro Lys Gly Val Val Leu His His Arg Gly Ala
            195                 200                 205 tac ctc aac gcc tgc gcc ggg gcg ctg atc ttc cag ttg ggg ccg cgc      672
Tyr Leu Asn Ala Cys Ala Gly Ala Leu Ile Phe Gln Leu Gly Pro Arg
        210                 215                 220 agc gtc tac ttg tgg acc ttg ccg atg ttc cac tgc aac ggc tgg agc      720
Ser Val Tyr Leu Trp Thr Leu Pro Met Phe His Cys Asn Gly Trp Ser
225                 230                 235                 240 cat acc tgg gcg gtg acg ttg tcc ggt ggc acc cac gtg tgt ctg cgc      768
His Thr Trp Ala Val Thr Leu Ser Gly Gly Thr His Val Cys Leu Arg
                245                 250                 255 aag gtc cag cct gat gcg atc aac gcc gcc atc gcc gag cat gcc gtg      816
Lys Val Gln Pro Asp Ala Ile Asn Ala Ala Ile Ala Glu His Ala Val
                260                 265                 270 act cac ctg agc gcc gcc cca gtg gtg atg tcg atg ctg atc cac gcc      864
Thr His Leu Ser Ala Ala Pro Val Val Met Ser Met Leu Ile His Ala
            275                 280                 285 gag cat gcc agc gcc cct ccg gtg ccg gtt tcg gtg atc act ggc ggt      912
Glu His Ala Ser Ala Pro Pro Val Pro Val Ser Val Ile Thr Gly Gly
        290                 295                 300 gcc gcc ccg ccc agt gcg gtc atc gcg gcg atg gag gcg cgt ggc ttc      960
Ala Ala Pro Pro Ser Ala Val Ile Ala Ala Met Glu Ala Arg Gly Phe
305                 310                 315                 320 aac atc acc cat gcc tat ggc atg acc gaa agc tac ggt ccc agc aca     1008
Asn Ile Thr His Ala Tyr Gly Met Thr Glu Ser Tyr Gly Pro Ser Thr
                325                 330                 335 ttg tgc ctg tgg cag ccg ggt gtc gac gag ttg ccg ctg gag gcc cgg     1056
Leu Cys Leu Trp Gln Pro Gly Val Asp Glu Leu Pro Leu Glu Ala Arg
                340                 345                 350 gcc cag ttc atg agc cgc cag ggc gtc gcc cac ccg ctg ctc gag gag     1104
Ala Gln Phe Met Ser Arg Gln Gly Val Ala His Pro Leu Leu Glu Glu
            355                 360                 365
```

```
gcc acg gtg ctg gat acc gac acc ggc cgc ccg gtc ccg gcc gac ggc    1152
Ala Thr Val Leu Asp Thr Asp Thr Gly Arg Pro Val Pro Ala Asp Gly
370                 375                 380 ctt acc ctc ggc gag ctg gtg gtg cgg ggc aac act gtg atg aaa ggc    1200
Leu Thr Leu Gly Glu Leu Val Val Arg Gly Asn Thr Val Met Lys Gly
385                 390                 395                 400 tac ctg cac aac cca gag gct acc cgt gcc gcg ttg gcc aac ggc tgg    1248
Tyr Leu His Asn Pro Glu Ala Thr Arg Ala Ala Leu Ala Asn Gly Trp
            405                 410                 415 ctg cac acg ggc gac ctg gcc gtg ctg cac ctg gac ggc tat gtg gaa    1296
Leu His Thr Gly Asp Leu Ala Val Leu His Leu Asp Gly Tyr Val Glu
420                 425                 430 atc aag gac cga gcc aag gac atc atc att tct ggc ggc gag aac atc    1344
Ile Lys Asp Arg Ala Lys Asp Ile Ile Ile Ser Gly Gly Glu Asn Ile
435                 440                 445 agt tcg ctg gag ata gaa gaa gtg ctc tac cag cac ccc gag gtg gtc    1392
Ser Ser Leu Glu Ile Glu Glu Val Leu Tyr Gln His Pro Glu Val Val
    450                 455                 460 gag gct gcg gtg gtg gcg cgt ccg gat tcg cgc tgg ggc gag aca cct    1440
Glu Ala Ala Val Val Ala Arg Pro Asp Ser Arg Trp Gly Glu Thr Pro
465                 470                 475                 480 cac gct ttc gtc acg ctg cgc gct gat gca ctg gcc agc ggg gac gac    1488
His Ala Phe Val Thr Leu Arg Ala Asp Ala Leu Ala Ser Gly Asp Asp
                485                 490                 495 ctg gtc cgc tgg tgc cgt gag cgt ctg gcg cac ttc aag gcg ccg cgc    1536
Leu Val Arg Trp Cys Arg Glu Arg Leu Ala His Phe Lys Ala Pro Arg
            500                 505                 510 cat gtg tcg ctc gtg gac ctg ccc aag acc gcc act gga aaa ata cag    1584
His Val Ser Leu Val Asp Leu Pro Lys Thr Ala Thr Gly Lys Ile Gln
515                 520                 525 aag ttc gtc ctg cgt gag tgg gcc cgg caa cag gag gcg cag atc gcc    1632
Lys Phe Val Leu Arg Glu Trp Ala Arg Gln Gln Glu Ala Gln Ile Ala
530                 535                 540 gac gcc gag cat tga                                                1647
Asp Ala Glu His
545

<210> SEQ ID NO 10
<211> LENGTH: 548
<212> TYPE: PRT
<213> ORGANISM: Pseudomonas putida

<400> SEQUENCE: 10

Met Met Val Pro Thr Leu Glu His Glu Leu Ala Pro Asn Glu Ala Asn
1               5                   10                  15

His Val Pro Leu Ser Pro Leu Ser Phe Leu Lys Arg Ala Ala Gln Val
            20                  25                  30

Tyr Pro Gln Arg Asp Ala Val Ile Tyr Gly Ala Arg Tyr Ser Tyr
        35                  40                  45

Arg Gln Leu His Glu Arg Ser Arg Ala Leu Ala Ser Ala Leu Glu Arg
    50                  55                  60

Val Gly Val Gln Pro Gly Glu Arg Val Ala Ile Leu Ala Pro Asn Ile
65                  70                  75                  80

Pro Glu Met Leu Glu Ala His Tyr Gly Val Pro Gly Ala Gly Ala Val
                85                  90                  95

Leu Val Cys Ile Asn Ile Arg Leu Glu Gly Arg Ser Ile Ala Phe Ile
            100                 105                 110

Leu Arg His Cys Ala Ala Lys Val Leu Ile Cys Asp Arg Glu Phe Gly
        115                 120                 125
```

-continued

```
Ala Val Ala Asn Gln Ala Leu Ala Met Leu Asp Ala Pro Leu Leu
    130                 135                 140
Val Gly Ile Asp Asp Gln Ala Glu Arg Ala Asp Leu Ala His Asp
145                 150                 155                 160
Leu Asp Tyr Glu Ala Phe Leu Ala Gln Gly Asp Pro Ala Arg Pro Leu
                165                 170                 175
Ser Ala Pro Gln Asn Glu Trp Gln Ser Ile Ala Ile Asn Tyr Thr Ser
            180                 185                 190
Gly Thr Thr Gly Asp Pro Lys Gly Val Val Leu His His Arg Gly Ala
        195                 200                 205
Tyr Leu Asn Ala Cys Ala Gly Ala Leu Ile Phe Gln Leu Gly Pro Arg
    210                 215                 220
Ser Val Tyr Leu Trp Thr Leu Pro Met Phe His Cys Asn Gly Trp Ser
225                 230                 235                 240
His Thr Trp Ala Val Thr Leu Ser Gly Gly Thr His Val Cys Leu Arg
                245                 250                 255
Lys Val Gln Pro Asp Ala Ile Asn Ala Ala Ile Ala Glu His Ala Val
            260                 265                 270
Thr His Leu Ser Ala Ala Pro Val Val Met Ser Met Leu Ile His Ala
        275                 280                 285
Glu His Ala Ser Ala Pro Pro Val Pro Val Ser Val Ile Thr Gly Gly
    290                 295                 300
Ala Ala Pro Pro Ser Ala Val Ile Ala Ala Met Glu Ala Arg Gly Phe
305                 310                 315                 320
Asn Ile Thr His Ala Tyr Gly Met Thr Glu Ser Tyr Gly Pro Ser Thr
                325                 330                 335
Leu Cys Leu Trp Gln Pro Gly Val Asp Glu Leu Pro Leu Glu Ala Arg
            340                 345                 350
Ala Gln Phe Met Ser Arg Gln Gly Val Ala His Pro Leu Leu Glu Glu
        355                 360                 365
Ala Thr Val Leu Asp Thr Asp Thr Gly Arg Pro Val Pro Ala Asp Gly
    370                 375                 380
Leu Thr Leu Gly Glu Leu Val Val Arg Gly Asn Thr Val Met Lys Gly
385                 390                 395                 400
Tyr Leu His Asn Pro Glu Ala Thr Arg Ala Ala Leu Ala Asn Gly Trp
                405                 410                 415
Leu His Thr Gly Asp Leu Ala Val Leu His Leu Asp Gly Tyr Val Glu
            420                 425                 430
Ile Lys Asp Arg Ala Lys Asp Ile Ile Ser Gly Gly Glu Asn Ile
        435                 440                 445
Ser Ser Leu Glu Ile Glu Glu Val Leu Tyr Gln His Pro Glu Val Val
    450                 455                 460
Glu Ala Ala Val Val Ala Arg Pro Asp Ser Arg Trp Gly Glu Thr Pro
465                 470                 475                 480
His Ala Phe Val Thr Leu Arg Ala Asp Ala Leu Ala Ser Gly Asp Asp
                485                 490                 495
Leu Val Arg Trp Cys Arg Glu Arg Leu Ala His Phe Lys Ala Pro Arg
            500                 505                 510
His Val Ser Leu Val Asp Leu Pro Lys Thr Ala Thr Gly Lys Ile Gln
        515                 520                 525
Lys Phe Val Leu Arg Glu Trp Ala Arg Gln Glu Ala Gln Ile Ala
    530                 535                 540
```

Asp Ala Glu His
545

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
aacctggacg gtgaagagcg                                                  20

<210> SEQ ID NO 12
<211> LENGTH: 19
<212> TYPE: DNA
<213> ORGANISM: Artificial Sequence
<220> FEATURE:
<223> OTHER INFORMATION: PCR Primer

<400> SEQUENCE: 12
gaacggacag gaagcacag                                                   19

<210> SEQ ID NO 13
<211> LENGTH: 32
<212> TYPE: DNA
<213> ORGANISM: Artificial Sequence
<220> FEATURE:
<223> OTHER INFORMATION: PCR Primer

<400> SEQUENCE: 13
ggccacgcgt cgactagtac cccccccccc cc                                    32

<210> SEQ ID NO 14
<211> LENGTH: 36
<212> TYPE: DNA
<213> ORGANISM: Artificial Sequence
<220> FEATURE:
<223> OTHER INFORMATION: PCR Primer

<400> SEQUENCE: 14
ggccacgcgt cgactagtac ggghhggghh ggghhg                                36

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
ccaatgcccg tagcaggtcg c                                                21

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
gaactcctgt tcacggtcaa g                                                21

<210> SEQ ID NO 17
<211> LENGTH: 19
<212> TYPE: DNA

```
<213> ORGANISM: Artificial Sequence
<220> FEATURE:
<223> OTHER INFORMATION: PCR Primer

<400> SEQUENCE: 17
tcaatgatcg acggcaccg                                                    19

<210> SEQ ID NO 18
<211> LENGTH: 21
<212> TYPE: DNA
<213> ORGANISM: Artificial Sequence
<220> FEATURE:
<223> OTHER INFORMATION: PCR Primer

<400> SEQUENCE: 18
acgctgtgct tcctgtccgt t                                                 21

<210> SEQ ID NO 19
<211> LENGTH: 20
<212> TYPE: DNA
<213> ORGANISM: Artificial Sequence
<220> FEATURE:
<223> OTHER INFORMATION: PCR Primer

<400> SEQUENCE: 19
gttcttcacc ggacagatgg                                                   20

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
cccacgaatt gctcgagatc                                                   20

<210> SEQ ID NO 21
<211> LENGTH: 18
<212> TYPE: DNA
<213> ORGANISM: Artificial Sequence
<220> FEATURE:
<223> OTHER INFORMATION: PCR Primer

<400> SEQUENCE: 21
gcaggtcggg caatgtcg                                                     18

<210> SEQ ID NO 22
<211> LENGTH: 18
<212> TYPE: DNA
<213> ORGANISM: Artificial Sequence
<220> FEATURE:
<223> OTHER INFORMATION: PCR Primer

<400> SEQUENCE: 22
catgcccgtt cgtgcttc                                                     18

<210> SEQ ID NO 23
<211> LENGTH: 21
<212> TYPE: DNA
<213> ORGANISM: Artificial Sequence
<220> FEATURE:
<223> OTHER INFORMATION: PCR Primer

<400> SEQUENCE: 23
caggtccatc atgttgtcgg c                                                 21
```

<210> SEQ ID NO 24
<211> LENGTH: 19
<212> TYPE: DNA
<213> ORGANISM: Artificial Sequence
<220> FEATURE:
<223> OTHER INFORMATION: PCR Primer

<400> SEQUENCE: 24
acgagccgtg aggacatct                                                19

<210> SEQ ID NO 25
<211> LENGTH: 18
<212> TYPE: DNA
<213> ORGANISM: Artificial Sequence
<220> FEATURE:
<223> OTHER INFORMATION: PCR Primer

<400> SEQUENCE: 25
cgagcgcaac ttgtcacc                                                 18

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
gctggtgtgc atcaacatcc                                               20

<210> SEQ ID NO 27
<211> LENGTH: 20
<212> TYPE: DNA
<213> ORGANISM: Artificial Sequence
<220> FEATURE:
<223> OTHER INFORMATION: PCR Primer

<400> SEQUENCE: 27
gcagtggaac atcggcaagg                                               20

<210> SEQ ID NO 28
<211> LENGTH: 19
<212> TYPE: DNA
<213> ORGANISM: Artificial Sequence
<220> FEATURE:
<223> OTHER INFORMATION: PCR Primer

<400> SEQUENCE: 28
tgttatacgc gcgtgttcg                                                19

<210> SEQ ID NO 29
<211> LENGTH: 20
<212> TYPE: DNA
<213> ORGANISM: Artificial Sequence
<220> FEATURE:
<223> OTHER INFORMATION: PCR Primer

<400> SEQUENCE: 29
ggtacacgta gaacgccgac                                               20

<210> SEQ ID NO 30
<211> LENGTH: 22
<212> TYPE: DNA
<213> ORGANISM: Artificial Sequence
<220> FEATURE:

<223> OTHER INFORMATION: PCR Primer

<400> SEQUENCE: 30
catggtgttc gtgctgttca cc                                    22

<210> SEQ ID NO 31
<211> LENGTH: 20
<212> TYPE: DNA
<213> ORGANISM: Artificial Sequence
<220> FEATURE:
<223> OTHER INFORMATION: PCR Primer

<400> SEQUENCE: 31
gccgaacagc aacctgatca                                       20

<210> SEQ ID NO 32
<211> LENGTH: 21
<212> TYPE: DNA
<213> ORGANISM: Artificial Sequence
<220> FEATURE:
<223> OTHER INFORMATION: PCR Primer

<400> SEQUENCE: 32
acgctgtgct tcctgtccgt t                                     21

<210> SEQ ID NO 33
<211> LENGTH: 17
<212> TYPE: DNA
<213> ORGANISM: Artificial Sequence
<220> FEATURE:
<223> OTHER INFORMATION: PCR Primer

<400> SEQUENCE: 33
caggtcgggc aatgtcg                                          17

<210> SEQ ID NO 34
<211> LENGTH: 20
<212> TYPE: DNA
<213> ORGANISM: Artificial Sequence
<220> FEATURE:
<223> OTHER INFORMATION: PCR Primer

<400> SEQUENCE: 34
cccacgaatt gctcgagatc                                       20

<210> SEQ ID NO 35
<211> LENGTH: 19
<212> TYPE: DNA
<213> ORGANISM: Artificial Sequence
<220> FEATURE:
<223> OTHER INFORMATION: PCR Primer

<400> SEQUENCE: 35
gaagcacgaa cgggcatgg                                        19

<210> SEQ ID NO 36
<211> LENGTH: 21
<212> TYPE: DNA
<213> ORGANISM: Artificial Sequence
<220> FEATURE:
<223> OTHER INFORMATION: PCR Primer

<400> SEQUENCE: 36
gccgacaaca tgatggacct g                                     21

```
<210> SEQ ID NO 37
<211> LENGTH: 22
<212> TYPE: DNA
<213> ORGANISM: Artificial Sequence
<220> FEATURE:
<223> OTHER INFORMATION: PCR Primer

<400> SEQUENCE: 37
cgtggtccca ggtttgatca tc                                              22

<210> SEQ ID NO 38
<211> LENGTH: 20
<212> TYPE: DNA
<213> ORGANISM: Artificial Sequence
<220> FEATURE:
<223> OTHER INFORMATION: PCR Primer

<400> SEQUENCE: 38
gctcgacacc aacctcaagg                                                 20

<210> SEQ ID NO 39
<211> LENGTH: 20
<212> TYPE: DNA
<213> ORGANISM: Artificial Sequence
<220> FEATURE:
<223> OTHER INFORMATION: PCR Primer

<400> SEQUENCE: 39
gccaagaacg cttcgtagtc                                                 20

<210> SEQ ID NO 40
<211> LENGTH: 20
<212> TYPE: DNA
<213> ORGANISM: Artificial Sequence
<220> FEATURE:
<223> OTHER INFORMATION: PCR Primer

<400> SEQUENCE: 40
cacggtgctg gataccgaca                                                 20

<210> SEQ ID NO 41
<211> LENGTH: 20
<212> TYPE: DNA
<213> ORGANISM: Artificial Sequence
<220> FEATURE:
<223> OTHER INFORMATION: PCR Primer

<400> SEQUENCE: 41
ggtacacgta gaacgccgac                                                 20

<210> SEQ ID NO 42
<211> LENGTH: 19
<212> TYPE: DNA
<213> ORGANISM: Artificial Sequence
<220> FEATURE:
<223> OTHER INFORMATION: PCR Primer

<400> SEQUENCE: 42
tgttatacgc gcgtgttcg                                                  19

<210> SEQ ID NO 43
<211> LENGTH: 20
<212> TYPE: DNA
<213> ORGANISM: Artificial Sequence
<220> FEATURE:
<223> OTHER INFORMATION: PCR Primer
```

```
<400> SEQUENCE: 43
gccgaacagc aacctgatca                                          20

<210> SEQ ID NO 44
<211> LENGTH: 81
<212> TYPE: DNA
<213> ORGANISM: Artificial Sequence
<220> FEATURE:
<223> OTHER INFORMATION: BarSeq Oligo
<220> FEATURE:
<221> NAME/KEY: misc_feature
<222> LOCATION: (59)..(63)
<223> OTHER INFORMATION: n is a, c, g, or t

<400> SEQUENCE: 44
aatgatacgg cgaccaccga gatctacact ctttccctac acgacgctct tccgatctnn   60
nnngtcgacc tgcagcgtac g                                        81

<210> SEQ ID NO 45
<211> LENGTH: 80
<212> TYPE: DNA
<213> ORGANISM: Artificial Sequence
<220> FEATURE:
<223> OTHER INFORMATION: BarSeq Oligo
<220> FEATURE:
<221> NAME/KEY: misc_feature
<222> LOCATION: (59)..(62)
<223> OTHER INFORMATION: n is a, c, g, or t

<400> SEQUENCE: 45
aatgatacgg cgaccaccga gatctacact ctttccctac acgacgctct tccgatctnn   60
nngtcgacct gcagcgtacg                                          80

<210> SEQ ID NO 46
<211> LENGTH: 79
<212> TYPE: DNA
<213> ORGANISM: Artificial Sequence
<220> FEATURE:
<223> OTHER INFORMATION: BarSeq Oligo
<220> FEATURE:
<221> NAME/KEY: misc_feature
<222> LOCATION: (59)..(61)
<223> OTHER INFORMATION: n is a, c, g, or t

<400> SEQUENCE: 46
aatgatacgg cgaccaccga gatctacact ctttccctac acgacgctct tccgatctnn   60
ngtcgacctg cagcgtacg                                           79

<210> SEQ ID NO 47
<211> LENGTH: 78
<212> TYPE: DNA
<213> ORGANISM: Artificial Sequence
<220> FEATURE:
<223> OTHER INFORMATION: BarSeq Oligo
<220> FEATURE:
<221> NAME/KEY: misc_feature
<222> LOCATION: (59)..(60)
<223> OTHER INFORMATION: n is a, c, g, or t

<400> SEQUENCE: 47
aatgatacgg cgaccaccga gatctacact ctttccctac acgacgctct tccgatctnn   60
gtcgacctgc agcgtacg                                            78

<210> SEQ ID NO 48
<211> LENGTH: 242
```

```
<212> TYPE: DNA
<213> ORGANISM: Pseudomonas putida

<400> SEQUENCE: 48
ggcaagagca tccatcacgg ggcctgttca tgtttgaaat gtttcgataa tgaatcaata      60
gcttgcaaat atgcaacaag cagcctgact ttcgctcggc ggtgaggcgt cagaacccag     120
gctgtatgcg gcctgtggct gacttagagt tggcccaggc cttgctcttg ggcttgtgcc    180
aacccagaaa ccaaaggcag ggcctacaga accatgagca gttcaccaac gatttccccg    240
gc                                                                   242
```

BIOCONVERSION OF LEVULINIC ACID IN GENETICALLY ENGINEERED HOSTS

CROSS-REFERENCE TO RELATED APPLICATIONS

This is a divisional of co-pending application Ser. No. 16/135,123, filed Sep. 19, 2018, which claims priority to provisional application Ser. No. 62/560,247, filed Sep. 19, 2017, which are incorporated herein by reference.

FEDERAL FUNDING STATEMENT

This invention was made with government support under CBET1149678 awarded by the National Science Foundation. The government has certain rights in the invention.

BACKGROUND

Levulinic acid (LA) is a five carbon γ-keto acid that can be readily obtained from biomass through non-enzymatic, acid hydrolysis of a wide range of feedstocks. LA was named one of the US Department of Energy's "Top 12 value-added chemicals from biomass" because it can be used as a renewable feedstock for generating a variety of molecules, such as fuel additives, flavors, fragrances and polymers, through chemical catalysis. In addition, microbes can use LA as a sole carbon source and have been shown to convert LA into polyhydroxyalkanoates, short chain organic acids, and trehalose. (Chung, S. H., Choi, G. G., Kim, H. W. & Rhee, Y. H. Effect of Levulinic Acid on the Production of Poly (3-hydroxybutyrate-co-3-hydroxyvalerate) by *Ralstonia eutropha* KHB-8862. *Society* 39, 79-82 (2001). Berezina, N. & Yada, B. Improvement of the poly(3-hydroxybutyrate-co-3-hydroxyvalerate) (PHBV) production by dual feeding with levulinic acid and sodium propionate in *Cupriavidus necator*. *N. Biotechnol.* 33, 231-236 (2016). Valentin, H. E., Schönebaum, A. & Steinbüchel, A. Identification of 5-hydroxyhexanoic acid, 4-hydroxyheptanoic acid and 4-hydroxyoctanoic acid as new constituents of bacterial polyhydroxyalkanoic acids. *Appl. Microbiol. Biotechnol.* 46, 261-267 (1996). Jang, J. H. & Rogers, P. L. Effect of levulinic acid on cell growth and poly-beta-hydroxyalkanoate production by *Alcaligenes* sp SH-69. *J. Chem. Inf. Model.* 18, 219-224 (1996). Habe, H. et al. Bacterial production of short-chain organic acids and trehalose from levulinic acid: A potential cellulose-derived building block as a feedstock for microbial production. *Bioresour. Technol.* 177, 381-386 (2015). Martin, C. H., Wu, D., Prather, K. L. J. & Jones Prather, K. L. Integrated bioprocessing for the pH-dependent production of 4-valerolactone from levulinate in *Pseudomonas putida* KT2440. *Appl. Environ. Microbiol.* 76, 417-424 (2010). Yeon, Y. J., Park, H. Y. & Yoo, Y. J. Enzymatic reduction of levulinic acid by engineering the substrate specificity of 3-hydroxybutyrate dehydrogenase. Bioresour. Technol. 134, 377-380 (2013).) All of these bioconversion studies were conducted with natural bacterial isolates because the enzymes comprising a LA assimilation pathway were unknown. See Habe et al., supra. This knowledge gap limits metabolic engineering and the potential of creating novel LA bioconversions.

While the enzymes responsible for LA assimilation were unknown at the time of these bioconversion demonstrations, other studies identified putative intermediates and suggested pathways for LA catabolism. In a study where crude cell lysates of *Cupriavidus* necator were fed LA, the concentration of LA and free CoA decreased over time while acetyl-CoA and propionyl-CoA concentrations increased, suggesting that LA is catabolized via CoA thioesters like other short-chain organic acids. Jaremko, M. & Yu, J. The initial metabolic conversion of levulinic acid in *Cupriavidus necator*. *J. Biotechnol.* 155, 293-298 (2011). In a second study, cultures of *Pseudomonas putida* KT2440 expressing a heterologous TesB thioesterase were fed LA. Here, 4-hydroxyvalerate (4HV) and 3-hydroxyvalerate (3HV) transiently accumulated extracellularly before ultimately disappearing. Martin, C. H. & Prather, K. L. J. High-titer production of monomeric hydroxyvalerates from levulinic acid in *Pseudomonas putida*. *J. Biotechnol.* 139, 61-67 (2009). This observation strongly suggested that 4HV and 3HV (or their CoA thioesters) were pathway intermediates. Lastly, a metabolomic study of rat livers suggested that LA is catabolized to acetyl-CoA and propionyl-CoA via a unique phosphorylated acyl-CoA. (Zhang, G. F. et al. Catabolism of 4-hydroxyacids and 4-hydroxynonenal via 4-hydroxy-4-phosphoacyl-CoAs. *J. Biol. Chem.* 284, 33521-33534 (2009) and Harris, S. R. et al. Metabolism of levulinate in perfused rat livers and live rats: Conversion to the drug of abuse 4-hydroxypentanoate. *J. Biol. Chem.* 286, 5895-5904 (2011).) In sum, these observations suggest a relatively direct route from LA to beta-oxidation intermediates, but the enzymes comprising such a pathway remain unknown.

SUMMARY

To utilize LA as a substrate for microbial growth or bioconversion, a detailed understanding of the metabolic pathway and enzymes involved is necessary. As disclosed herein, the genetic and biochemical factors that allow *P. putida* KT2440 to catabolize LA were elucidated. Using a loss of function screen of a transposon library, a putative LA utilization operon was identified, isolated, incorporated into an unnatural expression vector. The expression vector was used to transform heterologous hosts which the expressed the genes necessary for the transformed hosts to utilize LA as a carbon source. The operon consists of seven genes: two homologs for membrane transporters and five enzymatic proteins. The pathway was reconstituted in vitro. It was determined that all five enzymatic proteins are required for complete conversion of LA into 3HV-CoA, an intermediate in the β-oxidation of odd-chain fatty acids. A closer inspection of the CoA ligase encoded in the operon revealed a broad substrate promiscuity including C4 to C6 organic acids. A putative regulator proximal to the operon activated transcription of the LA catabolic genes in the presence of LA or 4HV. The induction tests revealed that while the CoA ligase might have nonspecific activity towards similar chain length acids, the promoter is only responsive when cells were provided LA or 4HV. The catabolism of LA to acetyl-CoA and propionyl-CoA requires at least 2 ATP that likely come from respiration and the tricarboxylic acid cycle.

Thus, a first version of the invention is a recombinant expression vector comprising at least one promoter operably linked to at least three of, at least four of, or all five of lvaA, lvaB, lvaC, lvaD, and lvaE. The promoter may be inducible or constitutively active. The expression vector may optionally comprise a nucleotide sequence encoding an acetoacetyl-CoA transferase, a short-chain thioesterase and/or a succinyl-CoA transferase, operably linked to a promoter. The recombinant expression vector might also optionally comprise a nucleotide sequence encoding an acetoacetate decarboxylase operably linked to a promoter. The recombinant expression may optionally further comprise a nucleotide sequence encoding FadB and/or FadJ, operably linked to a promoter.

Also disclosed herein is a genetically modified host cell transformed to contain and express a heterologous recombinant expression vector as described herein. The genetically modified host cell may optionally be fadE negative and/or atoC negative. Optionally, the genetically modified host cell may also be fadA, fadI or atoB negative. Optionally, the genetically modified host cell may also be fadR negative. In another version of the modified host, the host cell may optionally comprise an increased copy number of nucleotide sequences encoding FadB and/or FadJ as compared to the wild-type of the host cell.

The host cell may be selected from the group consisting of an archaeal cell, a bacterial cell, and a eukaryotic cell. Bacteria and eukaryotic single-cell organisms are preferred host cells. In some instances, the host cell may endogenously encode activities catalyzed by LvaAB, LvaC, LvaD, and/or LvaE in its genome. In these instances, the invention may rely on natively encoded activities rather than heterologous activities conferred by the vector expressing lvaA, lvaB, lvaC, lvaD, and lvaE.

The genetically modified host cell may optionally constitutively expresses acetoacetyl-CoA transferase.

Also disclosed herein is a method of catabolizing levulinic acid. That is, a method of enabling a host cell to use levulinic acid as a carbon source. The method comprises culturing a genetically modified host cell as disclosed herein in a medium containing levulinic acid, under conditions and for a time wherein at least a portion of the levulinic acid is catabolized by action of the genetically modified host cell.

Yet another method disclosed herein is a method of making 2-butanone. The method comprises culturing a genetically modified host cell as disclosed herein, in a medium containing levulinic acid, under conditions and for a time wherein at least a portion of the levulinic acid is catabolized by action of the host cell into 2-butanone.

Also disclosed herein is a method of inducing a host cell to make 2-butanone from levulinic acid. The method comprises introducing into the host cell a heterologous operon encoding genes whose encoded proteins enable the host cell to catabolize levulinic acid into 3-hydroxyvaleryl-CoA (3HV-CoA); upregulating expression of 3-hydroxyacyl-CoA dehydrogenase in the host cell to drive oxidation of at least a portion of 3HV-CoA to 3-ketovaleryl-CoA (3 KV-CoA); and wherein the host cell expresses a nucleotide sequence encoding acetoacetyl-CoA transferase (atoDA) to drive conversion of at least a portion of the 3 KV-CoA into 3-ketovalerate; and also wherein the host cell expresses a nucleotide sequence encoding acetoacetate decarboxylase (adc) to drive conversion of at least a portion of the 2-ketovalerate into butanone. Optionally, the host cell is acetyl-CoA synthetase (Acs)-negative, phosphotransacetylase (Pta)-negative, and/or acetate kinase (Ack)-negative.

The heterologous genes described herein for catabolizing LA and producing 2-butanone may be introduced into the host cell on a single vector containing all the necessary genes and promoters. Alternatively, the heterologous genes may be introduced into the host cell on several separate vectors and under the control of separate promoters. Thus, also disclosed herein is a combination of recombinant expression vectors, the combination comprising one or more expression vectors, each vector having one or more promoters operably linked to one or more genes selected from the group consisting of lvaA, lvaB, lvaC, lvaD, and lvaE. The combination may optionally include a nucleotide sequence encoding an acetoacetyl-CoA transferase, a short-chain thioesterase, and/or a succinyl-CoA transferase, operably linked to a promoter. These gene(s) and promoter(s) may be found in at least one of the vectors along with one or more of the other genes, or may be present in one or more additional vectors. Optionally, at least one of the vectors, or an additional vector, comprises a nucleotide sequence encoding an acetoacetate decarboxylase and which is operably linked to a promoter. Also optionally, at least one of the vectors, or one or more additional vectors, comprises a nucleotide sequence encoding FadB and/or FadJ, both of which nucleotide sequences are operably linked to one or more corresponding promoters.

BRIEF DESCRIPTION OF THE DRAWINGS

FIG. 5A is a histogram depicting the abundance of CoA species created after 30 min of incubating LA, ATP, NAD(P)H with varying enzyme combinations (n=3). ABDE-C indicates that the LvaABDE reaction was performed first, metabolites were separated from LvaABDE, and the resulting solutions were supplemented with LvaC solely. The reaction confirms that LvaC is capable of converting 4PV-CoA to 3HV-CoA. FIG. 5B is a plot depicting the abundance of CoA species over a 60 minute time course for a mixture of LvaABCDE, LA, ATP, and NAD(P)H (n=3). Error bars represent standard deviation.

FIGS. 6A, 6B, 6C, and 6D are comparisons of 4HV-CoA and 4PV-CoA MS/MS spectra. FIG. 6A: MS/MS spectra for 4HV-CoA. FIG. 6B: Assignment of selected fragments from 4HV-CoA. FIG. 6C: MS/MS spectra for 4PV-CoA. FIG. 6D: Assignments of selected fragments from 4PV-CoA. The masses between the selected fragments of 4PV-CoA and 4HV-CoA differ by the mass of $PO_3H^-$ (79.967), indicating 4PV-CoA contains a phosphate group not found in 4HV-COA. Bold values indicate the mass of the parent ion. Peaks identified with the symbol (*) are fragments resulting from coenzyme A.

FIG. 15A shows growth on LA. FIG. 15B shows growth on LA and acedate.

FIG. 15C shows growth on LA for ΔatoB, and FIG. 15D shows growth of Δacs ΔackΔpta on LA and acetate.

Figure 1:
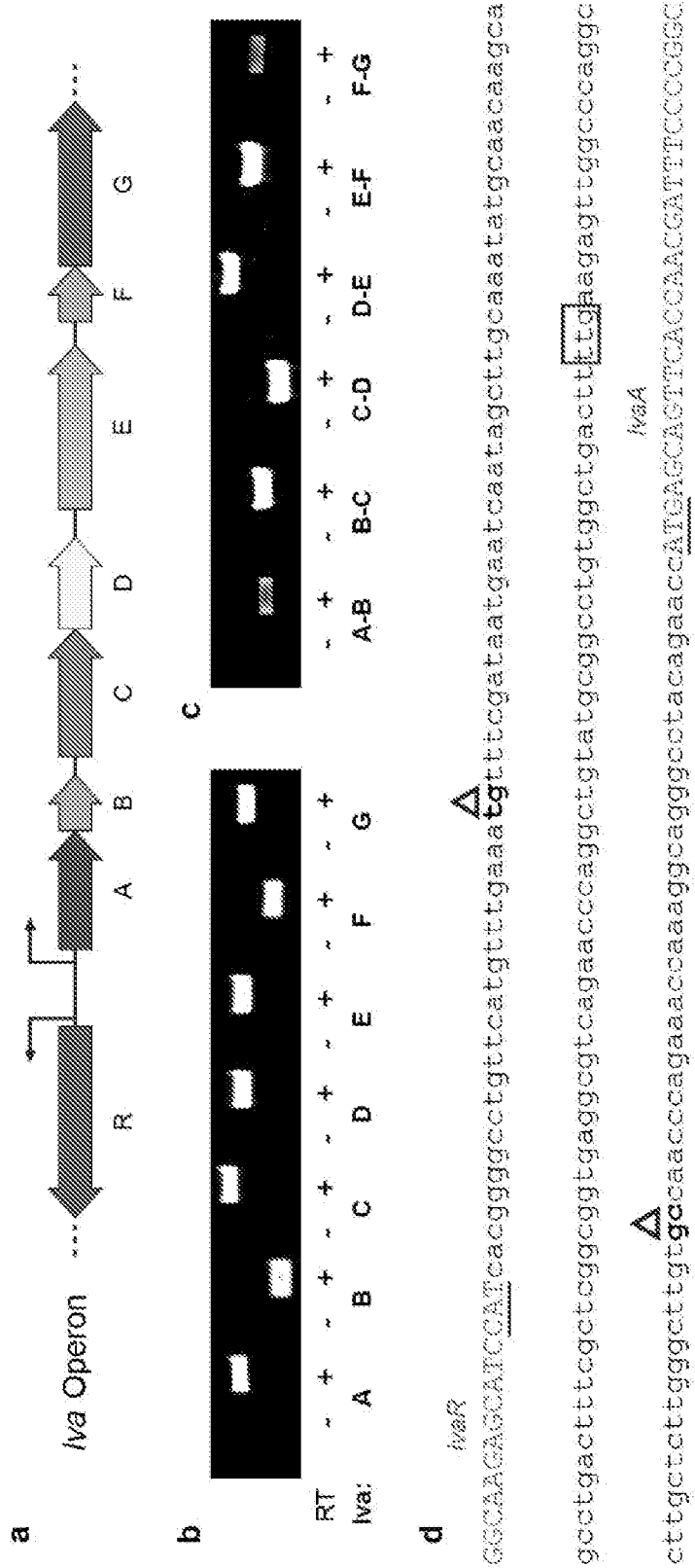
FIG. 1 depicts *P. putida* lva operon genetic characterization. Panel A: Organization of the lvaRABCDEFG (9,323 bp) operon. Panel B: Reverse Transcriptase (RT) PCR demonstrates that each gene is expressed in cells grown on LA. Samples were compared with the negative control (–RT) where reverse transcriptase was omitted from the reaction. Panel C: RT-PCR of cDNA created with primer JMR237 demonstrates that the operon is polycistronic. Note that a product spanning each intergenic region was observed. Panel D: The transcription start sites (TSS) of regulator lvaR and lvaA were identified by 5'-RACE. Underlined sequence indicates ATG start codon. Triangle highlights experimentally determined TSS. Boxed sequence indicates previously annotated translation start site for lvaA.

```
OPERON SEQUENCES
lvaA
nt:
                                         (SEQ. ID. NO: 1)
atgagcagttcaccaacgatttccccggccagcgatacgttcgcggc catgactgacgatcaccgcctggccgagttcatccgcgagcaggcct cggcaacgcgggtggtcatccaggcgcgcaagcgcctgagcggcggc gctatccaggaaaactggctgctggacctgctgatcgaaggcggcc gtgggccggtgtccggcgttgggtactgcgcagcgatgcgctttcag cgctacccgccagccttgaccgtgaacaggagttcgccgtgctgcag gtggtttaccaggccggcgtgaaagtgccacgcccgctctggctgtg ccgcgatgtgcgcgtgcatgggcgggtgttcttcctgatggagtatg tgccgggtagcgctgccggccgcgcgctcagcaccggcgccggtcct cagggccgggcgcaactggcgacgcagcttggcgccaacctggcgcg tctgcatcaggtccgccgccgtgcgccacgctgtgcttcctgtccg
```

```
ttccggacagctcgccggccctggcgaccatcgacgcctaccgccgc tacctcgacaccctcgccgatgcctatccggtgctggaatggggcct gcgctggtgcgagctgcatgcgccgcgcagcagcaccctgtgcctgt tgcaccgtgactaccgcaccggcaactacctggccagcgaagaaggg ctggaggccgtgctcgactgggagttcaccggctggggagatccttg cgaggacctcggctggttcaccgcccgttgctggcgttttaccgtc cagacctcgaagccggcggcattggccagctggaggattttctgcgt ggttatcacgaggtgtcttcgctgtgcatcgagcgcagtcggctcca ctactggcaagtcatggccaccctgcgctgggcggtgattgccttgc agcaagggcagcgccatctgtccggtgaagaaccgtcgctcgagcta gcactgacagcccggctgttgccggagctcgaactcgacatcctgca catgaccggagccgaagcgccatga aa:
                                          (SEQ. ID. NO: 2)
MSSSPTISPASDTFAAMTDDHRLAEFIREQASATRVVIQARKRLSGG

AIQENWLLDLLIEGGPWAGVRRWVLRSDALSALPASLDREQEFAVLQ

VVYQAGVKVPRPLWLCRDVRVHGRVFFLMEYVPGSAAGRALSTGAGP

QGRAQLATQLGANLARLHQVRPPCATLCFLSVPDSSPALATIDAYRR

YLDTLADAYPVLEWGLRWCELHAPRSSTLCLLHRDYRTGNYLASEEG

LEAVLDWEFTGWGDPCEDLGWFTARCWRFTRPDLEAGGIGQLEDFLR

GYHEVSSLCIERSRLHYWQVMATLRWAVIALQQGQRHLSGEEPSLEL

ALTARLLPELELDILHMTGAEAP* lvaB
nt:
                                          (SEQ. ID. NO: 3)
atgacccaacccaacgcccacgaattgctcgagatcgcccgcgcgac gcttctggagcagctgctgccagcgctgcccggcgagttgcgttacc cggccctgatgatcgcaaacgccatggccattgcggcccgcgaaaac cgcttgggcgctcaggccgaggatcaggagcaggcgcgtctggccgc cttggtcgatgacgcgccgtcgacattgcccgacctgcgccgccaac tggctcgcgccattcgccagggcagccatgacgccccgcaaacccgg cgcaccctggtcgagacattacgccagatcaccgttgcccgattggc gatcagcaaccccaaggccttgccctga aa:
                                          (SEQ. ID. NO: 4)
MTQPNAHELLEIARATLLEQLLPALPGELRYPALMIANAMAIAARE

NRLGAQAEDQEQARLAALVDDAPSTLPDLRRQLARAIRQGSHDAPQ

TRRTLVETLRQITVARLAISNPKALP* lvaC
nt:
                                          (SEQ. ID. NO: 5)
atgaacttcactctcccggacgaactgctcgccttgcaggccaaga ctcgagacttcattgccgaacaggtcatcccattcgagaacgaccc ccgccagaacagccacggcccccagcgacgcactgcgccaggacctg gtgctctgcgcccgcgccgctggcttgctgacgcctcacgccagcc gcgaaatgggcggtctggaactgagccatgtggccaaggcgatcgt
```

-continued

```
cttcgaagaagccggctactcgccgctgggcccggtagcgctgaat
atccatgcgccggacgaaggcaatatccacctgatggacgtggtcg
ccaccgaagcgcagaaggaccgctggttgcgcccgctggtccaggg
ccatgcccgttcgtgcttcgccatgacggagcctgctccgggctcc
ggttcggatccgtcgatgctgcgcaccactgccacccgcgatggcg
acgactacctgatcaatggtcgcaagtggctgatcaccggggccga
aggcgcggacttcggcatcatcatggcgcgcatggaggacggcacc
gcgaccatgttcctgaccgacatgaagcgcgacggcatcatccatg
aacgtcagctggactcgctggacagctgttttaccggcggtcacgg
gcagctgcgtttcgacaacctgcgtattccggcgagcgatgtcctc
ggcgagatcggcaagggcttccggtatgcccaggtgcgcctggcgc
ctgcacgcttgactcattgcatgcgctggctcggtgccgcgcgccg
cgcccacgacatcgcctgcgactatgcgcgcacccgggacgccttt
ggcaagccgctgggcgagcaccagggcgtgggtttcatgctggccg
acaacatgatggacctgcacgtggtgcgtctggcggtctggcactg
cgcctgggtgctcgaccagggccggcgcgccaatgtcgattcgagc
atggccaaggtgatcagcgccgaggcgctgtggcgggtggtcgatc
gttgcgtccaggtattgggtggacgcggggtgaccggggacaccgt
ggtggagcggatcttccgcgacattcgcccgttccgcatctatgac
ggcccgagcgaagtgcaccgcatgagcctggcgaagaagctgctcg
accagcgcctggaggcccactga
aa:
                                        (SEQ. ID. NO: 6)
MNFTLPDELLALQAKTRDFIAEQVIPFENDPRQNSHGPSDALRQDL
VLCARAAGLLTPHASREMGGLELSHVAKAIVFEEAGYSPLGPVALN
IHAPDEGNIHLMDVVATEAQKDRWLRPLVQGHARSCFAMTEPAPGS
GSDPSMLRTTATRDGDDYLINGRKWLITGAEGADFGIIMARMEDGT
ATMFLTDMKRDGIIHERQLDSLDSCFTGGHGQLRFDNLRIPASDVL
GEIGKGFRYAQVRLAPARLTHCMRWLGAARRAHDIACDYARTRDAF
GKPLGEHQGVGFMLADNMMDLHVVRLAVWHCAWVLDQGRRANVDSS
MAKVISAEALWRVVDRCVQVLGGRGVTGDTVVERIFRDIRPFRIYD
GPSEVHRMSLAKKLLDQRLEAH* lvaD
nt:
                                        (SEQ. ID. NO: 7)
atgcagccgaaccttgcccgactgttcgccctcgacgggcgtcgc
gccctggtgaccggggcctccagcggcctgggccgtcacttcgcc
atgaccctggccgccgcaggcgccgaggtggtggtgaccgccaga
cgccaggcgccgctgcaggcgttggtggaggccatcgaggtggcc
ggaggcgggcgcaggcctttgccctcgatgtgacgagccgtgag
gacatctgccgggtgctcgatgccgccggccgctggatgttctg
gtcaacaatgcgggggtgagcgacagccagcctttgctagcctgc
gatgatcaaacctgggaccacgtgctcgacaccaacctcaagggc
```

```
gcctgggccgtggcccaggaaagcgcccggcgcatggtggtggcg
gggaaggggggcagcctgatcaatgtcacctcgatcctcgccagc
cgtgtggccggcgccgtcggcccttacctggcggccaaggccggc
ctggcccacctgacccgcgccatggcgctggagttggcgcgccat
ggtatccgggtgaacgccctggcgcccggctacgtgatgactgat
ttgaacgaggccttcctggccagcgaggccggtgacaagttgcgc
tcgcggatcccagccgccgcttcagcgtgccgtcggacctggac
ggcgccttgctgctgctcgccagcgatgccgggcgggcgatgagc
ggcgctgagatcgtggtcgatggcggccacctgtgcagcagcctg
taa aa:
                                        (SEQ. ID. NO: 8)
MQPNLARLFALDGRRALVTGASSGLGRHFAMTLAAAGAEVVVTAR
RQAPLQALVEAIEVAGGRAQAFALDVTSREDICRVLDAAGPLDVL
VNNAGVSDSQPLLACDDQTWDHVLDTNLKGAWAVAQESARRMVVA
GKGGSLINVTSILASRVAGAVGPYLAAKAGLAHLTRAMALELARH
GIRVNALAPGYVMTDLNEAFLASEAGDKLRSRIPSRRFSVPSDLD
GALLLLASDAGRAMSGAEIVVDGGHLCSSL* lvaE
nt:
                                        (SEQ. ID. NO: 9)
atgatggttccaaccctcgaacacgagcttgctcccaacgaagcc
aaccatgtcccgctgtcgccgctgtcgttcctcaagcgtgccgcg
caggtgtacccgcagcgcgatgcggtgatctatggcgcaaggcgc
tacagctaccgtcagttgcacgagcgcagccgcgccctggccagt
gccttggagcgggtcggtgttcagccgggcgagcgggtggcgata
ttggcgccgaacatcccggaaatgctcgaggccactatgcgcgtg
cccggtgccggggcggtgctggtgtgcatcaacatccgcctggag
gggcgcagcattgccttcatcctgcgtcactgcgcggccaaggta
ttgatctgcgatcgtgagttcggtgccgtggccaatcaggcgctg
gccatgctcgatgcgccgcccttgctggtgggcatcgacgatgat
caggccgagcgcgccgatttggcccacgacctggactacgaagcg
ttcttggcccaggcgaccccgcgcggccgttgagtgcgccacag
aacgaatggcagtcgatcgccatcaactacacctccggcaccacg
ggggaccccaaggcgtggtgctgcatcaccgcggcgcctacctc
aacgcctgcgccggggcgctgatcttccagttggggccgcgcagc
gtctacttgtggaccttgccgatgttccactgcaacggctggagc
cataccctgggcggtgacgttgtccggtggcacccacgtgtgtctg
cgcaaggtccagcctgatgcgatcaacgccgccatcgccgagcat
gccgtgactcacctgagcgccgccccagtggtgatgtcgatgctg
atccaccgcgagcatgccagcgccctccggtgccggttcggtg
atcactggcggtgccgccccgcccagtgcggtcatcgcggcgatg
gaggcgcgtggcttcaacatcacccatgcctatggcatgaccgaa
```

-continued

```
agctacggtcccagcacattgtgcctgtggcagccgggtgtcgac gagttgccgctggaggcccgggcccagttcatgagccgccagggc gtcgcccaccgctgctcgaggaggccacggtgctggataccgac accgccgcccggtcccggccgacggccttaccctcggcgagctg gtggtgcggggcaacactgtgatgaaaggctacctgcacaaccca gaggctaccgtgccgcgttggccaacggctggctgcacacgggc gacctggccgtgctgcacctggacggctatgtggaaatcaaggac cgagccaaggacatcatcatttctggcggcgagaacatcagttcg ctggagatagaagaagtgctctaccagcaccccgaggtggtcgag gctgcggtggtggcgcgtccggattcgcgctggggcgagacacct cacgctttcgtcacgctgcgcgctgatgcactggccagcggggac gacctggtccgctggtgccgtgagcgtctggcgcacttcaaggcg ccgcgccatgtgtcgctcgtggacctgcccaagaccgccactgga aaaatacagaagttcgtcctgcgtgagtgggcccggcaacaggag gcgcagatcgccgacgccgagcattga
```

```
aa:
                                 (SEQ. ID. NO: 10)
MMVPTLEHELAPNEANHVPLSPLSFLKRAAQVYPQRDAVIYGARR

YSYRQLHERSRALASALERVGVQPGERVAILAPNIPEMLEAHYGV

PGAGAVLVCINIRLEGRSIAFILRHCAAKVLICDREFGAVANQAL

AMLDAPPLLVGIDDDQAERADLAHDLDYEAFLAQGDPARPLSAPQ

NEWQSIAINYTSGTTGDPKGVVLHHRGAYLNACAGALIFQLGPRS

VYLWTLPMFHCNGWSHTWAVTLSGGTHVCLRKVQPDAINAAIAEH

AVTHLSAAPVVMSMLIHAEHASAPPVPVSVITGGAAPPSAVIAAM

EARGFNITHAYGMTESYGPSTLCLWQPGVDELPLEARAQFMSRQG

VAHPLLEEATVLDTDTGRPVPADGLTLGELVVRGNTVMKGYLHNP

EATRAALANGWLHTGDLAVLHLDGYVEIKDRAKDIIISGGENISS

LEIEEVLYQHPEVVEAAVVARPDSRWGETPHAFVTLRADALASGD

DLVRWCRERLAHFKAPRHVSLVDLPKTATGKIQKFVLREWARQQE

AQIADAEH*
```

DETAILED DESCRIPTION

Abbreviations and Definitions

ATP=adenosine triphosphate. CoA=coenzyme-A. 3HV=3-hydroxyvalerate. 4HV=4-hydroxyvalerate. 4HV-CoA=4-hydroxyvaleryl-CoA. 3 KV-CoA=3-ketovaleryl-CoA. LA=levulinic acid. LA-CoA=levulinyl-CoA. MOPS=3-(N-morpholino)propanesulfonic acid. NAD(P)H=Nicotinamide adenine dinucleotide (phosphate) reduced. 4PV-CoA=4-phosphovaleryl-CoA. 5'-RACE=Rapid Amplification of cDNA Ends. sfGFP=super-folder green fluorescent protein (see Pédelacq J D, Cabantous S, Tran T, Terwilliger T C, Waldo G S, *Nat Biotechnol.* 2006 January; 24(1):79-88). TSS=transcription start site.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (also called "non-coding" RNA or "ncRNA"; e.g. tRNA, rRNA, a ribozyme, etc.).

A "protein coding sequence" or "coding region" is a sequence that encodes a particular protein or polypeptide. A "protein coding sequence" or "coding region" is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic, viral, or eukaryotic mRNA, genomic DNA sequences from prokaryotic, viral, or eukaryotic DNA, and synthetic nucleic acids. A transcription termination sequence will usually be located 3' to the coding region.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), all of which are well known in the art. "BLAST"=Basic Local Alignment Search Tool; available online from the U.S. National Library of Medicine at blast.ncbi.nlm.nih.gov/Blast.cgi; see Altschul, Gish, Miller, Myers, and Lipman, (1990) "Basic local alignment search tool," *Journal of Molecular Biology.* 215(3): 403-410. "T-COFFEE"=Tree-based Consistency Objective Function for Alignment Evaluation; see Notredame C, Higgins D G, Heringa J (2000-09-08) "T-Coffee: A novel method for fast and accurate multiple sequence alignment," *J Mol Biol* 302(1):205-217; available online at coffee.org/. "MUSCLE"=Multiple Sequence Comparison by Log-Expectation; available online from the European Bioinformatics Institute (EMBL-EBI) at www.ebi.ac.uk/Tools/msa/muscle/; see Edgar, RC (2004) "MUSCLE: a multiple sequence alignment method with reduced time and space complexity," *BMC Bioinformatics,* 5:113. "MAFFT"=Multiple Alignment using Fast Fourier Transform; available online at mafft.cbrc.jp/alignment/software/; see Katoh, Misawa, Kuma, Miyata (2002) "MAFFT: a novel method for rapid multiple sequence alignment based on fast Fourier transform," *Nucleic Acids Res.* 30:3059-3066.

The term "binding", as used herein refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

A "promoter sequence" is a DNA regulatory region capable of binding RNA polymerase and initiating transcription of a downstream (3' direction) coding or non-coding sequence. For purposes of defining the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various prokaryotic and eukaryotic promoters, including inducible promoters, may be used in the various recombinant expression vectors of the present disclosure. The promoter may be a constitutively active promoter, i.e. a promoter that is active in the absence externally applied agents, or it may be an inducible promoter (e.g., T7 RNA polymerase promoter, T3 RNA polymerase promoter, Isopropyl-beta-D-thiogalactopyranoside (IPTG)-regulated promoter, heat shock promoter, anhydro tetracycline-regulated promoter, arabino se-inducible promoter, CRISPRi-regulated promoter, TAL-Effector-regulated promoter, phosphate-starvation-regulated promoter, steroid-regulated promoter, metal-regulated promoter, methionine-inducible promoter; a galactose-inducible promoter, and the like). As used herein, an inducible promoter is a promoter whose activity is regulated upon the application of an agent to the cell, (e.g. doxycycline) or the induced presence of a particular RNA polymerase (e.g., T7 RNA polymerase).

Agents that induce any given inducible promoter are known in art. For example, tetracycline-regulatable promoters can be regulated by tetracycline or doxycycline; carbohydrates can be used to induce a carbohydrate-inducible promoter (e.g., galactose for a galactose-inducible promoter); methionine can be used to induce a methionine-inducible promoter; metals can be used to induce a metallothionein promoter, etc.).

The terms "control element," and "regulatory element," used interchangeably herein, refer to transcriptional, translational, and degradation control sequences that are transcribed as part of the RNA molecule whose activity that they regulate. Such regulatory elements can control a wide variety of processes (activities) including but not limited to transcription (e.g., initiation, elongation, and/or termination), translation (initiation, elongation, and/or termination), RNA stability, etc. Regulatory elements include but are not limited to recognition sequences for antisense RNAs, leader sequences, riboswitches, a 5' methyl cap, a 3' poly-A tail, sequences recognized by ribozymes, sequences recognized by ribosomes (e.g., a ribosome binding site (RBS), e.g., Shine-Delgarno Sequence), self-cleaving ribozymes, leader-sequences, sequences bound by RNA binding proteins, sequences targeted by a guide-strand-bound RISC complex, etc.

Some regulatory elements are operably linked to a promoter, but reciprocally regulate transcription (e.g., via early termination of RNA polymerase elongation) such that the promoter affects transcription of the regulatory element and the regulatory element also affects transcription of its own transcript. Some regulatory elements (e.g., IS10wt, IS10-9, and others known in the art: the RNA-IN/OUT translation control system) can function as part of an antisense RNA-mediated translation control system (Mutalik et al. *Nature Chem. Biol.* 2012 (8) May: 447-454; Kittle et al. *J Mol. Biol.* 1989 Dec. 5; 210 (3):561-72: Insertion sequence IS10 antisense pairing initiates by an interaction between the 5' end of the target RNA and a loop in the anti-sense RNA). Other exemplary regulatory elements that find use in the expression vectors, compositions, methods, and kits of this disclosure include but are not limited to PT181 wt and its orthologs, IS10wt and its orthologs, Bujard RBS, B0030 RBS, Weiss RBS, Anderson RBS, lacZpl UTR, serB UTR, chiA UTR, lacY UTR, sodA UTR, ompRp3UTR, trpR UTR, glpA UTR, rhoL UTR, CRISPRI UTR, fixA UTR, 11dP UTR, and the like.

The term "naturally-occurring" or "unmodified" as used herein as applied to a nucleic acid, a polypeptide, a cell, or an organism that is found in nature.

"Recombinant" means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame and may indeed act to modulate production of a desired product by various mechanisms (see "regulatory element", above). Alternatively, DNA sequences encoding RNA that is not translated may also be considered recombinant. Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention.

A "vector" or "expression vector" is a replicon, such as plasmid, phage, virus, or cosmid, to which another DNA segment (an "insert") may be attached so as to bring about the replication of the attached segment in a cell. An "expression cassette" comprises a DNA coding sequence operably linked to a promoter.

The term "operably linked" refers to a physical juxtaposition of nucleic acids in a polynucleotide wherein the components so described are in a relationship permitting them to function in their intended manner. For instance, a coding sequence is operably linked to a promoter (or the promoter can be said to be operably linked to the coding sequence) if the promoter affects the transcription or expression of the coding sequence. If a regulatory element is operably linked to a promoter, the regulatory element is transcribed and the promoter affects the transcription of the regulatory element. Nucleotides that are operably linked need not be (and often are not) directly linked to each other.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence.

A recombinant expression vector may also contain an insertion site for the insertion of a sequence of interest. An "insertion site" is any nucleotide sequence intentionally positioned within the vector that allows for convenient insertion and/or excision of additional nucleic acid sequences. The term "insertion site" encompasses sequences that facilitate any convenient cloning methodology (e.g., standard restriction enzyme/ligation based methods, integrase based methods, T4 DNA Polymerase based methods, BioBrick cloning, Circular Polymerase Extension Cloning (CPEC) cloning, etc.) (Quan, J. & Tian, *J. Nat. Protoc.* 6, 242-251 (2011); Shetty et al. *J. Biol. Eng.* 2, 5 (2008)). An example of one possible type of standard insertion site is a multiple cloning site (or polylinker), which is a stretch of sequences that contains multiple restriction enzyme sites that together facilitate convenient restriction enzyme/ligation based cloning methods.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include viral infection, transfection, conjugation, protoplast fusion, electroporation, particle gun technology, calcium phosphate precipitation, direct micro injection, and the like. The choice of method is generally dependent on the type of cell being transformed and the circumstances under which the transformation is taking place (in vitro, ex vivo, or in vivo). A general discussion of these methods can be found in Ausubel, et al., Short Protocols in Molecular Biology, 5th ed., Wiley & Sons, 2002.

Disclosed herein are a series of isolated genes and their corresponding encoded proteins. The genes have been assigned the names lvaA, lvaB, lvaC, lvaD, and lvaE. The corresponding proteins encoded by the genes have been assigned the names LvaA, LvaB, LvaC, LvaD, and LvaE. The genes and the proteins encoded thereby are explicitly defined herein as follows:

lvaA is defined as a gene encoding a phosphotransferase that phosphorylates the 4-hydroxy position on 4-hydroxyvaleryl-CoA (4HV-CoA) to form 4-phosphovaleryl-CoA (4PV-CoA). The gene has at least 80% sequence identity and more preferably at least 90% sequence identity to PP_2791 from *Pseudomonas putida*.

lvaB is defined as a gene encoding a small protein associated with LvaA that is essential for the phosphorylation of 4HV-CoA by LvaA. The gene has at least 80% sequence identity and more preferably at least 90% sequence identity to PP_2792 from *Pseudomonas putida*. In some cases, a single protein contains sequence homology to both LvaA and LvaB. (That is, LvaA and LvaB appear as a type of fusion protein.)

lvaC is defined as a gene encoding an acyl-CoA dehydrogenase family protein that hydrates either 2-pentenoyl-CoA or 3-pentenoyl-CoA to form 3-hydroxyvaleryl-CoA (3HV-CoA). The gene has at least 80% sequence identity and more preferably at least 90% sequence identity to PP_2793 from *Pseudomonas putida*.

lvaD is defined as a gene encoding a reductase that reduces 4-ketovaleryl-CoA to 4HV-CoA. The gene has at least 80% sequence identity and more preferably at least 90% sequence identity to PP_2794 from *Pseudomonas putida*.

lvaE is defined as a gene encoding a protein that acts as a acyl-CoA synthetase on levulinic acid to form levulinyl-CoA (4-ketovaleryl-CoA). The gene has at least 80% sequence identity and more preferably at least 90% sequence identity to PP_2795 from *Pseudomonas putida*.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The singular indefinite articles "a" and "an" mean "one or more," unless specifically defined otherwise.

All combinations of method or process steps as used herein can be performed in any order, unless otherwise specified or clearly implied to the contrary by the context in which the referenced combination is made.

The methods and genetic constructs of the present invention can comprise, consist of, or consist essentially of the essential elements and limitations as described herein, as well as any additional or optional ingredients, components, or limitations described herein or otherwise useful in recombinant genetics.

Identification of Genes Involved in Levulinic Acid Metabolism

*P. putida* KT2440 is known to metabolize LA as a sole carbon source and demonstrates diauxic growth in the presence of glucose and LA. Therefore, a genetic study was initiated to identify genes involved in LA catabolism. A mutant library was constructed with a Tn5 mini transposase (Martinez-Garcia, E., Calles, B., Arévalo-Rodríguez, M. & de Lorenzo, V. pBAM1: an all-synthetic genetic tool for analysis and construction of complex bacterial phenotypes. *BMC Microbiol.* 11, 38 (2011)) and screened for *P. putida* mutants lacking the ability to grow on LA as the sole carbon source. Thirteen out of 7,000 colonies screened demonstrated LA growth deficiencies. The location of each transposon insertion was determined by sequencing PCR products created with a primer nested in the transposon paired with a degenerate random primer. Table 1 shows the ten unique isolates from these thirteen hits and the putative function of the disrupted genes. Two mutants had disruptions in genes involved in propionate metabolism, supporting the hypothesis that LA is catabolized to the central metabolites, acetyl-CoA and propionyl-CoA. Three transposon mutants had disruptions in a putative operon that had not been previously characterized (disrupting genes PP_2791, PP_2793, and PP_2794). Other mutants had disruptions in genes with no obvious connection to LA catabolism (bioH, gcvP, a hypothetical zinc protease, mrdA, and fpvA). To confirm that a sufficient number of clones had been screened, a random bar code transposon-site sequencing (RB-TnSeq) was performed for cultures enriched by growth on LA and 4HV relative to growth on glucose. RB-TnSeq is an efficient method for determining gene essentiality under different conditions with high genomic coverage. Wetmore, K. M. M. et al. Rapid Quantification of Mutant Fitness in Diverse Bacteria by Sequencing Randomly Bar-Coded Transposons. *M Bio* 6, 1-15 (2015). This analysis identified additional genes involved in LA metabolism including an acetoacetyl-CoA transferase important for growth on LA, genes functioning in β-oxidation and propionyl-CoA metabolism, and 14 transcriptional regulators potentially involved in LA metabolism. The RB-TnSeq dataset also revealed that 3-hydroxybutyryl-CoA dehydrogenase and β-ketothiolase are also necessary for growth on LA and 4HV, supporting our hypothesis that LA metabolism terminates through β-oxidation. For a more complete summary and analysis of the fitness data, see the Examples.

TABLE 1

*P. putida* Levulinic Acid Transposon Insertion Sites

| Locus   | Insertion Point* | Gene Name | Description/Homology |
|---------|------------------|-----------|----------------------|
| PP_0364 | 442685           | bioH      | pimeloyl-ACP methyl ester esterase |
| PP_0988 | 1128706          | gcvP-1    | glycine dehydrogenase |
| PP_2332 | 2660666          | N/A       | ATP-dependent zinc protease family |
| PP_2336 | 2666405          | acnA-II   | aconitate hydratase |
| PP_2337 | 2666944          | prpF      | aconitate isomerase |
| PP_2791 | 3181098          | N/A       | Phosphotransferase family |
| PP_2793 | 3182533          | N/A       | acyl-CoA dehydrogenase family protein |
| PP_2794 | 3183601          | N/A       | short chain dehydrogenase/reductase family |
| PP_3741 | 4271628          | mrdA-I    | transpeptidase |
| PP_4217 | 4765953          | fpvA      | TonB-dependent outer membrane ferripyoverdine receptor |

*Insertion point based on location from *P. putida* KT2440 origin

Operon Characterization and Induction

Given the Propensity of Bacteria to Cluster Related Genes into Operons, the Putative Seven-gene operon, PP_2791-PP_2797 was examined, which contained three of the transposon hits (PP_2791, PP_2793 and PP_2794). The sequence homology of the seven genes in the operon was analyzed using the basic local alignment search tool (BLAST; Altschul, S. F., Gish, W., Miller, W., Myers, E. W. & Lipman, D. J. Basic local alignment search tool. *J. Mol. Biol.* 215, 403-10 (1990)) and assigned predicted functions, which are listed in Table 2, below. There are no known published studies about these genes beyond the automated sequence annotations. Therefore, the expression and function of these genes was investigated to determine if they are involved in LA catabolism. First, RNA from wild type *P. putida* grown in minimal media with LA as the carbon source was isolated. All seven genes were then located by PCR amplification of cDNA created with a reverse primer specific to PP_2797. See FIG. 1, panels A, B, and C. The transcription start site (TSS) of the operon was isolated by 5'-RACE (see FIG. 1, panel D) and implicated a different start codon for PP_2791.72 bp downstream of the one originally reported. Schramm, G., Bruchhaus, I. & Roeder, T. A simple and reliable 5'-RACE approach. *Nucleic Acids Res* 28, E96 (2000). Espah Borujeni, A., Channarasappa, A. S. S. & Salis, H. M. M. Translation rate is controlled by coupled trade-offs between site accessibility, selective RNA unfolding and sliding at upstream standby sites. *Nucleic Acids Res.* 42, 2646-2659 (2014). Salis, H. M. M., Mirsky, E. A. A. & Voigt, C. A. A. Automated design of synthetic ribosome binding sites to control protein expression. *Nat. Biotechnol.* 27, 946-50 (2009). A $\sigma^{54}$ promoter sequence located upstream of PP_2791 was identified by comparing upstream of the new TSS with published $\sigma^{54}$ promoter consensus sequences. Barrios, H., Valderrama, B. & Morett, E. Compilation and analysis of sigma(54)-dependent promoter sequences. *Nucleic Acids Res.* 27, 4305-4313 (1999). The data presented below suggests the proteins encoded by this operon are important in LA catabolism. The polycistronic genes are designated herein as lvaABCDEFG.

Figure 2A:
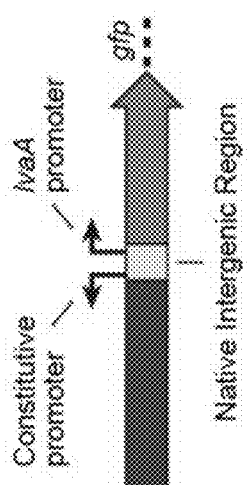
FIG. 2A is schematic of transcriptional GFP fusion used to test induction of the lva operon. lvaR was cloned onto a plasmid containing its native constitutive promoter and the native promoter region for lvaA. The fluorescent protein sfGFP was cloned in place of lvaA.
Figure 2B:
FIG. 2B depicts the results of a lva operon induction assay. GFP fluorescence was measured from LB-cultures supplemented with various organic acids (20 mM) (n=3). Error bars represent standard deviation.

Upstream of lvaABCDEFG, a gene oriented divergently from the operon (PP_2790) was identified and predicted to encode a transcription factor with a $\sigma^{54}$ interaction domain and homology to the propionate metabolism activator, prpR. The genomic organization strongly suggested that the gene encoded a regulator for the lva operon. Consequently, PP_2790 was deleted and growth of *P. putida* strains was evaluated on both LA and a likely intermediate, 4HV. The ΔPP_2790 mutant was unable to grow on LA and 4HV suggesting that it acts as an activator for the operon. Expression of PP_2790 on a plasmid restored growth of the deletion strain on LA and 4HV. To identify compounds that activate lvaABCDEFG expression, a transcriptional reporter system was built that linked sfGFP to the $\sigma^{54}$ promoter sequence located upstream of lvaA. The reporter cassette was cloned onto a broad host range vector (shown schematically in FIG. 2A) and the resulting construct was transformed into wild type *P. putida*. A variety of short and medium chain length acids were tested by adding them to rich media and evaluating the corresponding sfGFP expression levels. Strong sfGFP fluorescence was observed only when LA or 4HV were added to the system. See FIG. 2B. Without being limited to any underlying mechanism, it is thought that PP_2790 encodes a transcriptional regulator responsive to the LA pathway. It is designated herein as lvaR.

Genetic and Biochemical Studies of lvaABCDEFG Operon

Figure 3:
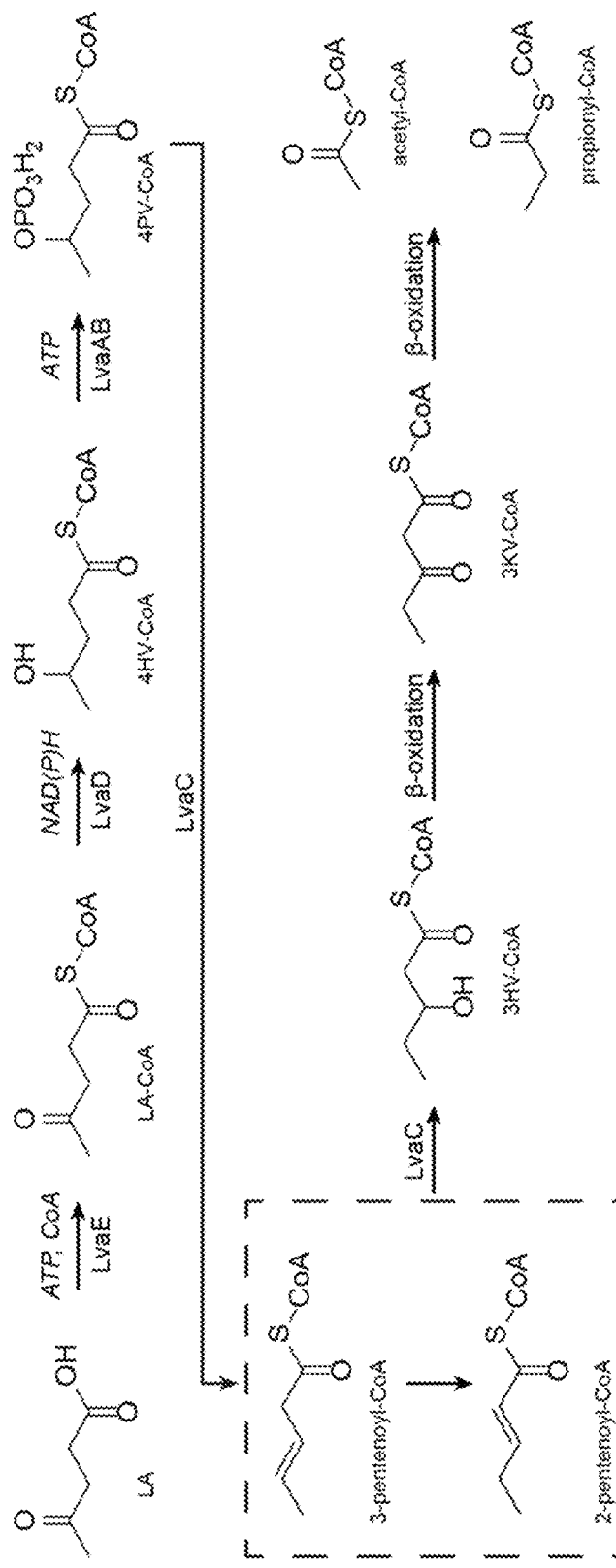
FIG. 3 depicts the proposed pathway for LA metabolism. LA, levulinic acid; 4HV, 4-hydroxyvalerate; 3HV, 3-hydroxyvalerate; LA-CoA, levulinyl-CoA; 4HV-CoA, 4-hydroxyvaleryl-CoA; CoA, coenzyme-A; ATP, adenosine triphosphate; 4PV-CoA, 4-phosphovaleryl-CoA; 3 KV-CoA, 3-ketovaleryl-CoA; NAD(P)H, Nicotinamide adenine dinucleotide (phosphate) reduced.

To confirm the involvement of the lva operon in LA catabolism, a deletion mutant was created for each lva gene predicted to encode an enzymatic protein and a corresponding complementation plasmid using the $P_{araBAD}$ promoter. The ability of the resulting strains to grow on LA and 4HV was tested. See Table 2, below. In addition, we purified the five enzymes from cultures of *E. coli* BL21 (DE3), reconstituted the enzymatic reactions in vitro, and used liquid chromatography/mass spectrometry (LC/MS) to identify reaction products. Selective ion scanning was used to monitor the masses for likely intermediates based on prior studies. Jaremko, M. & Yu, J. The initial metabolic conversion of levulinic acid in *Cupriavidus necator. J. Biotechnol.* 155, 293-298 (2011). Martin, C. H. & Prather, K. L. J. High-titer production of monomeric hydroxyvalerates from levulinic acid in *Pseudomonas putida. J. Biotechnol.* 139, 61-67 (2009). Zhang, G. F. et al. Catabolism of 4-hydroxy-acids and 4-hydroxynonenal via 4-hydroxy-4-phosphoacyl-CoAs. *J. Biol. Chem.* 284, 33521-33534 (2009). Harris, S. R. et al. Metabolism of levulinate in perfused rat livers and live rats: Conversion to the drug of abuse 4-hydroxypentanoate. *J. Biol. Chem.* 286, 5895-5904 (2011). The proposed pathway is shown in FIG. 3. First, LA is activated as a coenzyme A-thioester, levulinyl-CoA (LA-CoA). Second, LA-CoA is reduced to 4-hydroxyvaleryl-CoA (4HV-CoA). Third, 4HV-CoA is phosphorylated at the γ-position to yield 4-phosphovaleryl-CoA (4PV-CoA). Fourth, 4PV-CoA is dephosphorylated to yield a pentenoyl-CoA species (likely 3-pentenoyl-CoA). Last, pentenoyl-CoA is hydrated to yield 3-hydroxyvaleryl-CoA (3HV-CoA) which can be further oxidized via β-oxidation to yield acetyl-CoA and propionyl-CoA or incorporate 3HV-CoA into PHA polymers.

TABLE 2

*P. putida* LA Operon Knockout and Complementation

| Genotype | Predicted Function | Growth on LA EV | Growth on LA Complement | Growth on 4HV EV | Growth on 4HV Complement |
|---|---|---|---|---|---|
| WT | | ++ | N/A | ++ | N/A |
| ΔlvaR (PP_2790) | $\sigma^{54}$ dependent sensory box protein | − | ++ | − | ++ |
| ΔlvaA (PP_2791) | Phosphotransferase family | − | ++ | − | ++ |
| ΔlvaB (PP_2792) | Hypothetical protein | − | ++ | − | ++ |
| ΔlvaC (PP_2793) | acyl-CoA dehydrogenase family protein | − | ++ | + | ++ |
| ΔlvaD (PP_2794) | short chain dehydrogenase/reductase family | − | ++ | ++ | ++ |
| ΔlvaE (PP_2795) | Acyl-CoA synthetase | ++ | ++ | − | + |

Figures 4A, 4B:
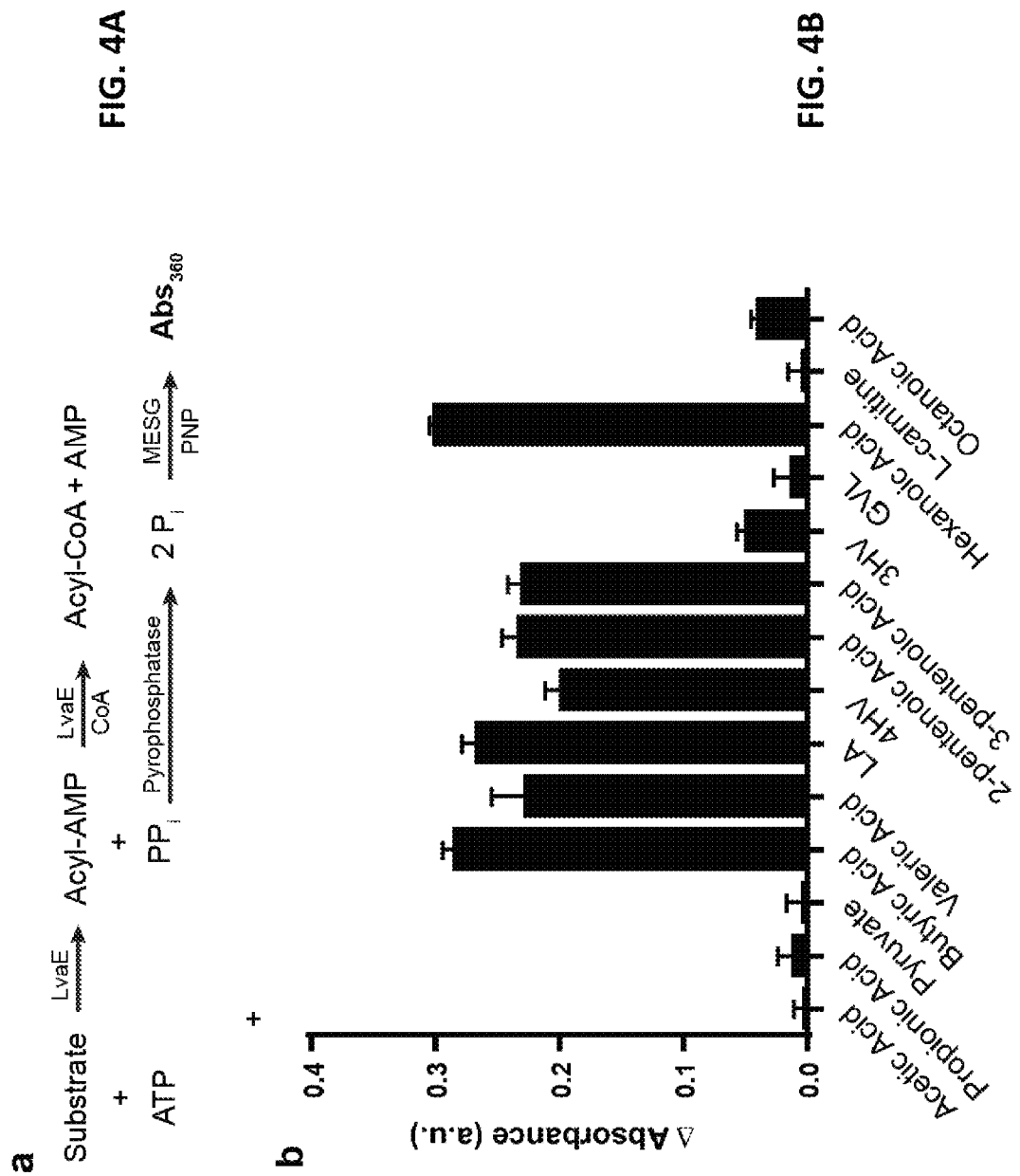
FIG. 4A is a schematic of CoA-ligase activity assay. Using the Enzchek®-brand Pyrophosphatase Assay kit, the amount of pyrophosphate released during the CoA ligase reaction was measured as an increase of absorbance at 360 nm.
FIG. 4B depicts the results of the LvaE CoA-Ligase activity towards a variety of short and medium chain acids (n=3). Baseline subtraction was performed on all samples with a control reaction containing no substrate, indicated by Δ absorbance. Error bars represent standard deviation.
Figure 5A:
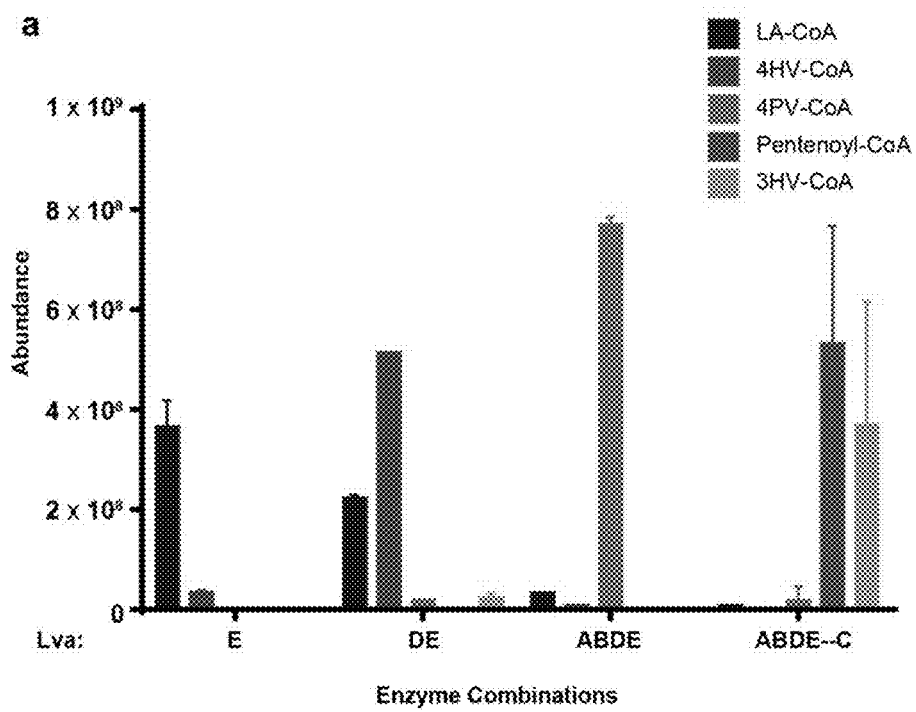
FIG. 5A and FIG. 5B depict CoA species abundance in LC/MS analysis of in vitro enzyme combinations.
Figure 5B:
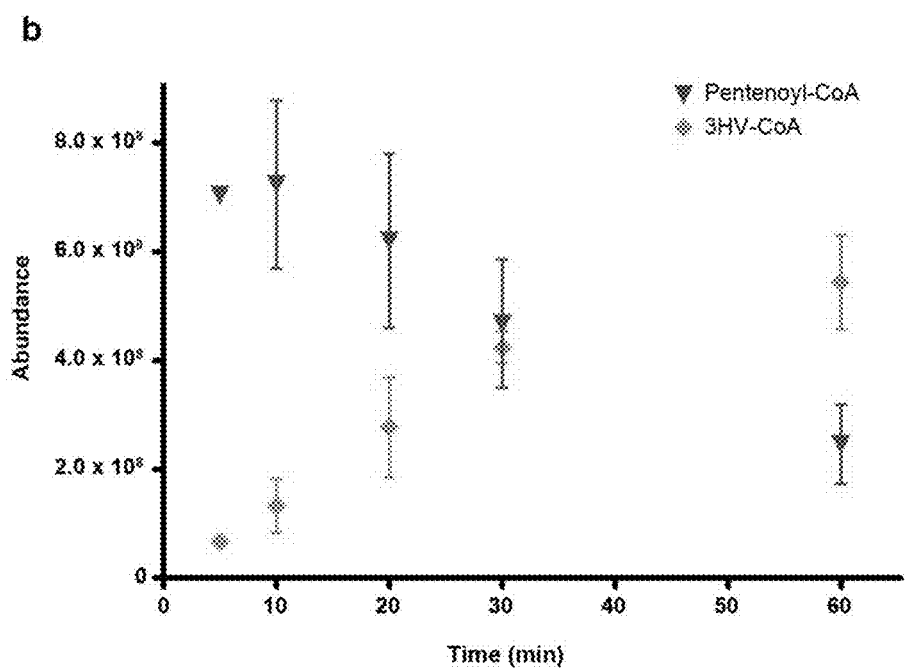

(EV) empty vector plasmid;
(N/A) not applicable;
(−) No growth;
(+) Visible growth;
(++) Robust growth lvaE The presence of an enzyme (encoded by lvaE) with homology to an acyl-CoA synthetase (including a putative CoA binding region and an AMP binding site) suggested that the degradation pathway acts on CoA thioesters and begins with the activation of acids to acyl-CoA's. The ΔlvaE strain grew on LA but not on 4HV, indicating that LA may also be activated by other CoA-synthetases in *P. putida*. The activity of purified LvaE (6x-His N-terminal fusion) was quantified on a variety of organic acid substrates using the EnzChek®-brand Pyrophosphate Assay Kit (Molecular Probes, Eugene, OR) which detects pyrophosphate released in the first half reaction to creating the acyl-AMP intermediate. See FIG. 4A for a schematic. LvaE demonstrated activity on C4-C6 carboxylic acids, including LA and 4HV (see FIG. 4B), but showed minimal activity on other organic acids (pyruvate, acetate, propionate, octanoate). Using LC/MS to detect reaction products, it was demonstrated that LvaE was necessary and sufficient to catalyze the ligation of CoA to LA, generating levulinyl-CoA (LA-CoA). See FIGS. 5A and 5B. None of the other enzymes from the operon catalyzed this or any other reaction using LA as a substrate (data not shown), confirming that the pathway proceeds via acyl-CoA intermediates.

lvaD

The second step in the proposed pathway is the reduction of LA-CoA to 4HV-CoA which is predicted to be catalyzed by lvaD. lvaD is annotated as an oxidoreductase containing an NADH binding domain and was found to be required for growth on LA but not necessary for growth on 4HV. See Table 2. LvaD was purified in a similar manner to LvaE but used an N-terminal maltose binding protein (MBP) tag to increase the solubility of the enzyme. Fox, J. D., Routzahn, K. M., Bucher, M. H. & Waugh, D. S. Maltodextrin-binding proteins from diverse bacteria and archaea are potent solubility enhancers. *FEBS Lett.* 537, 53-57 (2003). The in vitro reaction containing LvaD and LvaE verified that LvaD is involved in the production of 4HV-CoA. See FIG. 5A. Furthermore, LvaDE was the only enzyme combination capable of generating 4HV-CoA in vitro (data not shown). LvaD can catalyze the reduction of LA-CoA with either NADH or NADPH (data not shown).

lvaAB

It was hypothesized that the third intermediate would be 4-phospho-valeryl-CoA (4PV-CoA) based off its observation in LA degradation in rat livers. (Zhang et al. and Harris et al., supra.) The first gene in the operon, lvaA, has putative homology regions, including an ATP binding site that associated it with the kinase superfamily and phosphotransferase family of enzymes. The second protein in the operon (LvaB) has no listed function and is predicted to be only 12 kDa in size. Orthologous sequence alignments of lvaB reveal that in all other organisms this hypothetical protein is located immediately downstream of an lvaA ortholog. Therefore, a pull down experiment was used to determine if the two proteins interact. Striebel, F. et al. Bacterial ubiquitin-like modifier Pup is deamidated and conjugated to substrates by distinct but homologous enzymes. *Nat. Struct. Mol. Biol.* 16, 647-651 (2009). Yamamoto, S. & Kutsukake, K. FliT acts as an anti-F1hD2C2 factor in the transcriptional control of the flagellar regulon in *Salmonella enterica* serovar *typhimurium*. *J. Bacteriol.* 188, 6703-8 (2006).

LvaA was N-terminally tagged with MBP and cloned into a pET expression vector. LvaB was cloned directly downstream of LvaA as it is found in *P. putida*'s native genome sequence. The recombinant proteins were expressed in *E. coli* BL21 (DE3) and purified using the MBP tag. A SDS-page gel of the eluent contained two bands at 85 kDa and 12 kDa, closely matching the predicted sizes of MBP-LvaA and untagged LvaB respectively. Liquid chromatography tandem mass spectrometry was done on a trypsin digest of the 12 kDa band and identified the protein sequence to be LvaB (data not shown).

Growth studies of deletion mutants revealed that lvaA and lvaB are both required for growth on either LA or 4-HV. This supports the hypothesis that they are involved in a reaction after the conversion of LA-CoA to 4HV-CoA. To confirm that the association between LvaA and LvaB is important for enzymatic activity, the following enzymatic combinations were tested: i) LvaA, LvaD and LvaE, ii) LvaB, LvaD, and LvaE, iii) LvaAB, LvaD and LvaE. A decrease of 4HV-CoA and an increase of the predicted 4PV-CoA intermediate was seen only when all four of the enzymes were present. See FIG. 5A. Tandem mass spectrometry was used to verify the identity of 4PV-CoA. See FIGS. 6A, 6B, 6C, and 6D. We compared the MS/MS spectrum of 4HV-CoA (FIG. 6A; assignment of selected fragments shown in FIG. 6B) and the MS/MS spectrum of 4PV-CoA (FIG. 6C; assignment of selected fragments shown in FIG. 6D) and detected major ion fragments at m/z 786.191, 537.106 and 519.095 (4HV-CoA) and 866.158, 617.072 and 599.061 (4PV-CoA). For each compound, these fragments can be assigned to the cleavage of a P—O bond, an O—C bond and the dehydration of O—C cleaved product, respectively (FIGS. 6B and 6D). Both compounds are fragmenting at the same bonds, but the resulting m/z values for the daughter ions differ by 79.967. This mass corresponds to the m/z of $PO_3H^-$, supporting the existence of the phosphorylated 4HV-CoA species, 4PV-CoA.

lvaC

The final step in the hypothesized pathway is the formation of 3HV-CoA. Given that the combination of LvaABDE was responsible for generating 4PV-CoA and no 3HV-CoA was detected in these reactions, it was postulated that LvaC was responsible for the final conversion steps. LvaC has homology to the dehydrogenase family of enzymes and 30% amino acid sequence identity to the *E. coli* acyl-CoA dehydrogenase protein. The ΔlvaC strain was unable to grow on LA, but grew weakly on 4HV. LvaC was purified as an MBP fusion and the resulting protein pellet displayed a yellow hue. This is often indicative of a co-purified flavin and an absorbance scan of the protein revealed absorbance maxima that are consistent with a flavin co-factor (data not shown). When the LvaC sample was treated with trichloroacetic acid and centrifuged, a white protein pellet and a yellow hued supernatant were observed (data not shown). This indicates that the co-factor was not covalently bound to LvaC. Dijkman, W. P. & Fraaije, M. W. Discovery and characterization of a 5-hydroxymethylfurfural oxidase from Methylovorus sp. strain MP688. *Appl. Environ. Microbiol.* 80, 1082-1090 (2014).

When LvaC was added to the in vitro reaction mixture, the concentrations of reaction intermediates (LA-CoA, 4HV-CoA, 4PV-CoA) were reduced while the abundance of 3HV-CoA and a pentenoyl-CoA species increased. See FIG. 5A. This species is likely either 2-pentenoyl-CoA and/or 3-pentenoyl-CoA, which could not be resolved with the methods used. Both compounds eluted at the same retention time with the same molecular mass. To test if LvaC is solely responsible for the conversion of 4PV-CoA to 3HV-CoA, a two-step reaction was used. First, we performed the LvaABDE reaction with LA, CoA, ATP, NAD(P)H and separated the CoA products from the enzymes. To the enzyme-free mixture, we added LvaC without additional co-factors. After 30 min, we observed signals for both pentenoyl-CoA and 3HV-CoA. This indicated that the putative oxidoreductase, LvaC, is responsible for both the removal of the phosphate group to produce the enoyl-CoA and the hydration of the enoyl to the 3-hydroxyl compound.

To reconstitute the entire pathway, a time course reaction with all five Lva enzymes and LA as the starting substrate was performed. Over time, a rapid increase in pentenoyl-CoA was observed followed by a slow disappearance that mirrored the increase in the 3HV-CoA signal. See FIG. 5B. This suggests that the hydration reaction may be the limiting step in the overall pathway.

lvaFG

Based on homology alignments, lvaG is predicted to encode a protein with 95% amino acid sequence identity to a *Pseudomonas aeruginosa* cation acetate symporter and lvaF shares 33% amino acid sequence identity with the *E. coli* inner membrane protein Yhjb (BLAST). Sequence alignments of lvaF orthologs indicate that lvaF and lvaG are found with the same spatial relationship to each other in many organisms (data not shown). These proteins are likely involved in organic acid transport but are unlikely to be involved in the catabolism of LA given that they were not necessary for the enzymatic conversion of LA to 3HV-CoA in vitro.

Conferring Growth on Levulinic Acid to *E. coli* LS5218

To demonstrate the ability of the lvaABCDE to enable LA catabolism, we transformed *Escherichia coli* LS5128 [fadR601, atoC(Con)], a common strain used in studies of organic acid catabolism, with a plasmid linking LvaABCDE expression to an anhydrotetracycline inducible promoter (pJMR5). See Jenkins, L. S. & Nunn, W. D. Genetic and molecular characterization of the genes involved in short-chain fatty acid degradation in *Escherichia coli*: the ato system. *J Bacteriol* 169, 42-52 (1987). This strain failed to grow when cultured in minimal LA media. Adaptive evolution of this strain yielded two mutants that grew robustly on media with LA as the sole carbons source. The two mutants had three common mutations 1.) an altered RBS controlling LvaA translation, 2.) a disruption in fadE, and 3.) a disruption in atoC. See Table 8 in the Examples. Freshly created deletion mutants harboring pJMR32 (a variant of pJMR5 with a putative strong RBS) demonstrated that the fadE deletion and the atoC deletion were both beneficial. These deletions likely prevent side reactions catalyzed by FadE and AtoDA (activated by AtoC) that compete with the desired catabolic flux to central metabolism.

Thus described herein is an operon responsible for assimilating LA into the β-oxidation pathway of *P. putida*. Through an integrated genetic and in vitro biochemistry study, it has been demonstrated herein that the genes lvaABCDE are upregulated in the presence of LA and are sufficient for the conversion of LA to 3HV-CoA, an intermediate of native β-oxidation. Removing any enzyme from the reaction mixture abolished 3HV-CoA production, indicating all five genes are necessary for this pathway. The biochemical assays confirmed the presence of 4PV-CoA, an intermediate previously observed in the metabolism of LA in rat livers. In sum, the pathway consumes at least two (2) ATP and one reducing equivalent to produce 3HV-CoA. See the pathway in FIG. 3. β-oxidation of 3HV-CoA to acetyl-CoA and propionyl-CoA would recover the reducing equivalent. Given the energy demands of the pathway, growth on LA should be performed aerobically or in the presence of an alternative electron acceptor to enable ATP synthesis via respiration.

Like many catabolic pathways, expression of the lva operon is regulated by the presence of the pathway substrates. Using a transcriptional reporter assay, we demonstrated that the lva operon is upregulated by a transcriptional activator encoded by the divergent lvaR gene. Additionally, we suspect that the lva operon is also regulated by Crc, a global carbon catabolite repressor. Crc is an mRNA binding protein that prevents protein translation when bound to a specific mRNA sequence in *P. putida*, AAnAAnAA. This sequence pattern is found immediately upstream of lvaE (data not shown), which encodes an acyl-CoA synthetase that initiates the pathway. The presence of the Crc target sequence suggests that the operon is also subject to *P. putida*'s carbon catabolite repression system which may explain the diauxic growth curves observed for mixtures of glucose and LA.

Figures 7A, 7B:
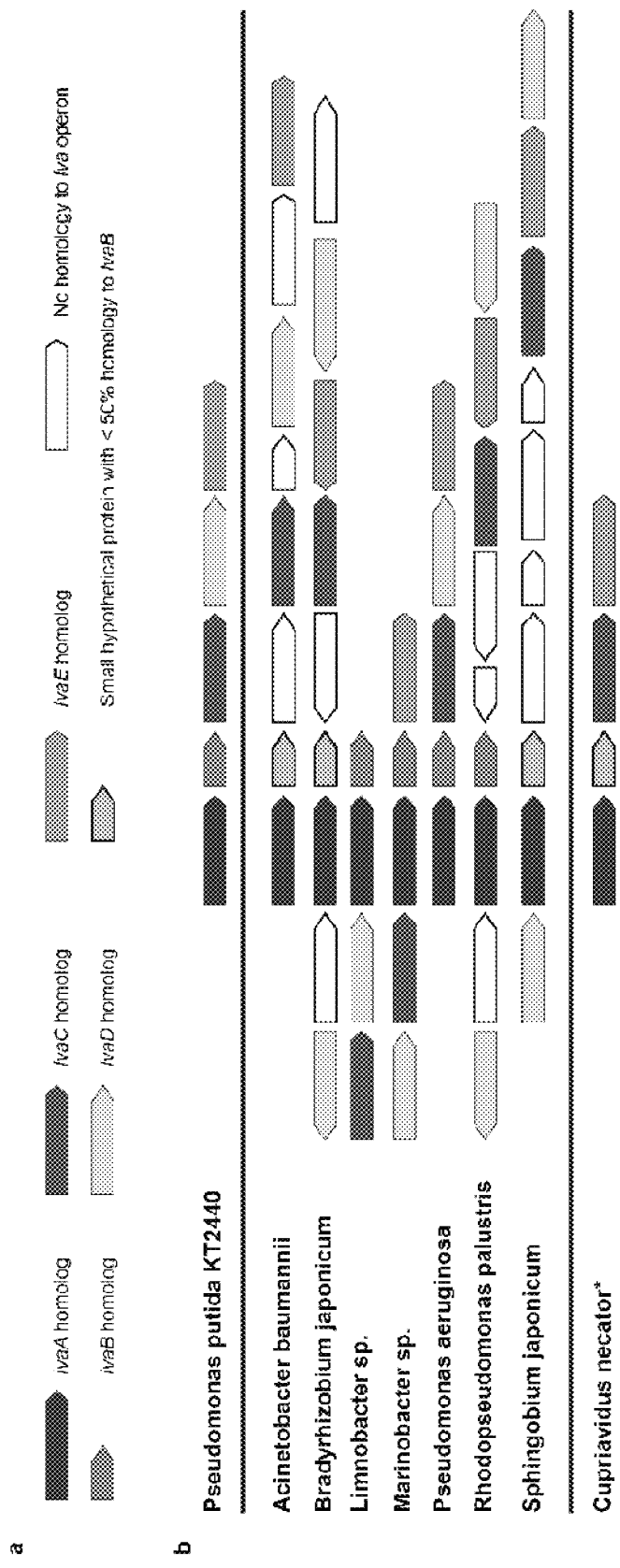
FIG. 7A is a representation of lva operon enzymatic genes.
FIG. 7B is a comparison of LA degradation gene clusters found in other organisms.

The lva operon is highly conserved among the various *Pseudomonas* species (data not shown). Gene clusters comprised of the main enzymatic proteins can also be found in a variety of alpha-, beta- and gamma-proteobacteria, graphically represented in FIGS. 7A and 7B. The alpha-proteobacteria species (*Azospirillum, Bradyrhizobium, Rhodopseudomonas, Sphingobium*) are primarily isolated from soil environments, similar to *Pseudomonas putida*. The beta-proteobacteria species (*Azoarcus, Limnobacter*) and the gamma-proteobacteria species (*Acinetobacter, Marinobacter*) are isolated from both soil and ocean environments. *Cupriavidus nector* contains a gene cluster comprised of potential LvaACE homologs, and additionally possesses in that same cluster a small hypothetical protein which could be a functional homolog of LvaB.

Interestingly, the isomerization of 4HV-CoA to 3HV-CoA in *P. putida* proceeds through a phosphorylated intermediate, 4PV-CoA, a compound also observed in a study of LA metabolism in rat livers. Harris et al., supra. This study suggested the 3HV-CoA was generated via a pathway comprised of complex phosphorylated intermediates. We did not detect MS peaks corresponding to any of these compounds in our in vitro reaction mixtures. Without being limited to any underlying mechanism, and based on changes we observed in total ion abundance over time, we propose that 4PV-CoA is dephosphorylated to an enoyl-CoA and subsequently rehydrated to 3HV-CoA. We suspect that the phosphorylation of 4HV-CoA by LvaAB generates a better leaving group and makes the subsequent dehydration more thermodynamically favorable. However, the mechanism for these last steps remains unclear.

The time course measurements that we collected for the full reaction indicate that the formation of the pentenoyl-CoA happens fairly quickly, but the transition from the pentenoyl-CoA to the 3HV-CoA is a much slower reaction. See FIG. 5B. Our tests indicate that LvaC is capable of converting 4PV-CoA to 3HV-CoA, but those reactions still contain a higher abundance of pentenoyl-CoA compared to 3HV-CoA. A more detailed mechanistic study of the final steps may clarify the specific role of lvaC.

Understanding how LA metabolism works is important because LA is a common byproduct of biomass hydrolysis and is often present in the final feedstock. High concentrations of LA in the feedstock can lead to microbial inhibition and represents an underused source of carbon in traditional sugar fermentations. By discovering the catabolic pathway, the present method is useful to engineer microbes capable of detoxifying the media and/or utilizing LA as a source of carbon, thereby maximizing the overall carbon conversion from biomass into high value products. Additionally, identifying the structure of LA metabolism will improve metabolic models and enable pathway design for novel LA-based bioconversions.

Converting LA to 2-Butanone

Converting LA catalytically to the solvent 2-butanone (methyl ethyl ketone, MEK) has been reported as feasible, but the approach suffers from energy intensive process conditions and low yields. Serrano-Ruiz, J. C., West, R. M. & Dumesic, J. A. Catalytic Conversion of Renewable Biomass Resources to Fuels and Chemicals. *Annu. Rev. Chem. Biomol. Eng.* 1, 79-100 (2010). 2-butanone has been produced biologically through the dehydration of 2,3 butanediol with a vitamin B12 dependent diol dehydratase. Yoneda, H., Tantillo, D. J. & Atsumi, S. Biological production of 2-butanone in *Escherichia coli*. *Chem Sus Chem* 7, 92-95 (2014). The direct decarboxylation of LA (a five carbon γ-ketoacid) into 2-butanone has been demonstrated using acetoacetate decarboxylase (adc) from *Clostridium acetobutylicum* as a biocatalyst, but the enzyme is susceptible to substrate inhibition, limiting its overall productivity. Min, K. et al. Conversion of levulinic acid to 2-butanone by acetoacetate decarboxylase from *Clostridium acetobutylicum*. *Appl. Microbiol. Biotechnol.* 97, 5627-5634 (2013).

Using the pathway for LA catabolism, lvaABCDE, in *P. putida* and the expression of short chain fatty degradation pathways, we evolved two strains of *E. coli* for utilization of LA as a carbon substrate. The evolved strains were derived from E. coli LS5218, which contains specific mutations for overexpression of β-oxidation (fadR601) and short chain fatty acid degradation genes [atoC(Con)]. The draft LS5218 genome assembly is GCA_002007165.1. We sequenced the genome of the mutants and isolated two key functional deletions required for LA growth. Reconstitution of the isolated mutations in wild type LS5218 revealed one, fadE, to be beneficial. Another mutation (in atoC) also conferred a beneficial growth phenotype. Neither mutation is necessary for growth on LA. Using these strains as a basis, we engineered production of butanone by expressing an acetoacetyl-CoA transferase (AtoDA) and an acetoacetate decarboxylase (ADC) in conjunction with LvaABCDE. Our first-generation engineered strains produced 140 mg/L of butanone from LA.

Evolving E. coli for Growth on LA

Figure 8:
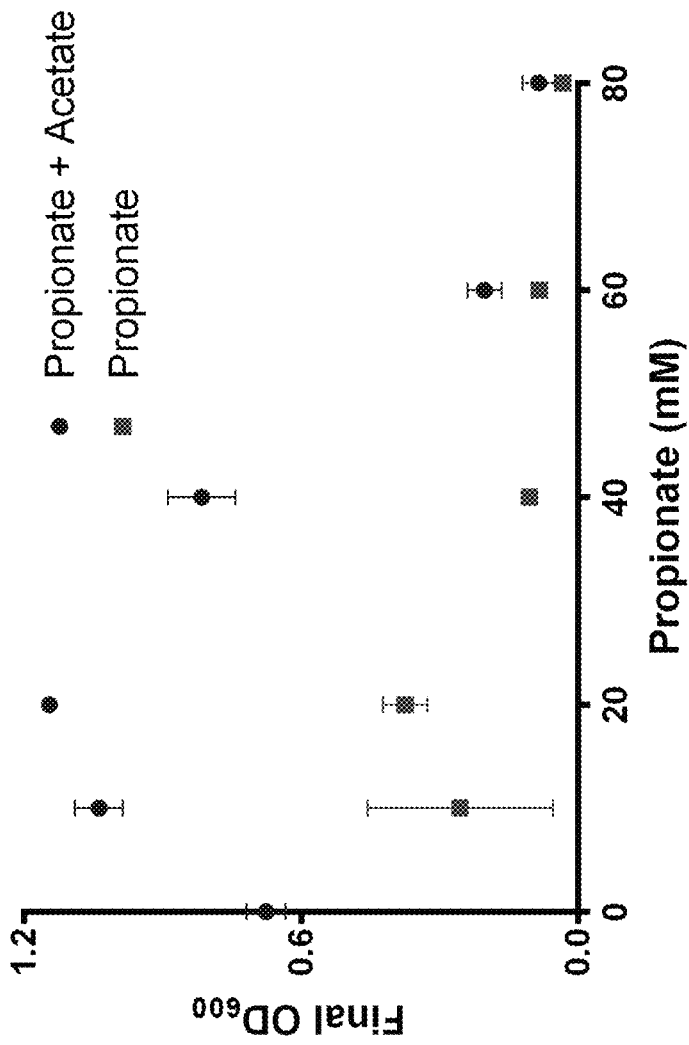
FIG. 8 is a graph showing E. coli MG1655 growth with propionate using minimal media supplemented with propionate or propionate and acetate.

LA is a five carbon acid that degrades into equal moles of acetyl-CoA and propionyl-CoA, and while E. coli contains the necessary genes for propionyl-CoA metabolism, increased propionyl-CoA concentrations are known to be inhibitory. Man, W. J., Li, Y., O'Connor, C. D. & Wilton, D. C. The Binding of Propionyl-Coa and Carboxymethyl-Coa to Escherichia-Coli Citrate Synthase. Biochim. Biophys. Acta 1250, 69-75 (1995). Therefore, we performed a growth study on wild type E. coli MG1655 to evaluate its capability towards propionate catabolism and investigated the growth of E. coli on various concentrations of propionate, with and without acetate as a secondary carbon source. The maximum allowable concentration that stimulated growth was 20 mM propionate, both in the presence and absence of acetate, before growth inhibition was observed. See FIG. 8. Using this information, we designed all LA growth experiments to contain maximum concentration of 20 mM LA to minimize false negative growth phenotypes resulting from propionate toxicity.

Five biosynthetic enzymes are required for catabolizing LA into a common β-oxidation intermediate, encoded by the lva operon from Pseudomonas putida, and lvaABCDE were expressed as an operon in E. coli LS5218 from the plasmid pJMR5. We hypothesized that this combination of expressed enzymes would confer LA catabolism in E. coli, however, initial tests on LA as a sole carbon source did not produce a positive growth phenotype. We then performed a sub-culturing experiment to evolve a strain capable of LA catabolism. The first rounds were conducted with both LA and acetate as available carbon to stimulate growth and allow cells to adapt to the presence of LA. We observed an increase in final cell density with the both carbon sources present compared with the acetate only control, and subsequent culturing was done with LA as the sole carbon source. After 14 rounds of sub-culturing on LA, we isolated two mutant strains, M141 and M142, capable of LA catabolism.

We purified the plasmid, pJMR5, and sequenced it to determine if evolutionary changes were due to plasmid mutations. A mutation in the ribosome binding sequence (RBS) for the lvaABCDE operon was discovered (Table 8), and corresponded to an increase in the predicted strength compared with original sequence. We retransformed the isolated plasmid, designated p2, into wild type LS5218 and the resulting strain did not have the LA growth phenotype, indicating genomic mutations were also necessary (data not shown). To isolate the essential genomic mutations, we submitted strains M141 and M142 for whole genome sequencing after curing out the plasmid. The sequencing results highlighted four mutations in M141 and three mutations in M142 when compared with the genome sequence assembled for wild type E. coli LS5218, with only two common mutations between both strains (Table 8). The common mutations were a point mutation in fadE that resulted in a premature stop codon causing a functional deletion and the insertion of transposons into atoC that also resulted in a premature stop codon and a functional deletion.

Developing Engineered Strain of E. coli that Catabolizes LA

Figure 9:
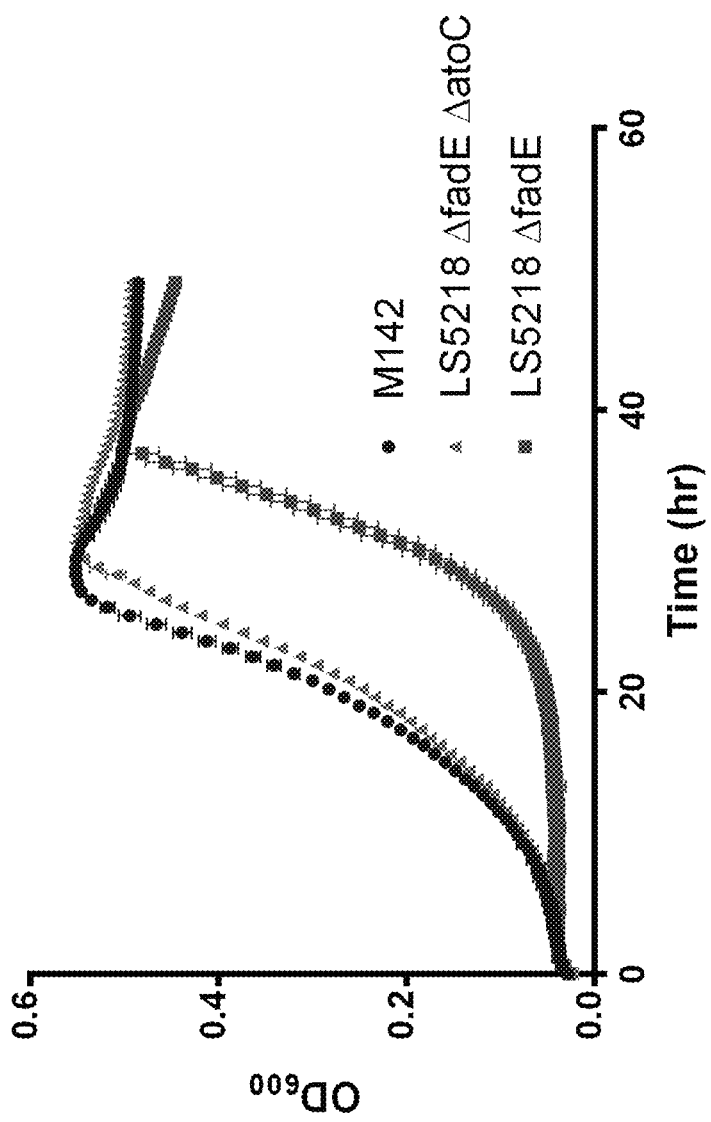
FIG. 9 is a growth curve of LS5218 strains on LA.

We verified the functional deletion mutations by generating clean knockouts of fadE and atoC as single knockouts and a combined knockout strain using CRISPR-Cas9 mediated genome engineering. We transformed each strain with the plasmid pJMR32, a redesigned pJMR5 with increased RBS strength for LvaA. We examined growth on LA as a sole carbon source for each strain. Wild type LS5218 and LS5218 ΔatoC were unable to grow on LA where as LS5218 ΔfadE and LS5218 ΔatoC ΔfadE grew using LA as the sole carbon source and strain M142 with pJMR32 was used as a positive control. We generated growth curves on LA for strains LS5218 ΔfadE, LS5218 ΔatoC ΔfadE and M142 and found that LS5218 ΔfadE has a significantly longer lag period then LS5218 ΔatoC ΔfadE and M142. See FIG. 9.

In a follow up experiment, the host cell was an E. coli strain in which the lva operon (under aTc induction) and the E. coli fadBA (under IPTG induction) were overexpressed in the host cell. This cell was able to grow on LA without deleting fadE. (Data not shown.) This result indicates that fadBA overexpression is beneficial for E. coli growth on LA. To induce fadBA overexpression in E. coli, fadR is deleted to deregulate those genes (which also deregulates fadE). Therefore, in the preferred host cells, if fadR is deleted, then fadE should also be deleted to minimize competing side reactions. If fadR is not deleted, then overexpression of fadBA is preferred because it maximizes butanone production.

Establishing Butanone Production

Figure 10:
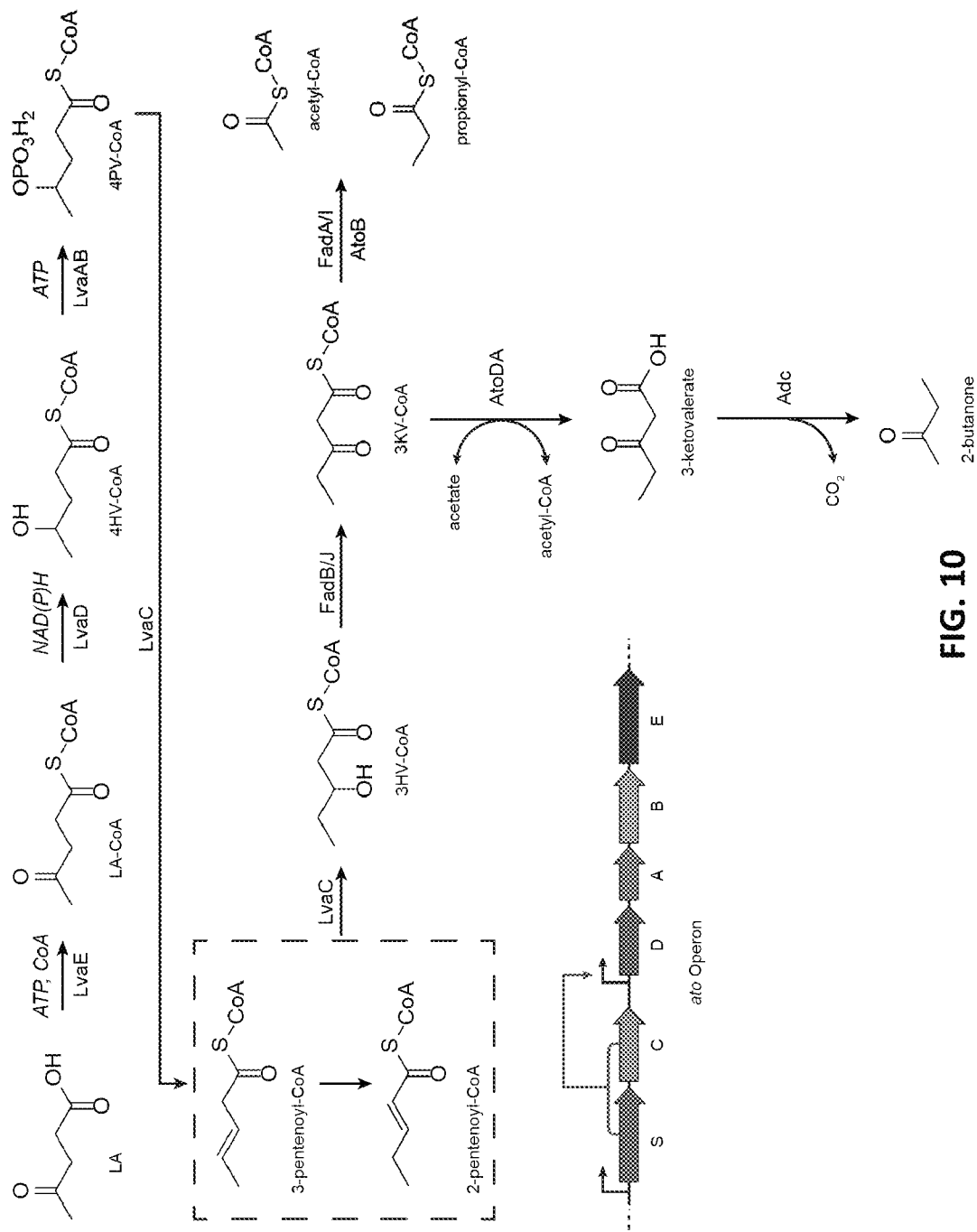
FIG. 10 depicts the production pathway for 2-butanone.

Unlike the previously reported schemes for the production of 2-butanone, we proposed that 2-butanone could be produced through a similar pathway as acetone production. In Clostridium acetobutylicum, acetone is produced through the condensation of two acetyl-CoA molecules to acetoacetyl-CoA (a β-ketoacyl-CoA), which can be liberated to acetoacetate by a CoA transferase and then decarboxylated to acetone by acetoacetate decarboxylase. Our strategy for producing 2-butanone is depicted in FIG. 10. First, LA is catabolized to 3-hydroxyvaleryl-CoA (3HV-CoA) through P. putida enzymes encoded by lvaABCDE. Then a 3-hydroxyacyl-CoA dehydrogenase (encoded by fadB) oxidizes 3HV-CoA to 3-ketovaleryl-CoA (3 KV-CoA) followed by the transfer of CoA from 3 KV-CoA to acetate to form of 3-ketovalerate through an acetoacetyl-CoA transferase (encoded by atoDA). This conversion can also be accomplished using a short-chain thioesterase or a succinyl-CoA transferase. Finally, acetoacetate decarboxylase (encoded by adc from C. acetobutylicum) converts 3-ketovalerate into butanone and $CO_2$.

Figure 11:
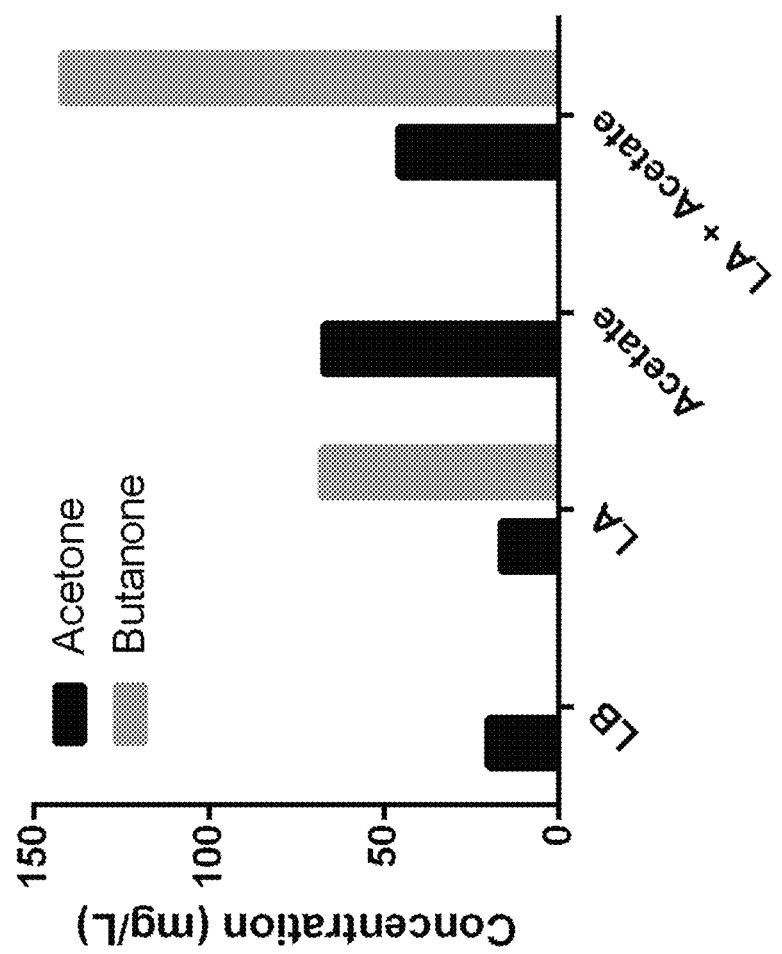
FIG. 11 is a histogram showing Acetone and butanone production from eMEK1 containing lvaABCDE and adc. Media consists of LB supplemented with LA, acetate or LA and acetate. (n=1).

The lvaABCDE and adc genes were co-expressed from the plasmids pJMR32 and pJMR95, respectively. The plasmid pJMR95 is a medium copy plasmid containing the $P_{trc}$ promoter and an origin compatible with pJMR32. Chromosomal overexpression of atoDA genes resulted from the atoC(Con) mutation in host strain E. coli LS5218. To verify the validity of the proposed butanone production pathway, we tested butanone production in the non-optimized strains, eMEK1 (LS5218 ΔfadE) and eMEK12 (LS5218 ΔfadE ΔatoC), containing plasmids pJMR32 and pJMR95. For our experiment, we grew the strains in rich media (LB), added 20 mM of acetate, LA, or both carbons and examined the supernatant for acetone and butanone after 24 hours. We found that eMEK12 was incapable of producing either ketone species, and eMEK1 could produce butanone only in the presence of LA. See FIG. 11. eMEK1 produced up to 140 mg/L of butanone when both LA and acetate were supplied.

Figure 12:
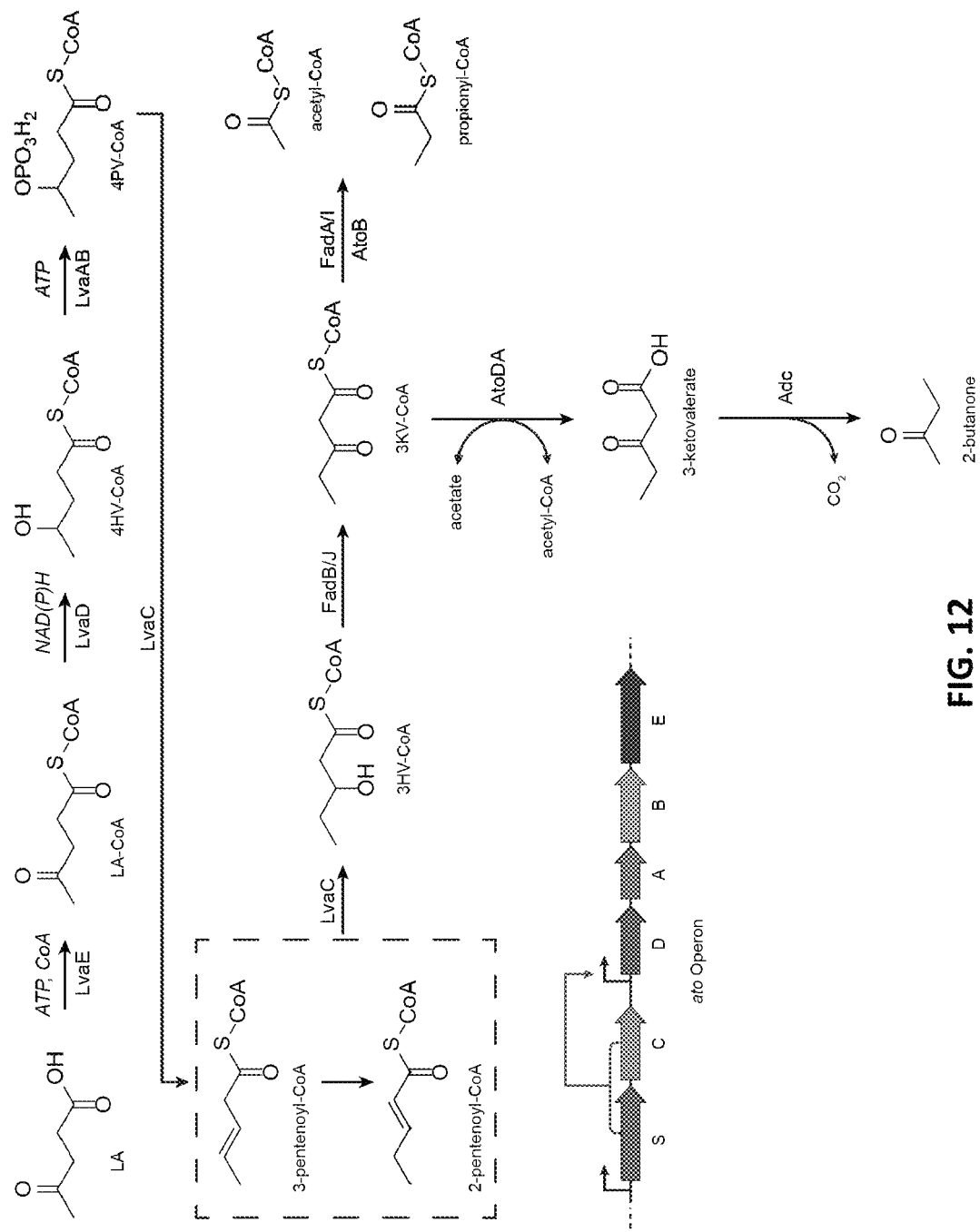
FIG. 12 shows the optimized 2-butanone production with competing thiolase pathways deleted (strain eMEK4).
Figure 13B:
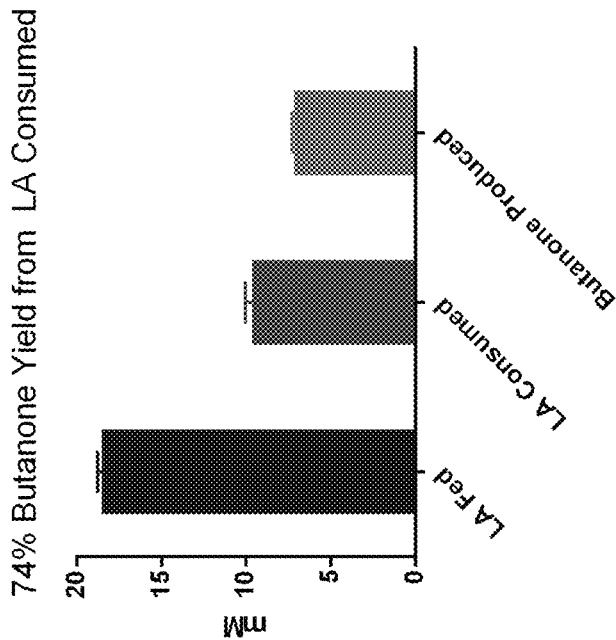
FIG. 13B shows butanone yield from LA consumed. Media consisted of LB supplemented with acetate or LA and acetate.
Figure 13A:
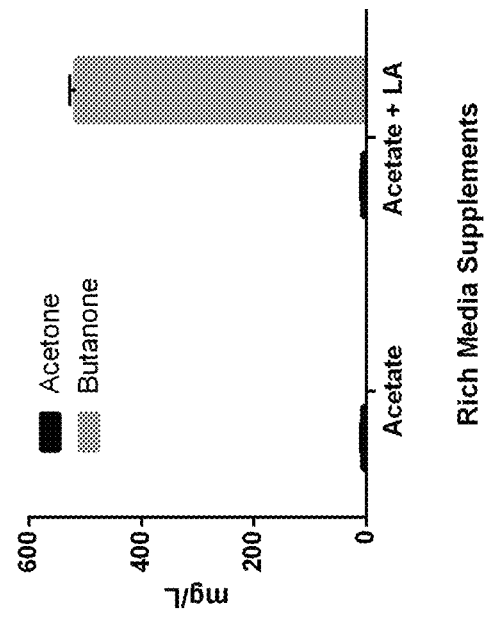
FIG. 13A shows acetone and butanone production from eMEK4 containing lvaABCDE and adc.

To increase flux of LA towards butanone production and to reduce the formation of acetone, we deleted the competing degradation pathways. We removed the thiolase enzymes encoded by fadA, fadI and atoB to delete the competing degradation pathways for LA catabolism and increase LA flux towards butanone production. See FIG. 12. We tested butanone and acetone production in a more optimized strain, eMEK4 (LS5218 ΔfadEAIJ ΔatoB), using pJMR95 (adc from *C. acetobutylicum*) and pJMR32-Cm (lvaABCDE with chloramphenicol resistance). This strain did not show an appreciable amount of acetone production and was capable of producing 500 mg/L butanone when both LA and acetate were supplied. See FIGS. 13A and 13B. We also calculated the yield of butanone from LA and determined a 74% measurable yield, indicating we are very close to the theoretical maximum.

Discussion and Future Directions

The catabolic pathway for LA in *P. putida* indicated that the last steps in the pathway were undertaken by enzymes involved in β-oxidation. We hypothesized that expression of lvaABCDE in *E. coli* LS5218, which carries mutations for β-oxidation overexpression, would directly confer *E. coli* growth on LA. That assumption was proven incorrect. The deletion of fadE is beneficial to allow LS5218 a growth phenotype on LA. FadE is an acyl-CoA dehydrogenase enzyme that catalyzes the formation of the a trans-2-enoyl-CoA from an acyl-CoA compound. Because the LA catabolic pathway terminates at the formation of 3HV-CoA, the final steps to be completed by the *E. coli* β-oxidation pathway would only involve fadBA, so it remains unclear as to why a fadE is beneficial. We hypothesize that FadE may be active towards LA-CoA, adding a double bond at the 2 position of the γ-ketovaleryl-CoA species and sequestering the molecule from further degradation, however, this is hypothesis is speculative. FadE is an inner membrane protein, thereby complicating efforts to purify an active enzyme and making it hard to ascertain the true nature behind the cellular activity of fadE. Detailed metabolite analysis of LS5218 with lvaABCDE grown in the presence of acetate and LA may reveal insight to the mode of inhibition caused by FadE expression.

The deletion of atoC was not a necessary mutation, but did confer a growth benefit. This mutation was isolated during through the directed evolution process because we were screening for mutants with reduced lag phases, thereby enriching our mutant population with strains containing the early termination sequence. Constitutive activation of the ato regulon by the atoC(Con) mutation in LS5218 causes an overexpression of an acetoacetyl-CoA transferase (encoded by atoDA), an acetyl-CoA acetyltransferase (encoded by atoB) and a short chain fatty acid transporter (encoded by atoE). We propose that the 3-ketovaleryl-CoA intermediate was diverted from the final cleavage step into central metabolites by AtoDA, releasing 3-ketovalerate. The sequestering of LA as 3-ketovalerate reduces overall carbon flow to central metabolites, stunting growth of the *E. coli* strains until they can adapt for the utilization of 3-ketovalerate. Reducing expression of AtoDA through the deletion of atoC would prevent the formation of the secondary pathway, allowing direct flux of LA to central metabolites. Additionally, AtoE is a short chain fatty acid transporter and overexpression could be causing an increase in the intracellular concentration of LA above a threshold LS5218 is capable of tolerating, causing an extended lag phase. Monitoring intracellular metabolites during the extended lag phase could be useful in isolating the exact cause when compared with the ΔatoC strains.

Figure 14:
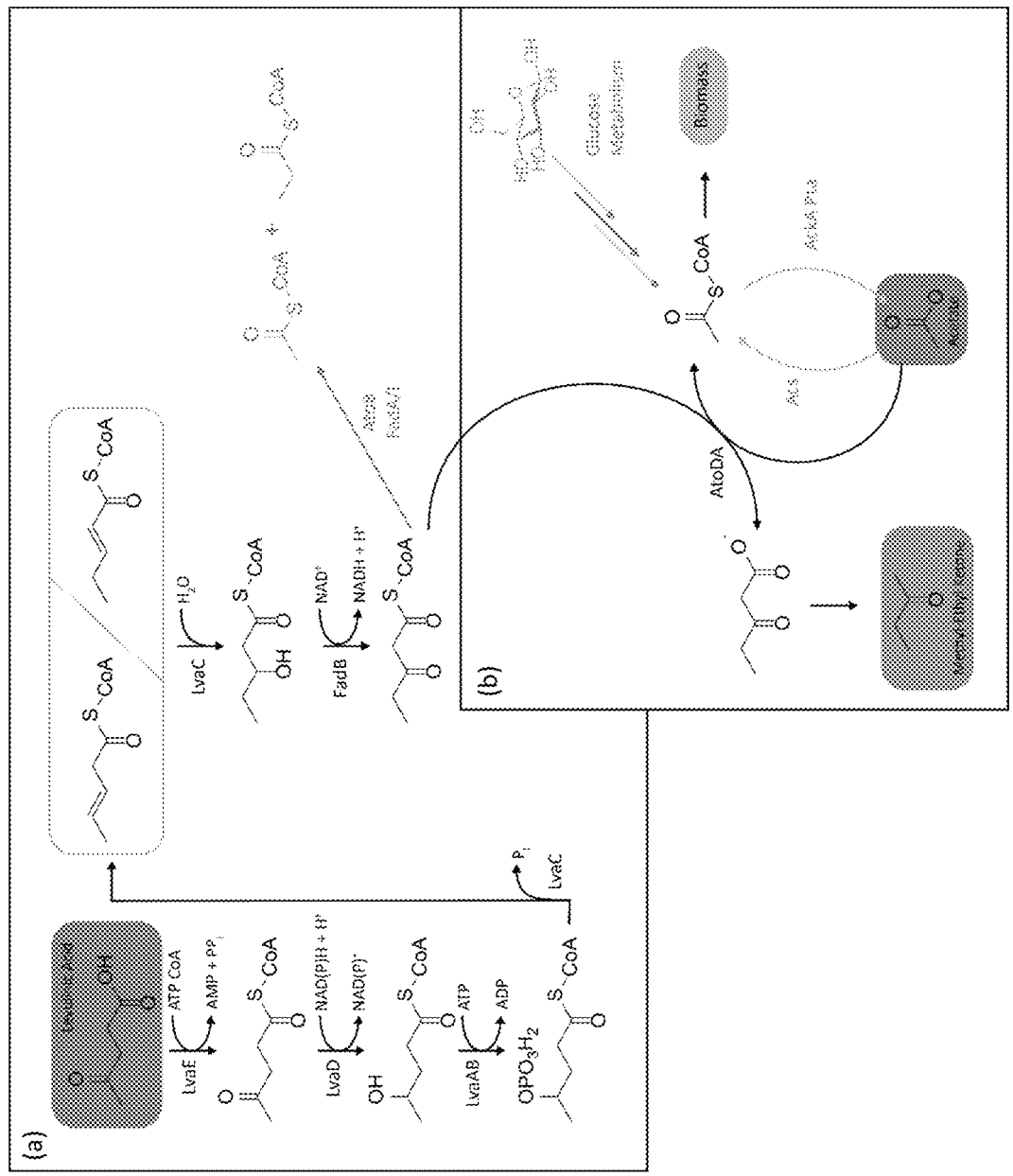
FIG. 14 depicts growth coupling of acetate utilization and MEK production.

We have demonstrated herein that butanone can be produced from our novel pathway at a final concentration of at least 500 mg/L, which is on par with the previously reported bioconversion processes. Because atoDA encode for a CoA transferase instead of a thioesterase, a short chain acid, such as acetate, is required as a substrate along with 3 KV-CoA to produce 3-ketovalerate and acetyl-CoA. In order to optimize the utilization of acetate for the direct formation of 2-butanone, we propose to couple the uptake of acetate with the CoA transferase reaction. Deleting the CoA forming acetyl-CoA synthetase (Acs) and the Pta (phosphotransacetylase) and Ack (acetate kinase) should limit the routes for acetate uptake and couple acetate uptake with 3-ketovalerate production. See FIG. 14.

Figure 15A:
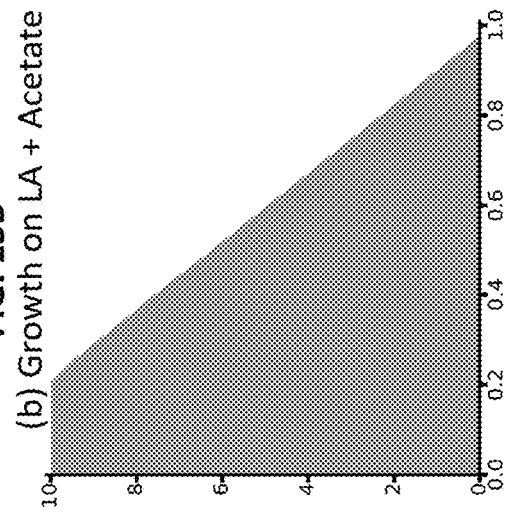
FIGS. 15A, 15B, 15C, and 15D depict predicted phase planes from metabolic modeling for MEK production.
Figure 15B:
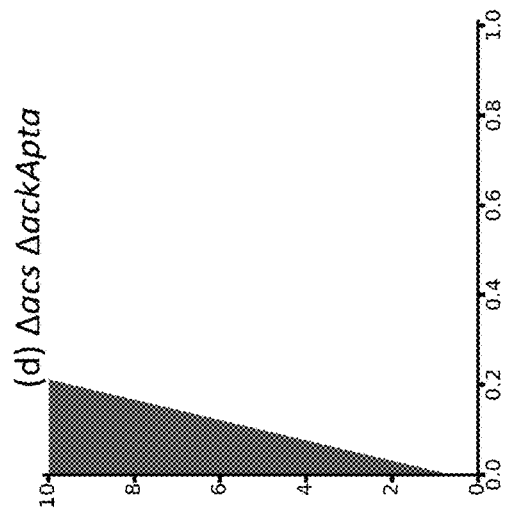

By adding the LA catabolism pathway to the iJO1366 model of *E. coli* metabolism with a maximum uptake rate of 10 mmol gDW$^{-1}$ hr$^{-1}$, we were able to model the growth of *E. coli* using LA as its sole carbon source with a predicted growth rate of 0.71 hr$^{-1}$. By adding reactions for the acetoacetyl-CoA transferase (acting on 3 KV-CoA) and acetoacetate decarboxylase (acting on 3-ketovalerate), we saw a nearly direct trade-off between 2-butanone production and biomass production, with no butanone production at the limit of maximum growth rate (0.71 hr$^{-1}$) and no growth at the limit of maximum butanone production (9.4 mmol gDW$^{-1}$ hr$^{-1}$). See FIG. 15A. Adding externally supplied acetate increases the maximum predicted butanone production rate to 10 mmol gDW$^{-1}$ hr$^{-1}$ (complete conversion) by allowing *E. coli* to grow on acetate and convert all LA to butanone. See FIG. 15B.

Figure 15C:
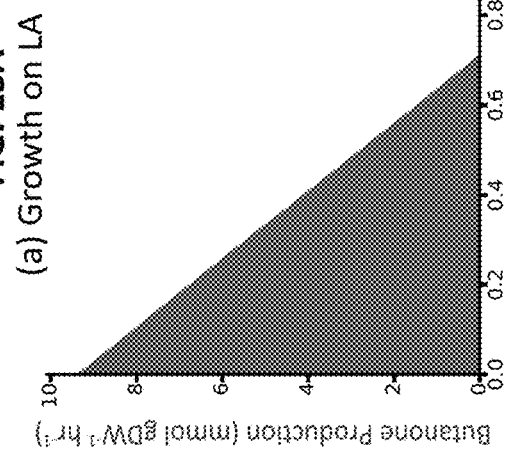
Figure 15D:
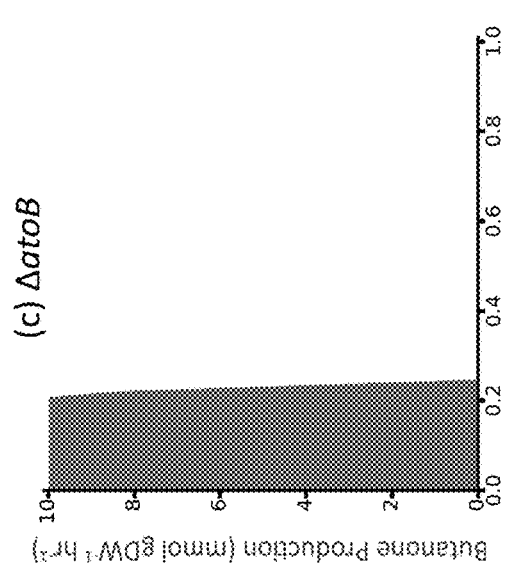

To prevent LA from being used as a carbon source, we knocked-out the reaction corresponding to AtoB, which decreased the maximum predicted growth rate to 0.24 hr$^{-1}$ while maintaining the maximum predicted 2-butanone production rate to 10 mmol gDW$^{-1}$ hr$^{-1}$. See FIG. 15C. It is important to note that, because the iJO1366 model does not include reactions for odd-chain β-oxidation, the in silico deletion of β-oxidation-related reactions was not necessary. We then extended this to a growth-coupled strategy for which *E. coli* is required to produce butanone to grow. By knocking out acetate fermentation (reactions ACKr and PTAr) and acetyl-CoA synthesis from acetate (reaction ACS), the only way for *E. coli* to make acetyl-CoA is by transferring a CoA from 3HV-CoA to exogenously supplied acetate. In this case, a maximum predicted 2-butanone production rate of 10 mmol gDW$^{-1}$ hr$^{-1}$ is achieved (complete bioconversion) simultaneously with the maximum predicted growth rate of 0.21 hr$^{-1}$. See FIG. 15D. This demonstrates the possibility of a growth-coupled direct bioconversion of LA to butanone.

Figure 16:
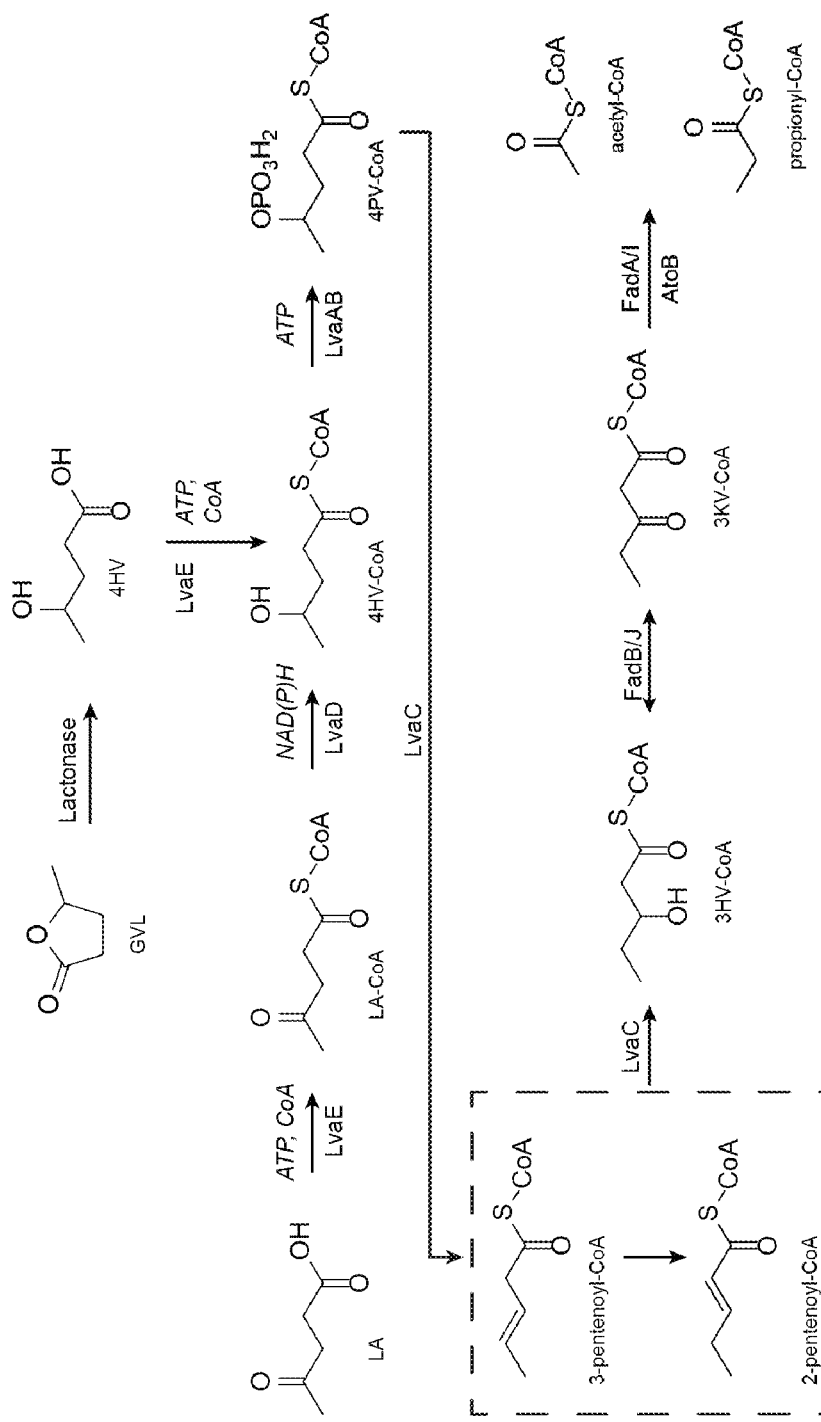
FIG. 16 depicts the proposed pathway for GVL degradation through ring opening via lactonase activity. 4HV, 4-hydroxyvalerate; GVL, γ-valerolactone.

GVL is a derivative of LA that can be produced from a hydrogenation and a dehydration reaction and has been shown to be an effective green solvent in the dissolution of lignocellulosic biomass. See Alonso, D. M., Wettstein, S. G. & Dumesic, J. A. Gamma-valerolactone, a sustainable platform molecule derived from lignocellulosic biomass. *Green Chem.* 15, 584 (2013); Luterbacher, J. S. et al. Nonenzymatic Sugar Production from Biomass Using Biomass-Derived gamma-Valerolactone. *Science* (80-.). 343, 277-281 (2014); and Luterbacher, J. S. et al. Lignin monomer production integrated into the γ-valerolactone sugar platform. *Energy Environ. Sci.* 8, 2657-2663 (2015). As a lactone species, GVL is susceptible to ring opening under basic conditions where it forms 4-hydroxyvalerate, an intermediate in the levulinic acid catabolic pathway. See FIG. 16. Though most bacteria do not thrive under basic pH conditions, some bacteria contain enzymes called lactonases that enzymatically open lactone rings into the corresponding acid. See Ng, F. S. W., Wright, D. M. & Seah, S. Y. K. Characterization of a phosphotriesterase-like lactonase from *Sulfolobus solfataricus* and its immobilization for disruption of quorum sensing. *Appl. Environ. Microbiol.* 77, 1181-1186 (2011); Onakunle, 0. a., Knowles, C. J. & Bunch, a. W. The formation and substrate specificity of bacterial lactonases capable of enantioselective resolution of racemic lactones. *Enzyme Microb. Technol.* 21, 245-251 (1997); and Carlier, A., Chevrot, R., Dessaux, Y. & Faure, D. The assimilation of gamma-butyrolactone in *Agrobacterium tumefaciens* C58 interferes with the accumulation of the N-acyl-homoserine lactone signal. *Mol. Plant. Microbe. Interact.* 17, 951-7 (2004). We hypothesize that *P. putida* can be engineered for GVL catabolism if a lactonase with activity towards γ-lactones is heterologously expressed.

Lactones often exist in nature as N-acyl homoserine lactones, a common component of bacterial quorum sensing systems, and as a defense mechanism many bacteria have evolved lactonases to cleave the lactone structure, which can work towards quench the sensing signal. See Uroz, S., Dessaux, Y. & Oger, P. Quorum sensing and quorum quenching: The Yin and Yang of bacterial communication. *Chem Bio Chem* 10, 205-216 (2009); Chow, J. Y. et al. Directed evolution of a thermostable quorum-quenching lactonase from the amidohydrolase superfamily. *J. Biol. Chem.* 285, 40911-20 (2010); and Hiblot, J., Gotthard, G., Chabriere, E. & Elias, M. Structural and enzymatic characterization of the lactonase SisLac from *Sulfolobus islandicus*. *PLoS One* 7, e47028 (2012). Due to quorum sensing responses often being linked with pathogenicity, the function of various classes of lactonase have been studied extensively. (Id.) We have compiled a list of five lactonases with reported activity towards γ-lactones, or GVL specifically: *Bacillus thuringiensis* (protein AiiA), *Rhodococcus erythropolis* (protein QsdA), *Sulfolobus islandicus* (protein SisLac), *Deinococcus radiodurans* (protein DrPLL), and *Geobacillus kaustophilus* HTA426 (protein GKL).

Preliminary experiments have shown that three of the selected lactonases (DrPLL, GKL, and QsdA) have activity towards degrading GVL and when heterologously expressed in *P. putida* can confer growth on GVL as a sole carbon source. GVL is capable of supporting *P. putida* growth, but this growth is severely hindered by an extended lag phase when compared with the related carbon sources of LA and 4HV (data not shown). Directed evolution on GVL media could produce a faster metabolic strain and genomic sequencing could isolate key mutations.

We anticipate that integration of the LA catabolic pathway in a heterologous host can expand the possibilities for biological upgrading of a renewable carbon source. Our proposed approaches presented here represent direct bioconversions, where all LA flux is routed through our production pathways. LA can also be used as an alternative source of intracellular propionyl-CoA, which is a starting molecule for odd chain fatty acids and select secondary metabolites. As a common product produced through the chemical hydrolysis of biomass, catabolizing LA can promote production of a variety of chemicals that normally require an exogenous feedstock and help move us towards environmental sustainability.

Directed Evolution of *E. coli* L55218

See Examples section for cells types and chemicals. *E. coli* was grown at 37° C., unless otherwise stated. Subculturing experiments were done with a volume of 5 ml in glass test tubes (20×150 mm, Fisher Scientific) with 250 rpm agitation in a 126 shaker (New Brunswick Scientific). Starting media contained 20 mM LA and 40 mM acetate or 40 mM acetate only for negative control. Cultures were grown for 72 hours and optical density (OD) measurements taken with a Spectronic 20 (Milton Roy Company), then culture were diluted 1:100 into fresh media. Once the OD in the LA and acetate cultures exceeded the OD of the acetate only cultures, further growth media was 20 mM LA only. These cultures were incubated until turbidity was observed visually, then diluted 1:100 into fresh media. This occurred for a total of 14 dilutions steps in LA media, spanning two weeks.

Plasmids were prepped (QIAprep® Miniprep Kits, Qiagen) and sequenced (Functional Biosciences) to find mutations. Plasmids were cured out of mutate strains through serial culturing in rich media (LB broth) and patch plated on LB and $LB_{kan50}$.

Genome Engineering with CRISPR-Cas9

CRISPR/Cas recombineering was performed following the outlined protocol in Mark Politz's Thesis (Appendix C). See Politz, M. C. Transcription Activator-Like Effectors as Tools for Prokaryotic Synthetic Biology. (University Of Wisconsin-Madison, 2016). This involves the use of the plasmid pMP11, which contains constitutive expression of *S. pyogenes* cas9, arabinose-inducible λ Red genes, aTc inducible guide RNA (gRNA) targeted to pBR322 ori, temperature sensitive SC101 ori and $Amp^R$. The plasmid containing the gRNA sequence was designated pgRNA and derived from pgRNA-bacteria. Qi, L. S. et al. Repurposing CRISPR as an RNA-guided platform for sequence-specific control of gene expression. *Cell* 152, 1173-1183 (2013). *E. coli* strains containing pMP11 were at 30° C. (due to the temperature sensitive origin) overnight in LB and diluted into fresh SOB media (Green & Sambrook) with arabinose in the morning. Cultures were grown to an OD of 0.4-0.6 and then cells were made electrocompetent. Competent cells were transformed with the pgRNA plasmid and a linear DNA repair template and selected for on LB containing kanamycin and ampicillin. Following colony PCR, correct strains were cured of the pgRNA plasmid by growing overnight in $LB_{Amp}$ and induced with aTc. pMP11 was cured out of strains by growing overnight at 42° C.

Butanone Production

Butanone production was tested in strains containing pJMR32 (lvaABCDE) and pJMR95 (adc). Media was comprised of LB broth supplemented with 20 mM LA or 33 mM acetate, accordingly. Production runs were performed for 24 hours with 5 ml in glass test tubes (20×150 mm, Fisher Scientific) with 250 rpm agitation in a 126 shaker (New Brunswick Scientific). Supernatant was filter sterilized and run on Restek Stabilwax-DA column (60 m, 0.53 mm ID) with a GC-FID (Shimadzu). Protocol for GC-FID: 40° C. (hold for 4 min) to 250° C. at 5° C./min, $H_2$ constant flow, linear velocity 40 cm/sec. Injection and detector temperature was 250° C. Minimal media was prepared according to the batch medium recipe by Korz et al. (Korz et al (1995) "Simple fed-batch technique for high cell density cultivation of *Escherichia coli.*," *J. Biotechnol.* 39, 59-65. Riesenberg et al (1991) "High cell density cultivation of *Escherichia coli* at controlled specific growth rate," *J. Biotechnol.* 20, 17-27. doi:10.1016/0168-1656(91)90032-Q.) Ferric ammonium citrate was substituted for Fe(III) citrate. Hereafter this media is referred to as Riesenberg-Korz (RK) media. Kanamycin was used at final concentration of 50 µg/mL and carbenicillin was used at a final concentration of 100 µg/mL.

Plasmid construction was completed using Phusion® High Fidelity DNA Polymerase (NEB) for PCR reactions and Gibson assembly. (Gibson et al. (2009) Enzymatic assembly of DNA molecules up to several hundred kilobases," *Nat. Methods* 6, 343-5.) Gibson reaction mixtures (2 µL) were transformed into chemically competent *E. coli* DH5a and cells were plated on LB media with the appropriate antibiotics. Plasmids were verified by sequencing of the cloning junctions.

EXAMPLES

Chemicals, Strains, and Media

All chemicals were obtained from Sigma-Aldrich or Fisher Scientific. Bacterial strains and plasmids used in this study are summarized in Table 3. Strains and plasmids are listed in Table 3. *E. coli* strains were grown at 37° C. and *P. putida* strains were grown at 30° C. unless otherwise noted. Kanamycin was used at final concentration of 50 µg/ml. 5-Fluorouracil was used at a final concentration of 20 µg/mL.

4-hydroxyvalerate was made through the saponification of γ-valerolactone (GVL). See Martin, C. H. & Prather, K. L. J. High-titer production of monomeric hydroxyvalerates from levulinic acid in *Pseudomonas putida*. *J. Biotechnol.* 139, 61-67 (2009). The pH of 2M GVL was increased to a pH of 12, using 10 M sodium hydroxide (NaOH), and incubated for 1 hour. For use in bacterial growth conditions, 4HV stocks were adjusted to a pH of 8 using 5 M HCl. Plasmid construction was completed using Phusion®-brand High Fidelity DNA Polymerase (New England Biolabs Inc., Ipswich, MA) for the PCR reactions and Gibson assembly. See Gibson, D. G. et al. Enzymatic assembly of DNA molecules up to several hundred kilobases. *Nat. Methods* 6, 343-5 (2009). *P. putida* genomic DNA sequences retrieved from NCBI database, with the following designations: PP_2791, lvaA; PP_2792, lvaB; PP_2793, lvaC; PP_2794, lvaD; PP_2795, lvaE; PP_2790, lvaR. 2 µL of the Gibson reaction mixture was transformed into chemically competent *E. coli* DH5a cells and plated on appropriate media. Minimal media was prepared from the following references: M9 minimal media was made according to Green and Sambrook and MOPS minimal media was made according to Neidhardt et al. Kanamycin was used at final concentration of 50 µg/ml. 5-Fluorouracil was used at a final concentration of 20 µg/mL. See Green, M. R. and Sambrook, J., *Molecular Cloning: A Laboratory Manual (Fourth Edition)*, Cold Spring Harbor Laboratory Press, 2012, ISBN-10: 1936113422 and Neidhardt, F. C., Bloch, P. L. & Smith, D. F. Culture medium for enterobacteria. *J. Bacteriol.* 119, 736-747 (1974).

TABLE 3

Strains and Plasmid List

| Strain/Plasmid | Relevant genotype/property | Source or Reference |
|---|---|---|
| Strains | | |
| *Pseudomonas putida* | | |
| KT2440 | Wild Type | ATCC 47054 |
| KTU | Δupp | Altenbuchner et al., *Appl. Environ. Microbiol.* 77, 5549-52 (2011) |
| ΔlvaR | Δupp ΔPP_2970 | This work |
| ΔlvaA | Δupp ΔPP_2971 | This work |
| ΔlvaB | Δupp ΔPP_2972 | This work |
| ΔlvaC | Δupp ΔPP_2973 | This work |
| ΔlvaD | ΔPP_2974 | This work |
| ΔlvaE | Δupp ΔPP_2975 | This work |
| *Escherichia coli* | | |
| CC118λpir | Δ(ara-leu), araD, ΔlacX174, galE, galK, phoA, thi1, rpsE, rpoB, argE (Am), recA1, lysogenic λpir | de Lorenzo et al., *BMC Microbiol.* 11, 38 (2011). |
| DH5α | F⁻ Φ80lacZΔM15 Δ(lacZYA-argF) U169 recA1 endA1 hsdR17 ($r_k^-$,$m_k^+$) phoA supE44 thi-1 gyrA96 relA1 λ⁻ | Invitrogen (Waltham, MA, USA) |
| MG1655 | F⁻ λ⁻ ilvG⁻ rfb-50 rph-1 | Coli Genetic Stock Center ("CGSC"), Yale University, 266 Whitney Avenue, New Haven, CT, USA |
| LS5218 | F⁺ λ⁺ fadR601 atoC512(Const) | CGSC |
| M141 | LS5218 mutant evolved on LA | This work |
| M142 | LS5218 mutant evolved on LA | This work |
| ΔfadE | LS5218 ΔfadE | This work |
| ΔfadE | LS5218 ΔfadE ΔatoC | This work |
| Plasmids | | |
| pBAM1 | tnpA, Amp$^R$, Kan$^R$, oriR6K | de Lorenzo et al. |
| pJOE6261.2 | upp (from *P. putida*) Kan$^R$, ColE1 origin | Altenbuchner et al. |
| pJOE-lvaR | pJOE6261.2 with up- and downstream regions of lvaR | This work |

TABLE 3-continued

Strains and Plasmid List

| Strain/Plasmid | Relevant genotype/property | Source or Reference |
| --- | --- | --- |
| pJOE-lvaA | pJOE6261.2 with up- and downstream regions of lvaA | This work |
| pJOE-lvaB | pJOE6261.2 with up- and downstream regions of lvaB | This work |
| pJOE-lvaC | pJOE6261.2 with up- and downstream regions of lvaC | This work |
| pJOE-lvaE | pJOE6261.2 with up- and downstream regions of lvaE | This work |
| pBAD35 | $P_{BAD}$ promoter, $Kan^R$, pBBR1 origin | Lennen et al., Biotechnol. Bioeng. 106, 193-202 (2010) |
| pBAD-lvaA | pBAD35 carrying lvaA | This work |
| pBAD-lvaB | pBAD35 carrying lvaB | This work |
| pBAD-lvaC | pBAD35 carrying lvaC | This work |
| pBAD-lvaD | pBAD35 carrying lvaD | This work |
| pBAD-lvaE | pBAD35 carrying lvaE | This work |
| pK18mobsacB | sacB, $Kan^R$, pMB1 origin | Schafer et al., Gene 145, 69-73 (1994). |
| pK18-lvaD | pK18mobsacB containing up- and downstream regions of lvaD | This work |
| pJMR74 | pBAD35 with $P_{BAD}$ promoter and araC replaced with lvaA promoter and lvaR (P. putida) carrying sfGFP | This work |
| pBbS2k-mCherry | $Kan^R$, SC 101 ori, $P_{Tet}$ promoter, mCherry | Addgene, 75 Sidney St. #550A, Cambridge, MA, USA) |
| pJMR5 | pBbS2k carrying lva operon in front of mCherry | This work |
| p2 | pJMR5 mutant evolved on LA | This work |
| pJMR32 | pJMR5 with increased RBS for lva operon, mCherry removed | This work |

Transposon Library and Screening

The transposon library was created following a protocol adapted from Martinez-Garcia et al. Martinez-Garcia, E., Calles, B., Arévalo-Rodríguez, M. & de Lorenzo, V. pBAM1: an all-synthetic genetic tool for analysis and construction of complex bacterial phenotypes. BMC Microbiol. 11, 38 (2011). Suicide vector delivery was achieved through bi-parental mating. Overnights of P. putida KT2440 and E. coli CC118λpir with pBAM1 were grown with appropriate antibiotics. From overnight cultures, 1 mL of cells was pelleted by centrifugation, washed with 10 mM $MgSO_4$, and resuspended in 1 mL of 10 mM $MgSO_4$. Cells were mixed in a 1:1 ratio into a final volume of 1 mL 10 mM $MgSO_4$, with the final concentration of each strain at an $OD_{600}$ of 0.03 ($3\times10^7$ cells). The mixture was concentrated down to 30 μL and plated on 0.22 μm filter paper. The filter paper was incubated for 16 hrs on LB agar plates at 30° C. After incubation, the filter paper was removed from the plate and transferred into a 1.5 mL microfuge tube with 1 mL of 10 mM $MgSO_4$. The cells were resuspended through vortexing and plated onto kanamycin selective M9 citrate plates, to isolate P. putida cells with transposon insertions. P. putida transposon library was screened by replica plating colonies from the M9 citrate plates onto LB, M9 glucose and M9 LA plates supplemented with kanamycin. Positive hits were identified as colonies that exhibited growth on LB and glucose plates but not on LA plates.

RNA Extraction

Wild type P. putida KT2440 cells were grown in MOPS minimal media supplemented with 20 mM LA to $OD_{600}$ 0.8. 10 OD-mL were collected by centrifugation at 5000×g for 10 minutes at 4° C. in Beckman Coulter Allegra X-15R. The supernatant was decanted and the pellet frozen at −80° C. for 24 hrs. The RNA extraction protocol is adapted from Pinto et al. Pinto, F. L., Thapper, A., Sontheim, W. & Lindblad, P. Analysis of current and alternative phenol based RNA extraction methodologies for cyanobacteria. BMC Mol. Biol. 10, 79 (2009). The frozen pellet was thawed, resuspended in 1.5 mL Trizol and transferred to a 2.0 mL microfuge tube. The suspension was incubated for κ minutes at 95° C. and then for 5 minutes on ice. After the incubation, 300 μL chloroform was added and the tube shaken vigorously for 15 seconds. The Trizol-chloroform mixture was incubated at room temperature for 15 minutes and then centrifuged for 15 minutes at 12000×g and 4° C. The upper phase was transferred to a fresh tube and an equal volume of isopropanol was added. This mixture was incubated for 10 minutes at room temperature and then centrifuged for 10 minutes at 12000×g and 4° C. The supernatant was discarded and the pellet resuspended in 1 mL of 75% ethanol. This was centrifuged for 5 minutes at 8000×g and 4° C. The supernatant was discarded, the pellet air dried for 3 minutes and then resuspended in 100 uL RNase-free water and stored at −80° C.

Transcription Start Site Isolation

The transcription start site for genes lvaR and lvaA were isolated using an adapted 5' Race protocol from Schramm et al. Schramm, G., Bruchhaus, I. & Roeder, T. A simple and reliable 5'-RACE approach. Nucleic Acids Res 28, E96 (2000). The RNA isolated from P. putida KT2440 was treated with the TURBO DNA-Free™ Kit from Invitrogen, catalog no. AM1907 (a subsidiary of ThermoFisher Scientific, Waltham, MA) to remove any contaminating DNA. The Promega GoScript-brand RT PCR kit was used to generate cDNA using 1 μL of a 10 μM gene specific oligo (JMR2 for lvaR and JMR287 for lvaA) instead of the random oligo mixture. (Promega Corporation, Madison, WI) Following the inactivation of the reverse transcriptase, the cDNA was purified using Qiagen PCR Purification kit. (Qiagen Inc., Germantown, MD.) Tailing of the cDNA was achieved using the terminal deoxynucleotidyl transferase (TdT) enzyme from ThermoFisher Scientific. The final reaction mixture contained 1× reaction buffer, 1 pmol cDNA fragments, 60 pmol dGTP or dCTP and 30 U TdT. The reaction was incubated at 37° C. for 15 minutes and then quenched by heating to 70° C. for 10 minutes and the tailed cDNA fragments cleaned up using a Qiagen PCR Purification kit. The tailed cDNA was amplified using GoTaq®-brand Green Master Mix (Promega) with an annealing temperature of 55° C. and an extension time of 30 seconds. Primer GG318 was used for dGTP tailing and ALM244 was used for dCTP tailing. The reverse primer for lvaR was JMR150 and for lvaA was JMR296. The resulting PCR product was submitted for sequencing.

Polycistronic Verification

Using the DNAse treated RNA isolated from LA grown *P. putida* KT2440, cDNA for the operon was generated with the Promega GoScript-brand RT PCR kit using 1 μL of a 10 μM gene specific oligo (JMR237). The cDNA was then used as the template for PCR reactions using GoTaq Green Master Mix with an annealing temperature of 55° C. and an extension time of 0:30 seconds. Primers used for each gene are given in Table 4.

TABLE 4

Primer List

| Primer Name | Sequence | Function |
|---|---|---|
| *5'Race primers* | | |
| JMR2 | AACCTGGACGGTGAAGAGCG (SEQ. ID. NO: 11) | Reverse primer for lvaR cDNA |
| JMR287 | GAACGGACAGGAAGCACAG (SEQ. ID. NO: 12) | Reverse primer for lvaA cDNA |
| GG318 | GGCCACGCGTCGACTAGTACC CCCCCCCCCC (SEQ. ID. NO: 13) | Amplification primer for dGTP tailing reactions |
| ALM244 | GGCCACGCGTCGACTAGTACGGGH HGGGHHGGGHHG (SEQ. ID. NO: 14) | Amplification primer for dCTP tailing reactions |
| JMR150 | CCAATGCCCGTAGCAGGTCGC (SEQ. ID. NO: 15) | Reverse primer for lvaR |
| JMR296 | GAACTCCTGTTCACGGTCAAG (SEQ. ID. NO: 16) | Reverse primer for lvaA |
| *Operon cDNA Reverse Transcription Primer* | | |
| JMR237 | TCAATGATCGACGGCACCG (SEQ. ID. NO: 17) | Reverse primer for operon cDNA |
| *Operon-individual genes* | | |
| JMR3 | ACGCTGTGCTTCCTGTCCGTT (SEQ. ID. NO: 18) | lvaA Forward |
| JMR325 | GTTCTTCACCGGACAGATGG (SEQ. ID. NO: 19) | lvaA Reverse |
| JMR576 | CCCACGAATTGCTCGAGATC (SEQ. ID. NO: 20) | lvaB Forward |

TABLE 4-continued

Primer List

| Primer Name | Sequence | Function |
|---|---|---|
| JMR577 | GCAGGTCGGGCAATGTCG (SEQ. ID. NO: 21) | lvaB Reverse |
| JMR290 | CATGCCCGTTCGTGCTTC (SEQ. ID. NO: 22) | lvaC Forward |
| JMR572 | CAGGTCCATCATGTTGTCGGC (SEQ. ID. NO: 23) | lvaC Reverse |
| JMR330 | ACGAGCCGTGAGGACATCT (SEQ. ID. NO: 24) | lvaD Forward |
| JMR293 | CGAGCGCAACTTGTCACC (SEQ. ID. NO: 25) | lvaD Reverse |
| JMR294 | GCTGGTGTGCATCAACATCC (SEQ. ID. NO: 26) | lvaE Forward |
| JMR571 | GCAGTGGAACATCGGCAAGG (SEQ. ID. NO: 27) | lvaE Reverse |
| JMR573 | TGTTATACGCGCGTGTTCG (SEQ. ID. NO: 28) | lvaF Forward |
| JMR574 | GGTACACGTAGAACGCCGAC (SEQ. ID. NO: 29) | lvaF Reverse |
| JMR575 | CATGGTGTTCGTGCTGTTCACC (SEQ. ID. NO: 30) | lvaG Forward |
| JMR579 | GCCGAACAGCAACCTGATCA (SEQ. ID. NO: 31) | lvaG Reverse |
| *Operon-individual genes* | | |
| JMR3 | ACGCTGTGCTTCCTGTCCGTT (SEQ. ID. NO: 32) | lvaA Forward |
| JMR289 | CAGGTCGGGCAATGTCG (SEQ. ID. NO: 33) | lvaB Reverse |
| JMR576 | CCCACGAATTGCTCGAGATC (SEQ. ID. NO: 34) | lvaB Forward |
| JMR578 | GAAGCACGAACGGGCATGG (SEQ. ID. NO: 35) | lvaC Reverse |
| JMR301 | GCCGACAACATGATGGACCTG (SEQ. ID. NO: 36) | lvaC Forward |
| JMR299 | CGTGGTCCCAGGTTTGATCATC (SEQ. ID. NO: 37) | lvaD Reverse |
| JMR292 | GCTCGACACCAACCTCAAGG (SEQ. ID. NO: 38) | lvaD Forward |
| JMR333 | GCCAAGAACGCTTCGTAGTC (SEQ. ID. NO: 39) | lvaE Reverse |
| JMR11 | CAC GGT GCT GGA TAC CGA CA (SEQ. ID. NO: 40) | lvaE Forward |
| JMR574 | GGTACACGTAGAACGCCGAC (SEQ. ID. NO: 41) | lvaF Reverse |
| JMR573 | TGTTATACGCGCGTGTTCG (SEQ. ID. NO: 42) | lvaF Forward |
| JMR579 | GCCGAACAGCAACCTGATCA (SEQ. ID. NO: 43) | lvaG Reverse |

*P. putida* Knockouts

The genetic knockout of lvaD was performed following the protocol from Schafer et al. Schafer, A. et al. Small mobilizable multi-purpose cloning vectors derived from the *Escherichia coli* plasmids pK18 and pK19: selection of defined deletions in the chromosome of *Corynebacterium glutamicum*. Gene 145, 69-73 (1994). Knockouts of the remaining genes in *P. putida* were performed following the protocol from Graf et al. Graf, N. & Altenbuchner, J. Development of a method for markerless gene deletion in *Pseudomonas putida*. *Appl. Environ. Microbiol.* 77, 5549-52 (2011). Knockout constructs were designed with 500 bp of homology up and down stream of the deletion site. This region was cloned into the pJOE vector backbone. This suicide vector was transformed into *P. putida* KT2440 Δupp (*P. putida* KTU) through electroporation and colonies that successfully integrated the plasmid into the chromosome were selected on $LB_{kan}$ plates. A colony was then grown in LB media overnight to cure the counter-selection cassette. Various dilutions of the overnight culture were plated on $LB_{5-FU}$ plates to isolate colonies that had successfully excised the plasmid insertion. Colonies were then screened by colony PCR to isolate deletion strains.

Transcriptional Reporter Assay

*P. putida* KT2440 was transformed with pJMR74 through electroporation. pJMR74 is a broad host range plasmid containing a kan resistance marker and the predicted regulator for the lva operon, lvaR. Expressed divergent of lvaR is sfGFP cloned under the native promoter for lvaA. *P. putida* KT2440 containing empty vector pBAD35 was used as the no fluorescence control. Overnights of *P. putida*+pJMR74 or pBAD35 were inoculated at an OD600 of 0.05 in LB+kan50+20 mM of the appropriate carboxylic acid (acetate, propionate, butyrate, valerate, LA, 4HV, or hexanoate). Final time points were taken at 24 hours in a Tecan infinite m1000, with OD600 absorbance measured at 600 nm and fluorescence measured with an excitation of 485 nm and emission of 510 nm. Standard deviation error propagation was performed for the normalization of fluorescence and optical density measurements.

Protein Production and Purification

Vectors were constructed using the pET28b backbone and individually cloned genes from the *P. putida* genome. The plasmid containing lvaAB was constructed using the pET28b backbone and the lvaAB genes cloned as an operon directly out of *P. putida*'s genome. *E. coli* BL21 (DE3) strains with sequenced verified plasmids were grown at 37° C. in LB. Cultures were induced with 1 mM isopropyl-β-D-thiogalactopyranoside (IPTG) at an $OD_{600}$ of 0.4. The cultures were then chilled on ice for 10 minutes before incubation at 16° C. for 18 hours in New Brunswick Incubator 1-26. Then the cultures were centrifuged for 20 minutes at 5000×g in a Beckman Coulter Avanti J-E centrifuge. The supernatant was decanted and the cells resuspended in 30 mL of LB before another centrifugation at 5000×g for 20 minutes. The supernatant was removed and pellets stored at −80° C. for at least 24 hours.

Purification of His6- (lvaE) and Maltose Binding Protein (MBP)-Tagged Proteins (lvaABCD)

Frozen cell pellets were thawed on ice and resuspended in His6-lysis buffer (50 mM $Na_2HPO_4$, 300 mM NaCl, 10 mM imidazole, 2 mM DTT, pH 8.0) supplemented with 2 μL of benzonase or MBP-lysis buffer (20 mM Tris-HCl, 200 mM NaCl, 1 mM EDTA, 1 mM DTT, pH 7.4) supplemented with 2 μL of benzonase. Cell suspensions were sonicated 3 times using the program: 1.5 second pulse, 1.5 second pause, 40% duty, for a total of 30 second. Between each sonication cycle, the solution was stored on ice for 5 minutes. Lysed cells were centrifuged at 25,000×g at 4° C. for 30 min and the supernatant filtered through a 0.45 μm filter.

For the purification of His6-tagged proteins, a GE Äkta Start System with a 1 mL HisTrap HP column and a constant flow rate of 1 mL/minute was used. 5 column volume (CV) of wash buffer (50 mM $Na_2HPO_4$, 300 mM NaCl, 40 mM imidazole, 2 mM DTT, pH 8.0) was used to equilibrate the column. (GE Healthcare Life Sciences, Pittsburgh, PA.) The sample was loaded and washed with 15 CV wash buffer. The protein was eluted with 5 CV elution buffer (50 mM $Na_2HPO_4$, 300 mM NaCl, 250 mM imidazole, 2 mM DTT, pH 7.8). 1 mL fractions of eluted protein were collected. A GE PD-10 desalting column was used to buffer exchange the protein into the desalting buffer (100 mM Tris, 4.1 M glycerol and 2 mM DTT). An Amicon®-brand Ultra 4 mL Centrifugal Filter with a 10 kDa cut-off size was used to concentrate the protein. (MilliporeSigma, Billerica, MA.) Each protein was stored at −80° C. until use.

For the purification of MBP-tagged proteins, a GE Äkta Start System with a 1 mL MBPTrap HP column and a constant flow rate of 1 mL/minute was used. 5 column volume (CV) of wash buffer was used to equilibrate the column. The sample was loaded and washed with 15 CV wash buffer. The protein was eluted with 5 CV elution buffer (20 mM Tris-HCl, 200 mM NaCl, 1 mM EDTA, 1 mM DTT, 10 mM maltose, pH 7.4). 1 mL fractions of eluted protein were collected. A GE PD-10 desalting column was used to buffer exchange the protein into the desalting buffer (100 mM Tris, 4.1 M glycerol and 2 mM DTT). An Amicon® Ultra 4 mL Centrifugal Filter with a 10 kDa cut-off size was used to concentrate the protein. The protein was stored at −80° C. until use.

LvaAB Pulldown Experiment

All proteins for the pulldown experiment were purified on a 1 mL MBPTrap HP column, as previously described, regardless of the protein tag. LvaA was tagged with an N-terminal MBP tag. LvaAB was designed with LvaA tagged with an N-terminal MBP tag and LvaB untagged. Both proteins were expressed from the same construct as they appear in a native operon. For controls, LvaA contained an N-terminal His tag and was expressed with the native LvaB and the last control was an N-terminal MBP tagged LvaA containing a frameshift stop codon expressed with native LvaB. The purified proteins were analyzed on a 15% SDS-page gel to determine the major protein products.

Enzyme Assays and Metabolite Purification

All in vitro enzyme assays were performed in a 30° C. water bath at a pH of 6.5 and contained 50 mM Tris-HCL, 1 mM $MgCl_2$, and 2 mM DTT. Final reaction concentrations included the following components, depending on enzymes added: 0.5 mM LA, 0.55 mM CoA, 0.55 mM ATP (1.05 mM ATP when lvaAB were present), 0 mM NAD(P)H (0.55 mM NAD(P)H when lvaD was present). Final protein concentrations were: LvaA (0.2 μM), LvaB (0.8 μM), LvaAB (0.4 μM), LvaC (0.4 μM), LvaD (0.2 μM), and LvaE (0.2 μM) (data not shown). The in vitro enzyme assays were incubated for 30 minutes, excluding the time course which was incubated for various intervals up to 60 minutes. Reaction metabolites were purified following a modified protocol from Zhang, G. F. et al. Catabolism of 4-hydroxyacids and 4-hydroxynonenal via 4-hydroxy-4-phosphoacyl-CoAs. *J. Biol. Chem.* 284, 33521-33534 (2009). Reactions were quenched by adding methanol/water 1:1 containing 5% acetic acid in a 1:1 volume ratio (extraction buffer). Quenched reactions were run on a 1 mL ion exchange column prepacked with 100 mg 2-2(pyridyl)ethyl silica gel from MilliporeSigma. The column had been preconditioned with 1 mL methanol followed by 1 mL of extraction buffer. Metabolites load on the column were washed with 750 μL extraction buffer before being eluted with 1 mL of 4:1 methanol/250 mM ammonium formate, pH 6.3 and 1 mL methanol. Samples were dried using Thermo Scientific Savant SC250EXP Speedvac Concentrator and stored at −80° C. until LC/MS analysis. Samples for LC/MS analysis were resuspended in 100 uL 50 mM ammonium formate.

Liquid Chromatography Mass Spectrometry (LC/NIS, LC/NIS/MS)

Samples were analyzed using an HPLC-MS/MS system consisting of a Vanquish™ UHPLC system (Thermo Scientific) coupled by electrospray ionization (ESI; negative polarity) to a hybrid quadrupole-high-resolution mass spectrometer (Q Exactive orbitrap, Thermo Scientific) operated in full scan mode for detection of targeted compounds based on their accurate masses. Properties of Full MS-SIM included resolution of 140,000, AGC target of 1E6, maximum IT of 40 ms, and scan range from 70-1000 m/z. Liquid chromatography (LC) separation was achieved using an ACQUITY UPLC® BEH C18 (2.1×100 mm column, 1.7 μm particle size; Part No. 186002352; Serial No. 02623521115711; Waters, Milford, MA.). Solvent A was 97:3 water:methanol with 10 mM tributylamine (TBA) adjusted to pH 8.1-8.2 with 9 mM acetic acid. Solvent B was 100% methanol. Total run time was 25 min with the following gradient was: 0 min, 5% B; 2.5 min, 5% B; 5 min, 20% B; 7.5 mM, 20% B; 13 mM, 55% B; 15.5 mM, 95% B; 18.5 mM, 95% B; 19 mM, 5% B; 25 min, 5% B. Flow rate was 200 μL/min. The autosampler and the column temperatures were 4° C. and 25° C., respectively. Fragmentation of CoA, 4HV-CoA, and phosphorylated 4HV-CoA was achieved using parameters indicated in Table 5.

TABLE 5

| Other parameters for targeted MS/MS | |
|---|---|
| Resolution | 70,000 |
| AGC target | 1E6 |
| Maximum IT | 40 ms |
| Isolation width | 1.4 (m/z) |
| Fixed first mass | 70 m/z |
| (N)CE/stepped (N)CE | 15, 30, 45 |
| Default charge | 1 |
| Polarity | negative |

Enzymatic "In Gel" Digestion

"In gel" digestion and mass spectrometric analysis was done at the Mass Spectrometry Facility [Biotechnology Center, University of Wisconsin-Madison]. The digestion was performed as outlined on the website: www.biotech.wisc.edu/ServicesResearch/MassSpec/ingel.htm. In short, Coomassie Blue R-250 stained gel pieces were de-stained twice for 5 min in MeOH/$H_2$O/$NH_4HCO_3$ [50%:50%:100 mM], dehydrated for 5 min in ACN/$H_2$O/$NH_4HCO_3$ [50%:50%:25 mM] then once more for 1 min. in 100% ACN, dried in a Speed-Vac for 2 min., reduced in 25 mM DTT [dithiotreitol in 25 DTT [dithiotreitol in 25 mM $NH_4HCO_3$] for 30 min. at 56° C., alkylated with 55 mM IAA [iodoacetamide in 25 mM $NH_4HCO_3$] in darkness at room temperature for 30 min., washed twice in $H_2$O for 30 sec., equilibrated in 25 mM $NH_4HCO_3$ for 1 min., dehydrated for 5 min. in ACN/$H_2$O/$NH_4HCO_3$ [50%:50%:25 mM] then once more for 30 sec in 100% ACN, dried again and rehydrated with 20 μl of trypsin solution [10 ng/μl trypsin Gold (Promega) in 25 mM $NH_4HCO_3$/0.01% ProteaseMAX w/v (Promega)]. Additional 30 μl of digestion solution [25 mM $NH_4HCO_3$/0.01% ProteaseMAX w/v] was added to facilitate complete rehydration and excess overlay needed for peptide extraction. The digestion was conducted for 3 hrs at 42° C. Peptides generated from digestion were transferred to a new tube and acidified with 2.5% TFA [trifluoroacetic acid] to 0.3% final. Degraded ProteaseMAX was removed via centrifugation [max speed, 10 minutes] and the peptides solid phase extracted (ZipTip® C18 pipette tips Millipore, Billerica, MA)

NanoLC-MS/MS

Peptides were analyzed by nanoLC-MS/MS using the Agilent 1100 nanoflow system (Agilent) connected to a new generation hybrid linear ion trap-orbitrap mass spectrometer (LTQ-Orbitrap Elite™, Thermo Fisher Scientific) equipped with an EASY-Spray™ electrospray source. Chromatography of peptides prior to mass spectral analysis was accomplished using capillary emitter column (PepMap® C18, 3 μM, 100 Å, 150×0.075 mm, Thermo Fisher Scientific) onto which 2 μl of extracted peptides was automatically loaded. NanoHPLC system delivered solvents A: 0.1% (v/v) formic acid, and B: 99.9% (v/v) acetonitrile, 0.1% (v/v) formic acid at 0.50 μL/min to load the peptides (over a 30 minute period) and 0.3 μl/min to elute peptides directly into the nano-electrospray with gradual gradient from 3% (v/v) B to 30% (v/v) B over 77 minutes and concluded with 5 minute fast gradient from 30% (v/v) B to 50% (v/v) B at which time a 5 minute flash-out from 50-95% (v/v) B took place. As peptides eluted from the HPLC-column/electrospray source survey MS scans were acquired in the Orbitrap with a resolution of 120,000 followed by MS2 fragmentation of 20 most intense peptides detected in the MS1 scan from 300 to 2000 m/z; redundancy was limited by dynamic exclusion.

Data Analysis

Raw MS/MS data were converted to mgf file format using MSConvert (ProteoWizard: Open Source Software for Rapid Proteomics Tools Development. Mascot generic format (mgf) is a standard format for MS/MS searches in proteomics and is commonly used for small molecule MS/MS searching. It was developed by Matrix Science Inc., Boston, MA, which also makes and sells software for generating and manipulating mgf files.) Resulting mgf files were used to search against *Pseudomonas putida* amino acid sequence database containing a list of common contaminants (5,388 total entries) using in-house Mascot search engine 2.2.07 (Matrix Science) with variable methionine oxidation with asparagine and glutamine deamidation plus fixed cysteine carbamidomethylation. Peptide mass tolerance was set at 15 ppm and fragment mass at 0.6 Da.

Identification of Organisms with Potential Homologous LA Catabolism Pathways

Possible LvaABCD homologs were identified by performing a BLAST search of each protein sequence against the NCBI non-redundant protein sequence database using the BioPython library. Cock, P. J. A. et al. Biopython: freely available Python tools for computational molecular biology and bioinformatics. Bioinformatics 25, 1422-3 (2009). From the search results, the organism name was extracted from the sequence title and added to a set for each protein. The list of organisms containing the full set of LvaABCD enzymes was found by determining the intersection of the four sets of organism names from the BLAST results from each protein. A similar list was found for those organisms containing only LvaACD homologs. These lists were then used to query the original search results and find the lists of proteins that have homology to the proteins in the Lva pathway RB-TnSeq To further investigate genes involved in LA metabolism, random bar code transposon-site sequencing (RB-TnSeq) was performed for the growth of *Pseudomonas Putida* on LA and 4HV. RB-TnSeq is an efficient method for determining gene importance under different conditions with high genomic coverage. Wetmore, K. M. M. et al. Rapid Quantification of Mutant Fitness in Diverse Bacteria by Sequencing Randomly Bar-Coded Transposons. MBio 6, 1-15 (2015). A mixture of P1 oligos with variable length N space regions (2-5 nt) was used to "phase" the BarSeq PCR products for sequencing on an Illumina HiSeq4000. See Table 6. A summary of genes identified as interesting is shown in Table 7 including fitness scores for growth on minimal media with LA or 4HV relative to minimal media with glucose or the initial inoculum grown in LB.

TABLE 6

Modified Oligonucleotides used for BarSeq

| Oligo Name | Sequence |
|---|---|
| Barseq_P1 | AATGATACGGCGAC CACCGAGATCTACA CTCTTTCCCTACAC GACGCTCTTCCGAT CTNNNNNGTCGACC TGCAGCGTACG (SEQ. ID. NO: 44) |

TABLE 6-continued

Modified Oligonucleotides used for BarSeq

| Oligo Name | Sequence |
|---|---|
| Barseq_P1_4N | AATGATACGGCGAC CACCGAGATCTACA CTCTTTCCCTACAC GACGCTCTTCCGAT CTNNNNGTCGACCT GCAGCGTACG (SEQ. ID. NO: 45) |
| Barseq_P1_3N | AATGATACGGCGAC CACCGAGATCTACA CTCTTTCCCTACAC GACGCTCTTCCGAT CTNNNGTCGACCTG CAGCGTACG (SEQ. ID. NO: 46) |
| Barseq_P1_2N | AATGATACGGCGAC CACCGAGATCTACA CTCTTTCCCTACAC GACGCTCTTCCGAT CTNNGTCGACCTGC AGCGTACG (SEQ. ID. NO: 47) |

TABLE 7

Genes Identified as Interesting

| Locus | Name | Annotation | LA/Gluc | 4HV/Gluc |
|---|---|---|---|---|
| PP_0364 | bioH | pimeloyl-ACP methyl ester esterase | 0.3 | 0.02 |
| PP_0988 | gcvP-1 | glycine dehydrogenase | −0.02 | −0.003 |
| PP_2332 | — | ATP-dependent zinc protease family | −0.1 | 0.2 |
| PP_2336 | acnA-II | aconitate hydratase | −4.5 | −3.5 |
| PP_2337 | prpF | aconitate isomerase | −4.4 | −3.8 |
| PP_2790 | lvaR | Sigma-54 dependent sensory box protein | −3.9 | −5.0 |
| PP_2791 | lvaA | Aminoglycoside phosphotransferase | −5.2 | −4.2 |
| PP_2792 | lvaB | Hypothetical protein | NA | NA |
| PP_2793 | lvaC | acyl-CoA dehydrogenase/reductase family | −5.2 | −4.1 |
| PP_2794 | lvaD | Oxidoreductase, short chain dehydrogenase/reductase family | −6.5 | −5.3 |
| PP_2795 | lvaE | Acyl-CoA synthetase | 0.4 | −4.6 |
| PP_2796 | lvaF | conserved protein of unknown function | 0.2 | 0.7 |
| PP_2797 | lvaG | acetate permease | 0.1 | 1.7 |
| PP_3741 | mrdA-I | transpeptidase | 0.0 | −0.06 |
| PP_4217 | fpvA | TonB-dependent outer membrane ferripyoverdine receptor | 0.3 | 0.02 |
| Important for Fitness in LA and 4HV | | | | |
| PP_2217 | | enoyl-CoA hydratase | −2.0 | −2.2 |
| PP_2334 | | 2-methylisocitrate lyase | −4.9 | −3.3 |
| PP_2335 | | methylcitrate synthase | −5.1 | −4.7 |
| PP_3286 | | DNA-binding transcriptional repressor PaaX(phenylacetyl-CoA) | −4.3 | −4.1 |
| PP_3753 | | Transcriptional regulator, AraC family | −4.8 | −2.6 |
| PP_3754 | | Beta-ketothiolase BktB | −5.8 | −3.2 |
| PP_3755 | | 3-hydroxybutyryl-CoA dehydrogenase | −2.9 | −3.1 |
| Important for Fitness in LA but not 4HV | | | | |
| PP_1291 | | PhoH family protein | −2.5 | 0.3 |
| PP_2333 | | GntR family transcriptional regulator | −4.5 | −0.7 |
| PP_3121 | | transcriptional regulator, LysR family | −4.1 | −0.3 |
| PP_3122 | | acetoacetyl CoA-transferase (subunit A) | −2.3 | −0.1 |
| PP_3123 | | acetoacetyl CoA-transferase (subunit B) | −3.1 | −0.02 |
| PP_3925 | | conserved protein of unknown function | −2.1 | −0.9 |
| PP_4515 | | Transcriptional regulator, MarR family | −2.2 | 0.03 |
| PP_4628 | | conserved protein of unknown function | −3.6 | −1.3 |
| Important for Fitness in 4HV but not LA | | | | |
| PP_0951 | | Ribosome hibernation promoting factor | 0.2 | −2.4 |
| PP_0995 | | Putative sigma factor regulator | −0.5 | −2.6 |

TABLE 7-continued

Genes Identified as Interesting
Genes Identified as Interesting

| Locus | Name | Annotation | LA/Gluc | 4HV/Gluc |
|---|---|---|---|---|
| PP_1328 | | Protein MraZ | −0.5 | −4.2 |
| PP_1764 | | Phosphoglycolate phosphatase 2 | −1.3 | −2.7 |
| PP_1778 | | Lipopolysaccharide ABC export system, permease protein | 0.2 | −4.8 |
| PP_1779 | | Lipopolysaccharide ABC export system, ATP-binding protein | 0.003 | −4.0 |
| PP_1968 | | TetR family transcriptional regulator | −0.8 | −2.1 |
| PP_2082 | | phosphoenolpyruvate synthetase | −0.2 | −2.7 |
| PP_2436 | | Transcriptional regulator, LysR family | −0.3 | −2.4 |
| PP_4342 | | flagellar synthesis regulator, putative ATPase | −1.4 | −2.0 |
| PP_4571 | | cysteine synthase A | −0.1 | −3.5 |
| PP_4762 | | Acyl-CoA thioesterase II | 0.3 | −4.3 |

Methods

P. putida Library Preparation

We generated a DNA-barcoded transposon mutant library of P. putida KT2440 using previously described methods and resources. (Wetmore et al., supra.) Briefly, we conjugated wild-type P. putida KT2440 with an E. coli strain (WM3064) carrying the transposon vector library pKMW3. pKMW3 is a mariner class transposon vector library containing a kanamycin resistance marker and millions of random 20mer DNA barcodes. Conjugations were performed at 1:1 donor:recipient ratio on LB+diaminopimelic acid (DAP) plates for 6 hours and finally plated on LB plates supplemented with 100 ug/mL kanamycin. The E. coli conjugation strain WM3064 is auxotrophic for DAP and does not grow on media that is not supplemented with this compound. We combined thousands of kanamycin-resistant P. putida colonies into a single tube, made multiple aliquots, and stored these samples at −80° C. for future use. We also extracted genomic DNA and mapped the transposon insertion locations and their associated DNA barcodes via a TnSeq-like Illumina sequencing protocol, as previously described by Wetmore et al. (supra). We named the final, sequenced mapped transposon mutant library Putida_ML5.

LA and 4HV Growth Experiments

An aliquot of the P. putida RB-TnSeq library (Putida_ML5) was grown for 5 hours in a shake flask containing 25 mL of LB media with 50 ug/mL Kanamycin Sulfate to late log phase (30° C., 250 RPM). 1 OD600*mL of cells were pelleted, decanted, and frozen at −20° C. for barcode sequencing as the time zero inoculum control. 1 OD600*mL of cells per treatment were washed with three volumes of minimal media with no carbon source and then resuspended in 2× minimal media with no carbon source for a new OD600 measurement. These cells were diluted into 2× minimal media to an OD600 of 0.04. This culture was then diluted in half with 2× solutions of each carbon source of interest to a final volume of 10 mL in a culture tube for 4HV and 1.2 mL total volume in the well of a 24-well microplate for LA. The carbon sources tested were 40 mM 4HV (pH adjusted to 7 with NaOH), 40 mM LA (pH adjusted to 7 with NaOH), 20 mM potassium acetate, and 40 mM glucose, each with two replicates. The 4HV and acetate experiments were performed one day and the LA experiments were performed on a different day, each day with its own 40 mM Glucose control. The culture tubes were placed in a shaker incubator (30° C., 250 RPM) until they achieved and OD600 of −3 for 40 mM Glucose (~20 hours), ~0.25 for 20 mM potassium acetate (~44 hours), or −0.3-0.5 for 40 mM 4HV (~68 hours). For LA, the samples were grown in a 24-well microplate in a Multitron shaker set to 30° C. and 700 rpm.

We monitored the OD of the microplate in a Tecan M1000 microplate reader. A 1 mL sample from each culture tube was pelleted and frozen at −20° C. for barcode sequencing.

BarSeq

A DNA barcode sequencing (BarSeq) was performed as described in Wetmore et al. (supra), with a slight variation in the common P1 oligo design. In this study, a mixture of P1 oligos with variable length N space regions (2-5 nt) was used to "phase" the BarSeq PCR products for sequencing on the Illumina HiSeq4000.

Data Analysis

Both the TnSeq data and the BarSeq data were processed using analysis scripts as described in Wetmore et al. (supra). Briefly, the fitness of a strain in the normalized $\log_2$ ratio of barcode reads in the experimental sample to barcode reads in the time zero sample. The fitness of a gene is the weighted average of the strain fitness for insertions in the central 10-90% of the gene. The gene fitness values are normalized so that the typical gene has a fitness of zero. The primary statistic t-value is of the form of fitness divided by the estimated variance across different mutants of the same gene. All experiments described herein pass the quality metrics described in Wetmore et al. unless noted otherwise.

Identifying Genes of Interest

The fitness values reported in Table 7 are the average of 2 replicates. Fitness scores for LA and 4HV relative to glucose were calculated using the following equation:

$$\text{Fitness}\left(\frac{LA}{\text{Glucose}}\right) = \text{Fitness}(LA) - \text{Fitness}(\text{Glucose})$$

Annotations in Table 7 and discussed in the text below were adapted from Dehal, P. S. et al. MicrobesOnline: An integrated portal for comparative and functional genomics. Nucleic Acids Res. 38, 396-400 (2009).

RB-TnSeq Results are Consistent with the Other Evidence

All genes mentioned above are shown with their fitness scores for growth on LA and 4HV in Table 6. Genes that were identified as transposon library hits have their gene loci highlighted in red italics.

RB-TnSeq analysis suggests the genes identified as constituting the LA metabolism operon lvaABCDEFG as well as the proposed regulator lvaR were important for growth on both LA and 4HV with a few exceptions described as follows. lvaB was excluded from the data summary for growth on LA and 4HV due to insufficient barcode insertions in this small gene and lvaE (shown to not be essential for growth on LA in the main text) shows no phenotype on LA.

RB-TnSeq analysis suggests lvaF and lvaG are not important for growth on LA or 4HV, suggesting they are not required for transport of these metabolites at the concentrations used in the experiments. The positive fitness scores of these genes for growth on 4HV suggest that the 4HV concentrations used in this experiment had negative effects on fitness, an effect that would be alleviated by elimination of import system (See section below: Potential Induction of Quorum-Sensing Systems by γ-Valerolactone). None of the remaining transposon library hits noted herein exhibited interesting phenotypes in the RB-TnSeq experiment, suggesting they may have been dependent upon the transposon library experiment.

In addition to genes identified in above, genes of interest shown in Table 6 were identified using the following criteria:

Important for Fitness in LA and 4HV: Fitness scores lower than −2 for both LA and 4HV. Important for Fitness in LA but not 4HV: Fitness score for LA lower than −2 and fitness score for 4HV greater than −2.

Important for Fitness in 4HV but not LA: Fitness score for 4HV lower than −2 and fitness score for LA greater than −2.

Enhanced Fitness in 4HV: Fitness score greater than 2 for 4HV.

This list of genes of interest was further refined by eliminating genes that shared a phenotype with growth on acetate as these results were considered not relevant to the scope of this work.

β-Oxidation of 3-Hydroxyvaleryl-CoA to Propionyl-CoA and Acetyl-CoA by Genes Important for Growth on LA and 4HV As proposed above, the 3-hydroxyvaleryl-CoA metabolite produced in LA metabolism could be utilized through β-Oxidation to form Propionyl-CoA and Acetyl-CoA. RB-TnSeq analysis helped to identify potential candidate genes for this pathway:

PP_3755 is annotated as a 3-hydroxybutyryl-CoA dehydrogenase, suggesting that this enzyme catalyzes the conversion of 3-hydroxyvaleryl-CoA to 3-ketovaleryl-CoA.

PP_3754 is annotated as a β-ketothiolase, suggesting that this enzyme catalyzes the conversion of 3-ketovaleryl-CoA to propionyl-CoA and Acetyl-CoA.

PP_3753 is annotated as a transcriptional regulator and its location directly upstream of the two previous genes suggests a role in the regulation of these two β-oxidation genes.

Propionyl-CoA Metabolism by Genes Important for Growth on LA and 4HV

After propionyl-CoA is formed through the mechanism proposed in the previous section, it could be further metabolized to form succinate and pyruvate through the 2-methylcitrate cycle. PP_2337 is annotated as a methylaconitate isomerase (prpF), suggesting that the pathway utilized is the 2-methylcitrate cycle II that passes through a trans-2-methyl-aconitate intermediate. RB-TnSeq analysis helped to identify potential candidate genes for this pathway:

PP_2335 is annotated as a methylcitrate synthase, suggesting that this enzyme catalyzes the reaction of propionyl-CoA with oxaloacetate to form 2-methylcitrate.

PP_2336 is annotated as an aconitate hydratase. PP_2339, an additional gene in close chromosomal proximity but with insufficient BarSeq data for analysis is also annotated as an aconitate hydratase. These results suggest that some combination of these two enzymes catalyze both the conversion of 2-methylcitrate to trans-2-methylaconitate and the downstream conversion of cis-2-methylaconitate to 2-methylisocitrate.

PP_2337 is annotated as a methylaconitate isomerase, suggesting that this enzyme catalyzes the conversion of trans-2-methylaconitate to cis-2-methylaconitate.

PP_2334 is annotated as a 2-methylisocitrate lyase, suggesting that this enzyme catalyzes the conversion of 2-methylisocitrate to succinate and pyruvate.

PP_2333 is annotated as a transcriptional regulator and its location directly upstream of the PP_2334-2339 genes suggests a role in the regulation of these propionyl-CoA metabolism genes.

Potential LA CoA Transferase lvaE was shown to catalyze the conversion of LA to levulinyl-CoA as well as the conversion of 4HV to 4-hydroxyvalerly-CoA. lvaE is essential for growth on 4HV but not essential for growth on LA, suggesting that there is another enzyme capable of catalyzing the conversion of LA to levulinyl-CoA. PP_3122 and PP_3123 are annotated as acetoacetyl CoA-transferase subunits A and B respectively and are both important for growth on LA but not 4HV, suggesting they could fill the role of the additional catalyst for levulinyl-CoA formation. PP_3121 is also important for growth on LA but not 4HV and is annotated as a transcriptional regulator. Its genomic context suggests it regulates the expression of PP_3122 and PP_3123. This set of genes is analogous to the dhcAB operon involved in catabolism of carnitine in *Pseudomonas aeruginosa*. PP_3121 shares 72% sequence identity across 95% of its sequence with dhcR (PA1998) and PP_3122 and PP_3123 share 86% and 90% identity across their entire sequences with dhcA (PA1999) and dhcB (PA2000), respectively. dhcR regulates expression of the dhcAB operon encoding a predicted 3-ketoacid CoA-transferase with evidence of activity on 3-dehydrocarnitine. Wargo, M. J. & Hogan, D. A. Identification of genes required for *Pseudomonas aeruginosa* carnitine catabolism. *Microbiology* 155, 2411-2419 (2009). PP_3121-PP_3123 could serve a similar role in catabolism of LA.

Transcriptional Regulators Control Both Beneficial and Detrimental Systems for Fitness Under LA and 4HV Metabolism PP_3286 and PP_3753 are annotated as transcriptional regulators and RB-TnSeq analysis suggests they are important for growth on LA and 4HV. The annotation for PP_3286 suggests involvement in the regulation of phenylacetic acid metabolism. As previously stated, genomic context suggests the involvement of PP_3753 in the regulation of the probable β-oxidation genes PP_3754-3755.

PP_3121 and PP_4515 are annotated as transcriptional regulators and RB-TnSeq analysis suggests they are important for growth on LA but not important for growth on 4HV. As previously stated, genomic context suggests PP_3121 regulates expression of the potential acetoacetyl-CoA transferase subunits PP_3122-3123. The regulatory role of PP_4515 is unclear.

Conversely, PP_0995, PP_1328, PP_1968, PP_2333, and PP_2436 are annotated as transcriptional regulators and RB-TnSeq analysis suggests they are important for growth on 4HV, but not important for growth on LA. PP_0995 shares 41% homology across its entire sequence with a gene in *Caulobacter crescentus* (CC3252) thought to be involved in sigma factor regulation for heavy metal stress, although its regulatory role in *Pseudomonas putida* is unclear. Kohler, C., Lourenço, R. F., Avelar, G. M. & Gomes, S. L. Extracytoplasmic function (ECF) sigma factor σF is involved in *Caulobacter crescentus* response to heavy metal stress. *BMC Microbiol.* 12, 210 (2012). As previously stated, genomic context suggests the involvement of PP_2333 in the regulation of the probable propionyl-CoA metabolism genes PP_2333-2339. The regulatory functions of PP_1328, PP_1968, and PP_2436 are unclear.

PP_0191, PP_1236, PP_2144, PP_3603, and PP_4734 are annotated as transcriptional regulators and RB-TnSeq analysis suggests their deletions are beneficial for growth on 4HV. PP_0191 is annotated as a regulator of alginate bioaccumulation, suggesting a role in biofilm formation. PP_1236 is annotated as a regulator of a glycine cleavage system and a close homolog in *Pseudomonas aeruginosa* (PA1009) is involved in the regulation of host colonization. Koh, A. Y. et al. Utility of in vivo transcription profiling for identifying *Pseudomonas aeruginosa* genes needed for gastrointestinal colonization and dissemination. PLoS One 5, 1-14 (2010). PP_2144 has a close homolog in *Pseudomonas syringae* (psrA) that is involved in the regulation of epiphytic fitness, quorum-sensing, and plant host interactions. Chatterjee, A., Cui, Y., Hasegawa, H. & Chatterjee, A. K. PsrA, the *Pseudomonas* sigma regulator, controls regulators of epiphytic fitness, quorum-sensing signals, and plant interactions in *Pseudomonas syringae* pv. *tomato* strain DC3000. Appl. Environ. Microbiol. 73, 3684-3694 (2007).

PP_3603 and PP_4734 are annotated as fatty acid responsive transcriptional regulators with unknown regulatory roles.

Potential Induction of Quorum-Sensing Systems by γ-Valerolactone

4HV used in the RB-TnSeq experiments was synthesized from γ-valerolactone as described in the methods section of the main text. As a result, residual γ-valerolactone was likely present in the experiments for growth on 4HV. Several molecules in the lactone family are known to be used as quorum sensing signals in Pseudomonads. Pearson, J. P., Passador, L., Iglewski, B. H. & Greenberg, E. P. A second N-acylhomoserine lactone signal produced by *Pseudomonas aeruginosa*. Proc. Natl. Acad. Sci. U.S.A 92, 1490-1494 (1995). Quorum sensing responses would likely cause physiological responses towards the formation of a biofilm in the culture vessel. Cells with disruptions in these regulatory systems would replicate themselves to a higher degree resulting in a perceived increase in fitness as is the case with the transcriptional regulators PP_0191, PP_1236, and PP_2144 discussed above. As γ-Valerolactone is being investigated as a promising solvent for nonenzymatic sugar production from biomass (see Luterbacher, J. S. et al. Nonenzymatic Sugar Production from Biomass Using Biomass-Derived gamma-Valerolactone. *Science* (80-.). 343, 277-281 (2014)), its effect on the quorum sensing systems of potential platform host organisms for bioprocessing should be further investigated.

Conferring Growth on Levulinic Acid to *E. coli* LS5218

*E. coli* strain LS5218 is commonly studied for the production of polyhydroxyalkanoates (PHAs) and carries two known mutations: a mutation in fadR, which deregulates the genes encoding the β-oxidation enzymes and allows for constitutive expression of the fad genes, and an atoC(Con) mutation that causes constitutive upregulation of the ato operon, an operon responsible for the metabolism of short-chain fatty acids. The mutations in *E. coli* LS5218 allow for increased uptake and utilization of a wider array of fatty acid chain lengths, and make it especially adapted for the engineering of short chain length-co-medium chain length (SCL-co-MCL) copolymers and poly(3-hydroxybutyrate-co-3-hydroxyvalerate) [P(3HB-co-3HV)].

LA is catabolized into equal moles of acetyl-CoA and propionyl-CoA. While *E. coli* contains the necessary genes for propionyl-CoA metabolism, elevated propionyl-CoA concentrations are known to be inhibitory. Therefore, we performed a growth study to evaluate growth of *E. coli* on various concentrations of propionate, with and without acetate as a secondary carbon source. The maximum allowable concentration that stimulated growth was 20 mM propionate, both in the presence and absence of acetate (data not shown). Using this information, we designed all LA growth experiments to contain the maximum concentration of 20 mM LA to minimize false negative growth phenotypes resulting from propionate toxicity.

The five biosynthetic enzymes required for catabolizing LA into a common β-oxidation intermediate (lvaABCDE) were expressed as an operon in *E. coli* LS5218 from the plasmid pJMR5 (SC101 origin, $P_{tet}$, kanR). We hypothesized that this combination of expressed enzymes would confer LA catabolism in *E. coli*. However, in initial trials *E. coli* LS5128 pJMR5 failed to grow on LA as a sole carbon source (data not shown). Therefore, we performed adaptive evolution, sub-culturing cells into fresh media daily, to evolve a strain capable of LA catabolism. The first three rounds were conducted with both LA and acetate as available carbon to stimulate growth and allow cells to adapt to the presence of LA. In these experiments, we observed an increase in final cell density when both carbon sources were present relative to cultures that were fed only acetate. Subsequent rounds of evolution were conducted with LA as the sole carbon source. After 14 rounds of sub-culturing on LA, we isolated two mutant strains, M141 and M142, capable of robust LA catabolism.

We purified the lvaABCDE expression plasmid from the mutant strains and sequenced it to determine if evolutionary changes were due to plasmid-borne mutations. A mutation in the ribosome binding sequence (RBS) for the lvaABCDE operon was discovered. See Table 8. RBS Calculators predicted an increased translation initiation rate relative to the original sequence. We retransformed the isolated plasmid, designated p2, back into wild type LS5218 and the resulting strain did not have the LA growth phenotype, indicating genomic mutations were also necessary (data not shown). To isolate the essential genomic mutations, we submitted strains M141 and M142 for whole genome sequencing after curing out the plasmid. The sequencing results highlighted five mutations in M141 and four mutations in M142 when compared with the genome sequence assembled for wild type *E. coli* LS5218 (GCA_002007165.1), with only two common mutations between both strains (Table 8). The common mutations were a point mutation in fadE that resulted in a premature stop codon causing a functional deletion and the insertion of transposons into atoC that also resulted in a premature stop codon and a functional deletion.

TABLE 8

List of mutations from evolved strains M141 and M142

| Position | Gene | Mutation | Change |
|---|---|---|---|
| \multicolumn{4}{c}{Genomic mutations Common} | | | |
| 243014 | fadE | C →T | Trp → stop codon |
| 2323064 | atoC (M141) | Transposable element insertion | Early stop codon |
| 2322858 | atoC (M142) | Transposable element insertion M141 | Early stop codon |
| 205559 | dnaE | G →A | Arg →His |
| 261153 | proB | C →T | His →Tyr |
| 3390059 | aaeR | A →C | Lys →Asn |

TABLE 8-continued

List of mutations from evolved strains M141 and M142

| Position | Gene | Mutation | Change |
|---|---|---|---|
| | | M142 | |
| 2395921 | nuoI | C →T | Ser →Asn |
| 4161154 | fabR | A →C | Thr →Pro |
| | | Plasmid mutations | |
| pJMR5 | RBS | G →T | Increased RBS strength |

To verify the importance of the common mutations we generated clean knockouts of fadE and/or atoC using CRISPR-Cas9 mediated genome engineering. Jiang, W., Bikard, D., Cox, D., Zhang, F. & Marraffini, L. a. RNA-guided editing of bacterial genomes using CRISPR-Cas systems. *Nat Biotechnol* 31, 233-239 (2013). Jiang, Y. et al. Multigene editing in the *Escherichia coli* genome via the CRISPR-Cas9 system. *Appl. Environ. Microbiol.* 81, 2506-2514 (2015). Li, Y. et al. Metabolic engineering of *Escherichia coli* using CRISPR-Cas9 meditated genome editing. *Metab. Eng.* 31, 13-21 (2015). We transformed each strain with the plasmid pJMR32, a redesigned pJMR5 with predicted increased RBS strength for LvaA. We examined growth on LA as a sole carbon source for each strain. Wild type LS5218 and LS5218 ΔatoC were unable to grow on LA whereas LS5218 ΔfadE and LS5218 ΔatoC ΔfadE grew robustly (equivalent to the positive control—*E. coli* M142 with pJMR32) on LA as the sole carbon source. See Table 9. These experiments demonstrated that the fadE deletion was necessary for growth, but the role of the atoC deletion remained unclear. We generated growth curves on LA for strains LS5218 ΔfadE, LS5218 ΔatoC ΔfadE and M142 and found that LS5218 ΔfadE has a significantly longer lag period compared with LS5218 ΔatoC ΔfadE and M142 (data not shown). This indicates that in *E. coli* LS5218, a fadE deletion and an atoC deletion are beneficial.

TABLE 9

LS5218 Growth on LA.

| LS5218 Strains[a] | Growth on LA |
|---|---|
| Wild Type | -- |
| ΔfadE | ++ |
| ΔatoC | -- |
| ΔfadE ΔatoC | ++ |
| M142 | ++ |

[a]All strains carrying pJMR32;
--, no growth;
++, robust growth

FadE is an acyl-CoA dehydrogenase enzyme that catalyzes the formation of a trans-2-enoyl-CoA from an acyl-CoA compound. Because the LA catabolic pathway terminates at the formation of 3HV-CoA, the final steps to be completed by the *E. coli* β-oxidation pathway would only involve fadBA, so it remains unclear as to why a fadE deletion is beneficial for growth. We hypothesize that FadE may be active towards LA-CoA, adding a double bond at the 2 position of the γ-ketovaleryl-CoA species and sequestering the molecule from further degradation. FadE is an inner membrane protein that has not been purified for in vitro characterization. Díaz-Mejía, J. J., Babu, M. & Emili, A. Computational and experimental approaches to chart the *Escherichia coli* cell-envelope-associated proteome and interactome. *FEMS Microbiol. Rev.* 33, 66-97 (2009).

The deletion of atoC was not a necessary mutation, but did confer a growth benefit. This mutation was isolated during through the directed evolution process because we were screening for mutants with reduced lag phases, thereby enriching our mutant population with strains containing the early termination sequence. Constitutive activation of the ato regulon by the atoC(Con) mutation in LS5218 causes an overexpression of an acetoacetyl-CoA transferase (encoded by atoDA), an acetyl-CoA acetyltransferase (encoded by atoB) and a short chain fatty acid transporter (encoded by atoE). We propose that the 3-ketovaleryl-CoA intermediate was diverted from the final cleavage step into central metabolites by AtoDA, releasing 3-ketovalerate. The sequestering of LA as 3-ketovalerate reduces overall carbon flow to central metabolites, stunting growth of the *E. coli* strains until they can adapt for the utilization of 3-ketovalerate. Reducing expression of AtoDA through the deletion of atoC would prevent the formation of the secondary pathway, allowing direct flux of LA to central metabolites. Additionally, AtoE is a short chain fatty acid transporter and overexpression could be causing an increase in the intracellular concentration of LA above a threshold LS5218 is capable of tolerating, causing an extended lag phase. Monitoring intracellular metabolites during the extended lag phase could be useful in isolating the exact cause when compared with the ΔatoC strains.

Directed Evolution of *E. coli* LS5218

*E. coli* was grown at 37° C., unless otherwise stated. Sub-culturing experiments were done with a volume of 5 ml in glass test tubes (20×150 mm, Fisher Scientific) with 250 rpm agitation in a 126 shaker (New Brunswick Scientific, Edison, NJ). Starting media contained 20 mM LA and 40 mM acetate or 40 mM acetate only for negative control. Cultures were grown for 72 hours and optical density (OD) measurements taken with a Spectronic 20 (Milton Roy Company, Warminster, PA), then culture were diluted 1:100 into fresh media. Once the OD in the LA and acetate cultures exceeded the OD of the acetate only cultures, further growth media was 20 mM LA only. These cultures were incubated until turbidity was observed visually, then diluted 1:100 into fresh media. This occurred for a total of 14 dilutions steps in LA media, spanning two weeks.

Plasmids were prepped (QIAprep® Miniprep Kits, Qiagen) and sequenced (Functional Biosciences) to find mutations. Plasmids were cured out of mutate strains through serial culturing in rich media (LB broth) and patch plated on LB and $LB_{kan50}$.

Developing a Growth-Coupled Strain

To further increase the yield of 2-butanone from LA, three strategies were computationally evaluated for producing 3-ketovalerate (3 KV) from 3-ketovaleryl-CoA (3 KV-CoA) .The first method uses a thioesterase to hydrolyze 3 KV-CoA to 3 KV, which results in a strain incapable of growth without another carbon source but is theoretically capable of complete conversion of LA to butanone. The other two strategies couple butanone production to energy generation and/or cell growth. For example, the CoA moiety from 3 KV-CoA can be transferred to succinate, thereby generating 3 KV, via a succinyl-CoA transferase encoded by PcaIJ in *Pseudomonas putida*. With the addition of an equimolar feed of succinate and deletion of all reactions forming succinyl-CoA (SUCOAS, AKGDH, 3OXCOAT, PPCSCT) other than the PcaIJ reaction, it was determined that the maximum growth rate (0.48 $hr^{-1}$) required production of butanone at a rate of 0.25 mmol $gDW^{-1}$ $hr^{-1}$ (data not shown). While promising, this approach required a large number of deletions and maximum growth occurred with a relatively low amount of butanone production. Alternatively, it was found that butanone production could be coupled to acetate assimilation via E. coli's native acetyl-CoA transferase, AtoDA. By knocking out acetate fermentation (reactions ACKr and PTAr) and acetyl-CoA synthesis from acetate (reaction ACS), the only way for E. coli to make acetyl-CoA was through the transfer of CoA from 3HV-CoA to exogenous acetate. In this case, a maximum predicted 2-butanone production rate of 10 mmol gDW$^{-1}$ hr$^{-1}$ was achieved (i.e. complete bioconversion) with a maximum predicted growth rate of 0.21 hr$^{-1}$. This approach predicted the possibility of a strongly growth-coupled bioconversion of LA to butanone. This growth-coupled strain, eMEK8, was constructed by deleting ackApta and acs in strain eMEK4.

In a separate evolution experiment using E. coli K12 MG1655, a variant of the pJMR032 plasmid was discovered with a single nucleotide mutation causing a V111F variant on the Rep101 protein that improved catabolism of LA. The V111F mutation was the re-introduced into the Rep101 gene into pJMR032 creating plasmid pJMR032QC. This mutation significantly increased the growth rate of eMEK8 when compared to eMEK8 containing the plasmid without the V11F mutation (data not shown). Because a mutation in the origin is likely to affect the copy number of the plasmid, qPCR determined that the mutant plasmid had a copy number threefold higher than the original plasmid (data not shown).

To experimentally test the growth coupling strategy, cultures of eMEK8 with plasmids pJMR032QC and pJMR095 were grown in minimal media using LA and/or acetate at the carbon source. These data (not shown) revealed no growth of eMEK8 on LA or acetate alone but significant growth when both substrates are supplied, indicating that growth of eMEK8 is successfully coupled to LA metabolism. The effect of different ratios of LA and acetate on the production of 2-butanone was then examined. Importantly, in the case where LA was supplied at half the molar ratio as acetate (1:0.5), the LA was consumed in its entirety while acetate remained in the media. When supplied in equimolar ratios, the acetate and LA consumption are nearly identical (~15 mM) and the measured yield of 2-butanone on LA is 76% (855 mg/L or 11.9 mM). The results from these experiments with the growth-coupled strain stand in stark contrast to the data from the non-growth-coupled strain, where all the supplied acetate was consumed in every case.

What is claimed is:

1. A method of making 2-butanone, the method comprising culturing a genetically modified host cell transformed to contain and express a heterologous recombinant expression vector comprising at least one promoter operably linked to at least three nucleotide sequences selected from the group consisting of lvaA, lvaB, lvaC, lvaD, and lvaE, wherein lvaA has a nucleotide sequence having at least 90% sequence identity to SEQ. ID. NO: 1, lvaB has a nucleotide sequence having at least 90% sequence identity to SEQ. ID. NO: 3, lvaC has a nucleotide sequence having at least 90% sequence identity to SEQ. ID. NO: 5, lvaD has a nucleotide sequence having at least 90% sequence identity to SEQ. ID. NO: 7, and lvaE has a nucleotide sequence having at least 90% sequence identity to SEQ. ID. NO: 9, in a medium containing levulinic acid, under conditions and for a time wherein at least a portion of the levulinic acid is catabolized by action of the host cell into 2-butanone.

2. The method of claim 1, wherein the heterologous recombinant expression vector comprises the at least one promoter operably linked to at least four nucleotide sequences selected from the group consisting of lvaA, lvaB, lvaC, lvaD, and lvaE.

3. The method of claim 1, wherein the heterologous recombinant expression vector comprises the at least one promoter operably linked to lvaA, lvaB, lvaC, lvaD, and lvaE.

* * * * *